United States Patent
Blackman et al.

(10) Patent No.: US 9,658,211 B2
(45) Date of Patent: *May 23, 2017

(54) IN VITRO MODEL FOR PATHOLOGICAL OR PHYSIOLOGIC CONDITIONS

(71) Applicant: HemoShear, LLC, Charlottesville, VA (US)

(72) Inventors: Brett R. Blackman, Charlottesville, VA (US); Brian R. Warnhoff, Charlottesville, VA (US); Ajit Dash, Charlottesville, VA (US); Michael B. Simmers, Charlottesville, VA (US); Ryan E. Feaver, Charlottesville, VA (US)

(73) Assignee: HemoShear, LLC, Charlottesville, VA (US)

( * ) Notice: Subject to any disclaimer, the term of this patent is extended or adjusted under 35 U.S.C. 154(b) by 346 days.

This patent is subject to a terminal disclaimer.

(21) Appl. No.: 13/866,017

(22) Filed: Apr. 18, 2013

(65) Prior Publication Data
US 2013/0309677 A1 Nov. 21, 2013

Related U.S. Application Data

(60) Provisional application No. 61/724,864, filed on Nov. 9, 2012, provisional application No. 61/635,118, filed on Apr. 18, 2012.

(51) Int. Cl.
C12N 5/02 (2006.01)
G01N 33/50 (2006.01)
C12M 1/42 (2006.01)

(52) U.S. Cl.
CPC ..... G01N 33/5067 (2013.01); G01N 33/5008 (2013.01); G01N 33/5023 (2013.01);
(Continued)

(58) Field of Classification Search
CPC .......... G01N 33/5067; G01N 33/5023; G01N 2800/7004; G01N 33/5091; G01N 35/04; G01N 33/5008
See application file for complete search history.

(56) References Cited

U.S. PATENT DOCUMENTS 7,811,782 B2 10/2010 Blackman et al.
2002/0119441 A1 8/2002 Elias
(Continued)

FOREIGN PATENT DOCUMENTS

WO 98/03634 A1 1/1998
WO 02/39949 A2 5/2002
(Continued)

OTHER PUBLICATIONS

Xia et al., Laminar-flow immediate-overlay hepatocyte sandwich perfusion system for drug hepatotoxicity testing, Biomaterials 30 (2009) 5927-5936.*
(Continued)

Primary Examiner — Reza Ghafoorian
(74) Attorney, Agent, or Firm — Senniger Powers LLP

(57) ABSTRACT

The present invention generally relates to in vitro methods for mimicking in vivo pathological or physiologic conditions. The methods comprise applying shear forces to a cell type or cell type plated on a surface within a cell culture container. Methods for testing drugs or compounds in such systems are also described.

99 Claims, 42 Drawing Sheets

(52) U.S. Cl.
CPC ......... *G01N 33/5091* (2013.01); *C12M 35/04* (2013.01); *G01N 2800/7004* (2013.01)

(56) References Cited

U.S. PATENT DOCUMENTS

| | | | |
|---|---|---|---|
| 2003/0157709 | A1 | 8/2003 | DiMilla et al. |
| 2005/0130254 | A1 | 6/2005 | Park |
| 2006/0234207 | A1 | 10/2006 | Khaldoyanidi |
| 2007/0077265 | A1 | 4/2007 | Klueh et al. |
| 2010/0304355 | A1* | 12/2010 | Shuler et al. ............ 435/3 |

FOREIGN PATENT DOCUMENTS

| | | |
|---|---|---|
| WO | 2004/038368 A2 | 5/2004 |
| WO | 2008/066525 A2 | 6/2008 |

OTHER PUBLICATIONS

Dai et al., Distinct endothelial phenotypes evoked by arterial waveforms derived from atherosclerosis-susceptible and-resistant regions of human vasculature, Supporting Materials and methods, PNAS, Oct. 12, 2004, vol. 101, No. 41, 14871-14876.*

Chavez et al., In Vitro Models for the Study of Non-Alcoholic Fatty Liver Disease, Current Medicinal Chemistry, 2011, 18, 1079-1084.*

Zamula et al., Differentiation of Human Embryonic Stem Cells along a Hepatic Lineage, Chem Biol Interact. Mar. 15, 2011; 190(1): 62-72.*

Malik et al., The role of non-parenchymal cells in liver growth, seminars in Cell & Developmental Biology, vol. 13, 2002: pp. 425-431.*

Bader, A., et al., "3-D Coculture of Hepatic Sinusoidal Cells with Primary Hepatocytes-Design of an Organotypical Model," Experimental Cell Research, 1996, pp. 223-233, vol. 226, Article No. 0222.

Bancroft, G. N., et al., "Fluid Flow Increases Mineralized Matrix Deposition in 3D Perfusion Culture of Marrow Stromal Osteoblasts in a Dose-Dependent Manner," Proceedings of the National Academy of Sciences of the United States of America, Oct. 1, 2002, pp. 12600-12605, vol. 99, No. 22.

Definition of "Bathe," accessed at http://www.thefreedictionary.com/bathe on May 14, 2014, 4 pages.

Braet, F., et al., "Liver Sinusoidal Endothelial Cell Modulation Upon Resection and Shear Stress in vitro," Comparative Hepatology, 2004, pp. 1-11, vol. 3, No. 7.

Carraro, A., et al., "In vitro Analysis of A Hepatic Device With Intrinsic Microvascular-Based Channels," Biomedical Microdevices, 2008, pp. 795-805, vol. 10, No. 6.

Cartmell, S. H., et al., "Effects of Medium Perfusion Rate on Cell-Seeded Three-Dimensional Bone Constructs in vitro," Tissue Engineering, 2003, pp. 1197-1203, vol. 9, No. 6.

Dash, A., "Control of Flow and Oxygen in A 3-D Perfused Micro-Environment Fosters Balanced Survival of Hepatocyte-Non-Parenchymal Cell Co-Cultures," A Thesis presented to the Biological Engineering Division of the Massachusetts Institute of Technology, Jun. 2007, 146 pages.

Dash, A., et al., "Liver Tissue Engineering in the Evaluation of Drug Safety," Expert Opinion on Drug Metabolism & Toxicology, 2009, pp. 1159-1174, vol. 5, No. 10.

De Bleser, P. J., et al., "Insulinlike Growth Factor—II/Mannose 6-Phosphate Receptor is Expressed on CCI4-Exposed Rat Fat-Storing Cells and Facilitates Activation of Latent Transforming Growth Factor-beta in Cocultures with Sinusoidal Endothelial Cells," Hepatology, May 1995, pp. 1429-1437, vol. 21, No. 5.

Domansky, K., et al., "Perfused Multiwell Plate for 3D Liver Tissue Engineering," Lab on a Chip, 2010, pp. 51-58, vol. 10, No. 1.

Fukushima, S., et al., "Microscopic Velocimetry With a Scaled-Up Model for Evaluating a Flow Field Over Cultured Endothelial Cells," Journal of Biomechanical Enginering, Apr. 2002, pp. 176-179, vol. 124, No. 2.

Gomes, M. E., et al., "Effect of Flow Perfusion on the Osteogenic Differentiation of Bone Marrow Stromal Cells Cultured on Starch-Based Three-Dimensional Scaffolds," Journal of Biomedical Materials Research, Part A, Oct. 2003, pp. 87-95, vol. 67, No. 1.

Hui, E. E., et al., "Micromechanical Control of Cell-Cell Interactions," Proceedings of the National Academy of Sciences of the United States of America, 2007, pp. 5722-5726, vol. 104, No. 14.

Jung, M.-Y., et al., "Stabilin-2 is Involved in Lymphocyte Adesion to the Hepatic Sinusoidal Endothelium via the Interaction with alphaMbeta2 Integrin," Journal of Leukocyte Biology, Nov. 2007, pp. 1156-1165, vol. 82.

Khetani, S. R., et al., "Microscale Culture of Human Liver Cells for Drug Development," Nature Biotechnology, Jan. 2008, pp. 120-126, vol. 26, No. 1.

Lalor, P. F., et al., "Vascular Adhesion Protein-1 Mediates Adhesion and Transmigration of Lymphocytes on Human Hepatic Endothelial Cells," The Journal of Immunology, 2002, pp. 983-992, vol. 169.

Lee, P. J., et al., "An Artificial Liver Sinusoid With a Microfluidic Endothelial-Like Barrier for Primary Hepatocyte Culture," Biotechnology and Bioengineering, 2007, pp. 1340-1346, vol. 97, No. 5.

March, S., et al., "Microenvironmental Regulation of the Sinusoidal Endothelial Cell Phenotype in Vitro," Hepatology, Sep. 2009, pp. 920-928, vol. 50, No. 3.

Papadimitriou, M. N. B., et al., "Integrin alpha4beta/VCAM-1 Pathway Mediates Primary Adhesion of RAW117 Lymphoma Cells to Hepatic Sinusoidal Endothelial Cells Under Flow," Clincal & Experimental Metastasis, 1999, pp. 669-676, vol. 17.

Pazzano, D., et al., "Comparison of Chondrogensis in Static and Perfused Bioreactor Culture," Biotechnology Progress, Sep.-Oct. 2000, pp. 893-896, vol. 16, No. 5.

Definition of "Perfusion," accessed at http://www.medical-dictionary.thefreedictionary.com/perfusion on Feb. 25, 2014, 3 pages.

Powers, M. J., et al., "A Microfabricated Array Bioreactor for Perfused 3D Liver Culture," Biotechnology and Bioengineering, May 2002, pp. 257-269, vol. 78, No. 3.

Saito, M., et al., "Reconstruction of Liver Organoid Using a Bioreactor," World Journal of Gastroenterology, Mar. 2006, pp. 1881-1888, vol. 12, No. 12.

Saito, M., et al., "The Functional Interrelationship Between Gap Junctions and Fenestrae in Endothelial Cells of the Liver Organoid," The Journal of Membrane Biology, Jun. 2007, pp. 115-121, vol. 217, Nos. 1-3.

Tapuria, N., et al., "Effect of Remote Ischemic Preconditioning on Hepatic Microcirculation and Function in a Rat Model of Hepatic Ischemia Reperfusion Injury," HPB: The Official Journal of the Hepato Pancreato Biliary Association, Mar. 2009, pp. 108-117, vol. 11, No. 2.

Toh, Y.-C., et al, "A Novel 3D Mammalian Cell Perfusion-Culture System in Microfluidic Channels," Lab on a Chip, 2007, pp. 302-309, vol. 7, No. 3.

Wirz, W., et al., "Hepatic Stellate Cells Display a Functional Vascular Smooth Muscle Cell Phenotype in a Three-Dimensional Co-Culture Model With Endothelial Cells," Differentiation, 2008, pp. 784-794, vol. 76, No. 7.

Zhang, C., et al., "Towards a Human-on-Chip: Culturing Multiple Cell Types on a Chip With Compartmentalized Microenvironments," Lab on a Chip, 2009, pp. 3185-3192, vol. 9, No. 22.

Albini, A., et al., "A Rapid in Vitro Assay for Quantitating the Invasive Potential of Tumor Cells," Cancer Research, Jun. 15, 1987, pp. 3239-3245, vol. 47.

Ali, H., et al., Transmembrane Signaling Protocols, Second Edition, Methods in Molecular Biology, 2006, pp. 143-144 and 152-153, vol. 332.

Arnold, J. T., et al., "Endometrial Stromal Cells Regulate Epithelial Cell Growth in Vitro: A New Co-Culture Model," Human Reproduction, 2001, pp. 836-845, vol. 16, No. 5.

Blackman, B. R., et al., "A New in Vitro Model to Evaluate Differential Responses of Endothelial Cells to Simulated Arterial Shear Stress Waferoms," Journal of Biomechanical Engineering, Aug. 2002, pp. 397-407, vol. 124.

(56) References Cited

OTHER PUBLICATIONS

Blackman, B. R., et al., "In Vitro Cell Shearing Device to Investigate the Dynamic Response of Cells in a Controlled Hydrodynamic Environment," Annals of Biomedical Engineering, Apr. 2000, pp. 363-372, vol. 28, No. 4.
Boyden, S., "The Chemotactic Effect of Mixtures of Antibody and Antigen on Polymorphonuclear Leucocytes," The Journal of Experimental Medicine, Mar. 1, 1962, pp. 453-466, vol. 115.
Bronneberg, D., et al., "MMP-2 and MMP-9 Regulation of a Vascular Coculture System under Shear Stress," Eindhoven University of Technology, Apr. 2003, pp. 1-34, Downloaded from <http://www.mate.tue.nl/mate/pdfs/2893.pdf>.
Brooks, A. R., et al., "Gene Expression Profiling of Vascular Endothelial Cells Exposed to Fluid Mechanical Forces: Relevance for Focal Susceptibility to Atherosclerosis," Endothelium, 2004, pp. 45-57, vol. 11.
Cattaruzza, M., et al., "Shear Stress Insensitivity of Endothelial Nitric Oxide Synthase Expression as a Genetic Risk Factor for Coronary Heart Disease," Circulation Research, 2004, pp. 841-847, vol. 95.
Chiu, J.-J., et al., "A Model for Studying the Effect of Shear Stress on Interactions Between Vascular Endothelial Cells and Smooth Muscle Cells," Journal of Biomechanics, Apr. 2004, pp. 531-539, vol. 37, No. 4.
Chiu, J.-J., et al., "Shear Stress Inhibits Adhesion Molecule Expression in Vascular Endothelial Cells Induced by Coculture with Smooth Muscle Cells," Blood, Apr. 2003, pp. 2667-2674, vol. 101, No. 7.
Corning Incorporated, "Transwell(R) Permeable Supports Selection and Use Guide," Life Sciences, 2006, pp. 1-11.
Cunningham, K. S., et al., "The Role of Shear Stress in the Pathogenesis of Atherosclerosis," Laboratory Investigation, 2005, pp. 9-23, vol. 85.
Dai, G., et al., "Distinct Endothelial Phenotypes Evoked by Arterial Waveforms Derived from Atherosclerosis-Susceptible and -Resistant Regions of Human Vasculature," Proceedings of the National Academy of Sciences of the United States of America, Oct. 12, 2004, pp. 14871-14876, vol. 101, No. 41.
Dardik, A., et al., "Shear Stress-Stimulated Endothelial Cells Induce Smooth Muscle Cell Chemotaxis Via Platelet-Derived Growth Factor-BB and Interleukin-1alpha," Journal of Vascular Surgery, Feb. 2005, pp. 321-331, vol. 41, No. 2.
Dash, A., et al., "Physiological Hemodynamic Flow and Transport are Necessary for Retention of Primary Hepatocyte Drug Metabolism and Toxicity Indices," Abstract #504, The Toxicologist, Supplement to Toxicological Sciences, 51st Annual Meeting and ToxExpo, Mar. 11-15, 2012, p. 109, vol. 126, Issue 1.
Demeuse, P., et al., "Compartmentalized Coculture of Rat Brain Endothelial Cells and Astrocytes: A Syngenic Model to Study the Blood-Brain Barrier," Journal of Neuroscience Methods, Nov. 15, 2002, pp. 21-31, vol. 121, No. 1.
Depaolo, N., et al., "Electrical Impedance of Cultured Endothelium Under Fluid Flow," Annals of Biomedical Engineering, 2001, pp. 648-656, vol. 29.
Garcia-Cardena, G., et al., "Biomechanical Activation of Vascular Endothelium as A Determinant of its Functional Phenotype," Proceedings of the National Academy of Sciences of the United States of America, Apr. 10, 2001, pp. 4478-4485, vol. 98, No. 8.
Gerthoffer, W. T., et al., "Secretory Functions of Smooth Muscle: Cytokines and Growth Factors," Molecular Interventions, Nov. 2002, pp. 447-456, vol. 2, No. 7.
Giaever, I., et al., "Monitoring Fibroblast Behavior in Tissue Culture with an Applied Electric Field," Proceedings of the National Academy of Sciences of the United States of America, Jun. 1984, pp. 3761-3764, vol. 81, No. 12.
Grierson, J. P., et al., "Shear Stress-Induced [Ca2+]i Transients and Oscillations in Mouse Fibroblasts are Mediated by Endogenously Released ATP," The Journal of Biological Chemistry, Mar. 3, 1995, pp. 4451-4456, vol. 270, No. 9.

Harris, S. G., al. "Development of a Physiologically Based in Vitro Model of the Blood-Brain Barrier," Bioengineering Conference, Proceedings of the IEEE 28th, 2002, pp. 1-2.
Hastings, N. E., "Atherosclerosis-Prone Hemodynamics Differentially Regulates Endothelial and Smooth Muscle Cell Phenotypes and Promotes Pro-Inflammatory Priming," American Journal of Physiology, Cell Physiology, 2007, pp. C1824-C1833, vol. 293, No. 6.
Iadecola, C., "Neurovascular Regulation in the Normal Brain and in Alzheimer's Disease," Nature Reviews, Neuroscience, May 2004, pp. 347-360, vol. 5, No. 5.
Ji, J. Y., et al., "Shear Stress Causes Nuclear Localization of Endothelial Glucocorticoid Receptor and Expression from the GRE Promoter," Circulation Research, Journal of the American Heart Association, Feb. 21, 2003, pp. 279-285, vol. 92, No. 3.
Laurens, N., et al., "Isolation, Purification and Culture of Human Micro- and Macrovascular Endothelial Cells," Chapter 1, Springer Lab Manual, Methods in Endothelial Cell Biology, 2004, pp. 3-8.
Lee, J. S. H., et al., "Cdc42 Mediates Nucleus Movement and MTOC Polarization in Swiss 3T3 Fibroblasts Under Mechanical Shear Stress," Molecular Biology of the Cell, Feb. 2005, pp. 871-880, vol. 16, No. 2.
Ma, S. H., et al., "An Endothelial and Astrocyte Co-Culture Model of the Blood-Brain Barrier Utilizing an Ultra-Thin, Nanofabricated Silicon Nitride Membrane," Lab on a Chip, Jan. 2005, pp. 74-85, vol. 5, No. 1.
Malek, A. M., et al., "A Cone-Plate Apparatus for the in Vitro Biochemical and Molecular Analysis of the Effect of Shear Stress on Adherent Cells," Methods in Cell Science, 1995, pp. 165-176, vol. 17.
Marx, U., et al., Breakthroughs and Trends in Cell Culture Technology, Drug Testing in Vitro, 2007, pp. 34-36.
Millipore Corporation, "Millicell Technical Guide," A Publication of Technical Services, Literature No. TN2004EN00, Apr. 2004, pp. 1-25.
Navab, M., et al., "Monocyte Migration into the Subendothelial Space of a Coculture of Adult Human Aortic Endothelial and Smooth Muscle Cells," Journal of Clinical Investigation, Dec. 1988, pp. 1853-1863, vol. 82.
Orr, A. W., et al., "Mechanisms of Mechanotransduction," Developmental Cell, Jan. 2006, pp. 11-20, vol. 10, No. 1.
Price, D. T., et al., "Design Rule for Optimization of Microelectrodes Used in Electric Cell-Subtrate Impedance Sensing (ECIS)," Biosensors and Bioelectronics, 2009, pp. 2071-2076, vol. 24, No. 7.
Rainger, G. E., et al., "A Novel System for Investigating the Ability of Smooth Muscle Cells and Fibroblasts to Regulate Adhesion of Flowing Leukocytes to Endothelial Cells," Journal of Immunological Methods, Sep. 1, 2001, pp. 73-82, vol. 255, No. 1-2.
Saidi, H., et al., "IFN-Gamma-Activated Monocytes Weakly Produce HIV-1 but Induce the Recruitment of HIV-Sensitive T Cells and Enhance the Viral Production by These Recruited T Cells," Journal of Leukocyte Biology, Mar. 2007, pp. 642-653, vol. 81, No. 3.
Schwachtgen, J.-L., et al., "Fluid Shear Stress Activation of egr-1 Transcription in Cultured Human Endothelial and Epithelial Cells is Mediated Via the Extracellular signal-Related Kinase 1/2 Mitogen-Activated Protein Kinase Pathway," The Journal of Clinical Investigation, Jun. 1, 1998, pp. 2540-2549, vol. 101, No. 11.
Seebach, J., et al., "Endothelial Barrier Function Under Laminar Fluid Shear Stress," Laboratory Investigation, 2000, p. 1819, vol. 80, No. 12.
Shyy, Y.-J., et al., "Fluid Shear Stress Induces a Biphasic Response of Human Monocyte Chemotactic Protein I Gene Expression in Vascular Endothelium," Proceedings of the National Academy of Sciences of the United States of America, May 24, 1994, pp. 4678-4682, vol. 91, No. 11.
Starmans-Kool, et al., "Measurement of Hemodynamics in Human Carotid Artery Using Ultrasound and Computational Fluid Dynamics," Journal of Applied Physiology, Mar. 2002, pp. 957-961, vol. 92.
Wamhoff, B. R., et al., "Hemodynamic Flow and Heterotypic Cell Communication are Necessary for Predicting Human Vascular Drug

(56) References Cited

OTHER PUBLICATIONS

Response in Preclinical Vascular in Vitro Systems," Abstract #1169, The Toxicologist, Supplement to Toxicological Sciences, 51st Annual Meeting and ToxExpo, Mar. 11-15, 2012, p. 251, vol. 126, Issue 1.
Wang, H. Q., et al., "Shear Stress Protects Against Endothelial Regulation of Vascular Smooth Muscle Cell Migration in a Coculture System," Endothelium, May-Jun. 2006, pp. 171-180, vol. 13, No. 3.
Wilczek, K., et al., "Comparison of Self-Expanding Polyethylene Terephthalate and Metallic Stents Implanted in Porcine Iliac Arteries," CardioVascular and Interventional Radiology, 1996, pp. 176-180, vol. 19.
Yamamoto, K., et al., "Fluid Shear Stress Induces Differentiation of Flk-1-Positive Embryonic Stem Cells Into Vascular Endothelial Cells in vitro," American Journal of Physiology, Heart and Circulatory Physiology, Apr. 2005, pp. H1915-H1924, vol. 288, No. 4.
Novik, E., et al., "A Microfluidic Hepatic Coculture Platform for Cell-Based Drug Metabolism Studies," Biochemical Pharmacology, Apr. 1, 2010, pp. 1036-1044, vol. 79, No. 7.
Preliminary Amendment A and Response to Notification to Comply with Requirements for Patent Applications Containing Nucleotide and/or Amino Acid Sequence Disclosures, filed Aug. 25, 2015 for U.S. Appl. No. 14/395,119, 10 pages.
Restriction Requirement issued on Nov. 16, 2015 for U.S. Appl. No. 14/395,119, 10 pages.
Corrected Notice of Allowability issued for U.S. Appl. No. 14/395,119, dated Jun. 8, 2016, 4 pages.
El Amine, M., et al., "Plasma Levels of ICAM-1 and Circulating Endothelial Cells are Elevated in Unstable Types 1 and 2 Diabetes," Endocrine Regulations, Jan. 2010, pp. 17-24, vol. 44, No. 1 (Abstract only).
Engelberg, H., "Plasma Heparin Levels in Normal Man," Circulation, Apr. 1961, pp. 578-581, vol. 23.
Fadel, F. I., et al., "Some Amino Acids Levels: Glutamine, Glutamate, and Homocysteine, in Plasma of Children with Chronic Kidney Disease," International Journal of Biomedical Science, Mar. 2014, pp. 36-42, vol. 10, No. 1.
Hiscock, N., et al., "Exercise-induced Immunodepression-plasma Glutamine is Not the Link," Journal of Applied Physiology, Sep. 2002, pp. 813-822, vol. 93, No. 3.
Katayama, M., et al., "Soluble P-selectin is Present in Normal Circulation and Its Plasma Level is Elevated in Patients with Thrombotic Thrombocytopenic Purpura and Haemolytic Uraemic Syndrome," British Journal of Haematology, Aug. 1993, pp. 702-710, vol. 84, No. 4 (Abstract only).
Notice of Allowance issued for U.S. Appl. No. 14/395,119, dated May 26, 2016, 43 pages.
Zannettino, A. C. W., et al., "Elevated Serum Levels of Stromal-Derived Factor-1alpha Are Associated with Increased Osteoclast Activity and Osteolytic Bone Disease in Multiple Myeloma Patients," Cancer Research, Mar. 1, 2005, pp. 1700-1709, vol. 65, No. 5.
Brooks, A. R., et al., "Gene Expression Profiling of Vascular Endothelial Cells Exposed to Fluid Mechanical Forces: Relevance for Focal Susceptibility to Atherosclerosis," Endothelium, Jan.-Feb. 2004, pp. 45-57, vol. 11, No. 1.
Hoff, P. M., et al., "Phase I Study with Pharmacokinetics of S-1 on an Oral Daily Schedule for 28 Days in Patients with Solid Tumors," Clinical Cancer Research, Jan. 2003, pp. 134-142, vol. 9.
Lee, J. K., et al., "Sulindac and Its Metabolites Inhibit Multiple Transport Proteins in Rat and Human Hepatocytes," The Journal of Pharmacology and Experimental Therapeutics, 2010, pp. 410-418, vol. 334, No. 2.

* cited by examiner

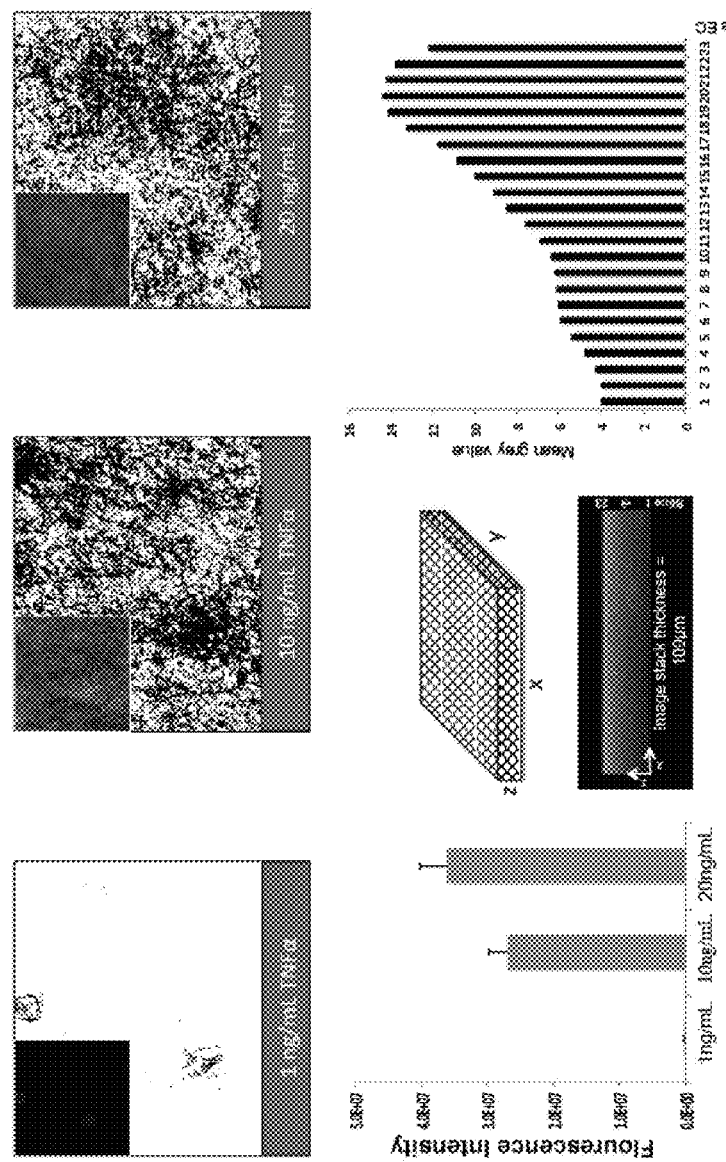
Fig. 1A
Fig. 1B

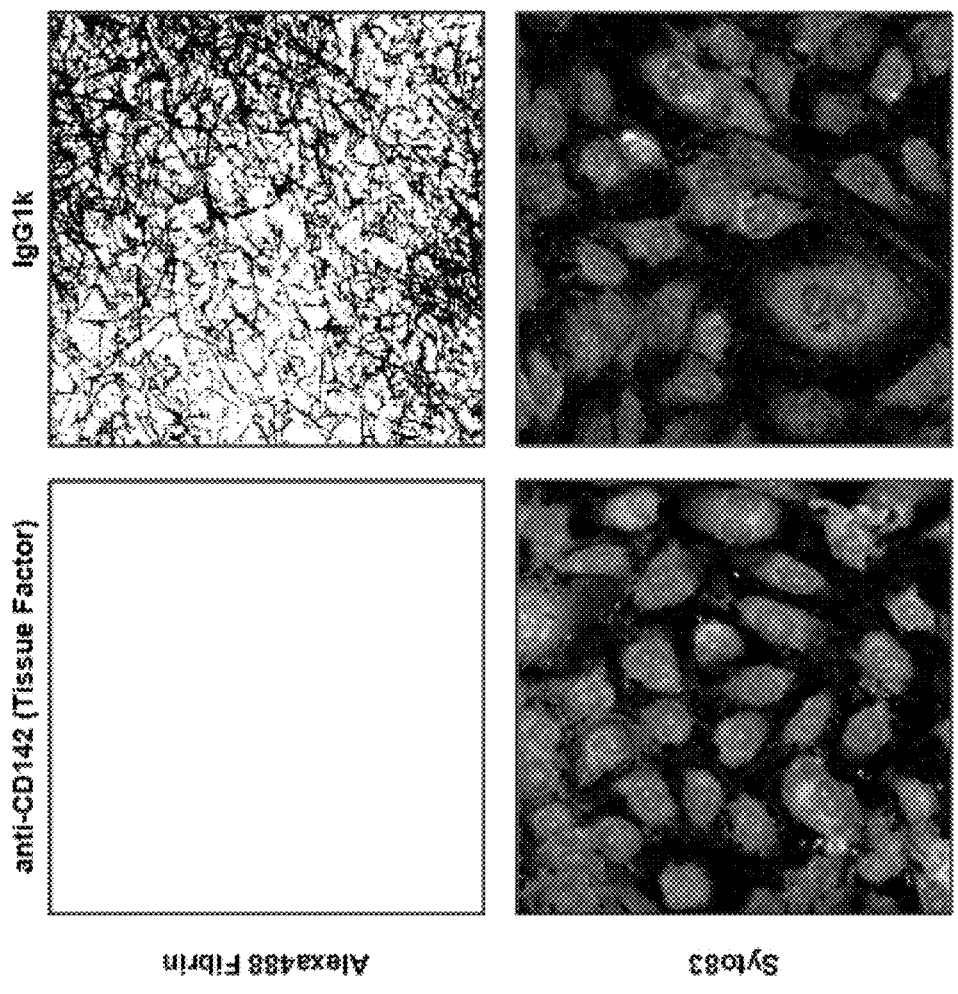

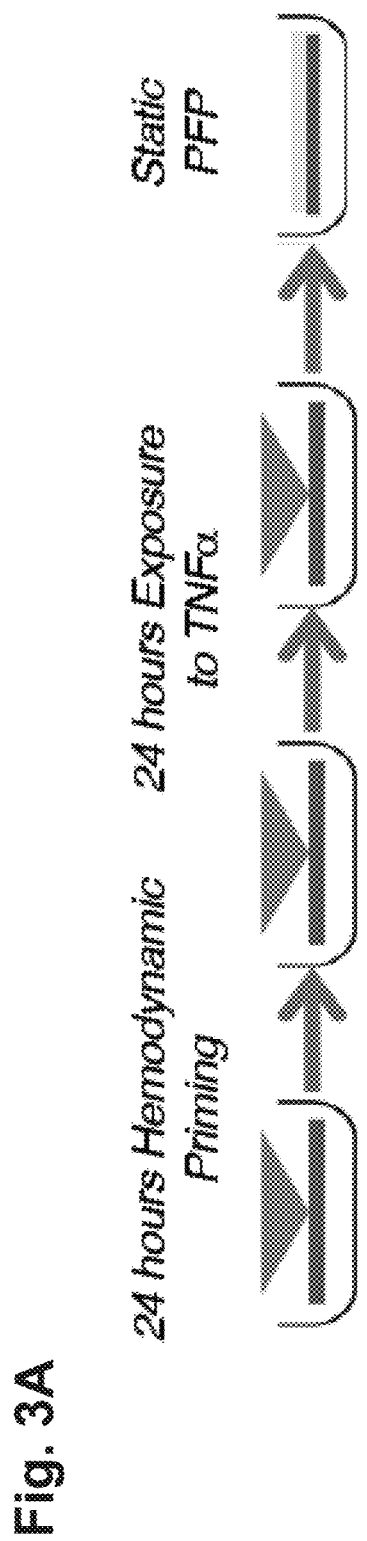

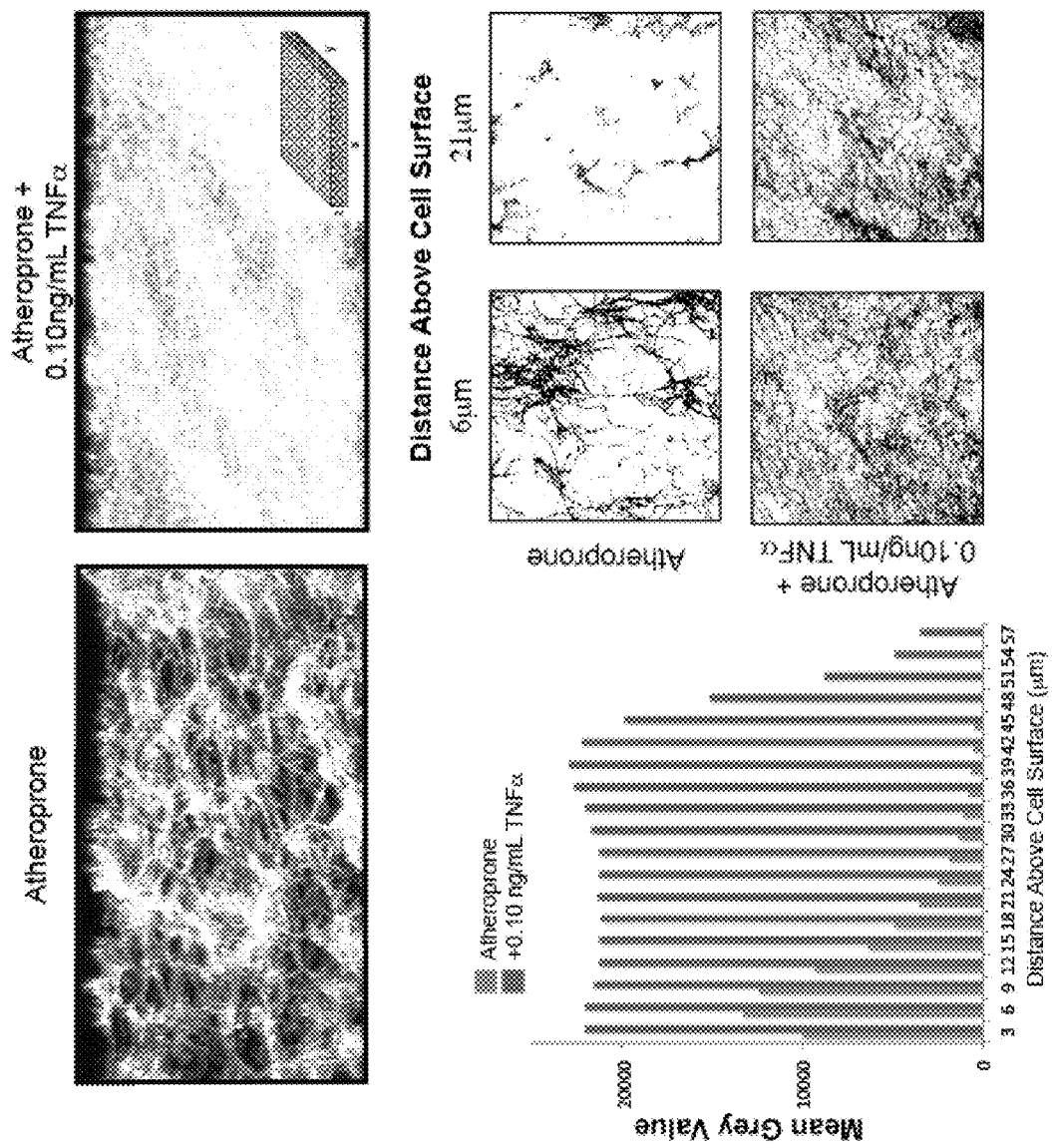

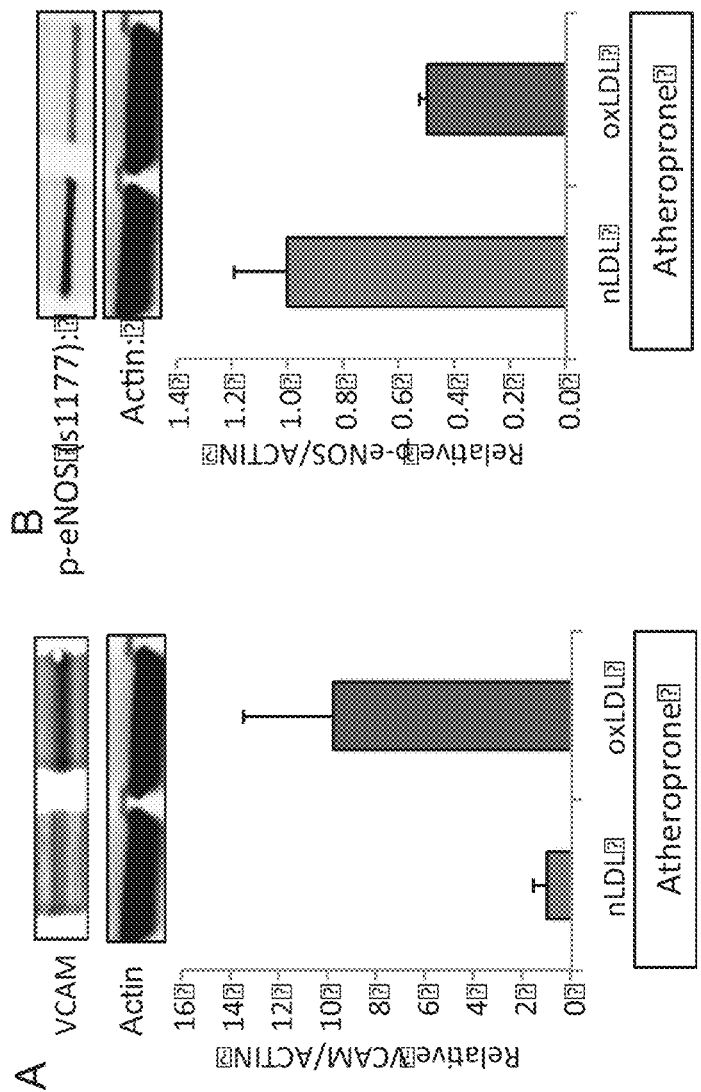
Fig. 7A-B

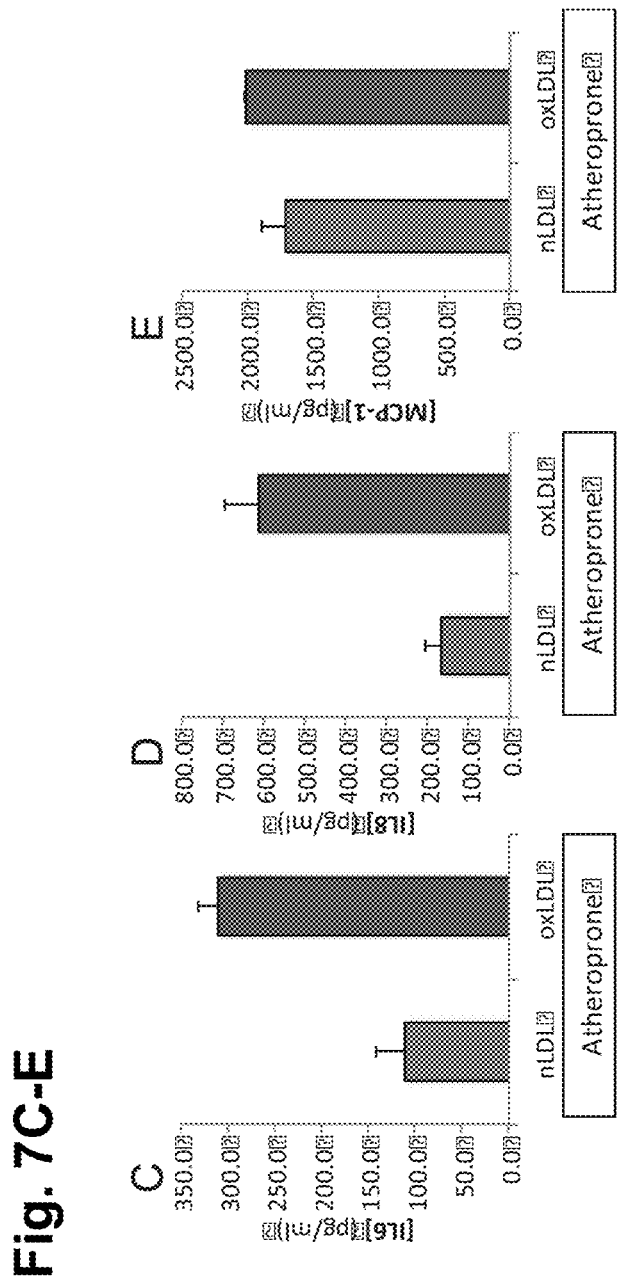
Fig. 7C-E

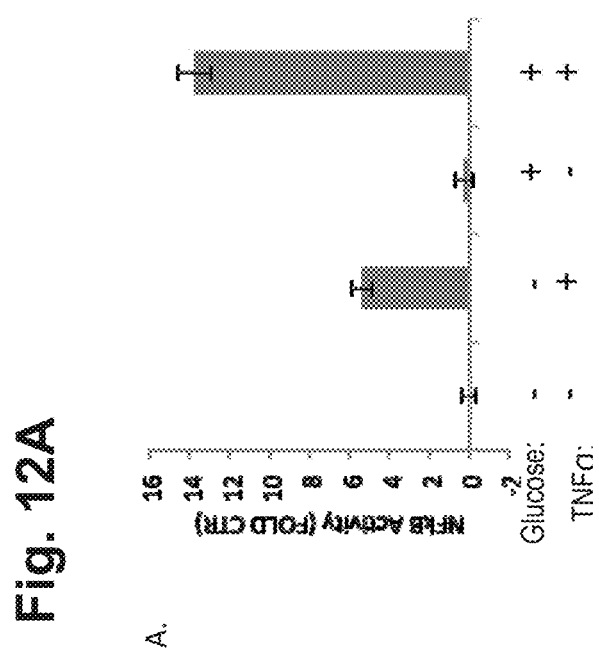

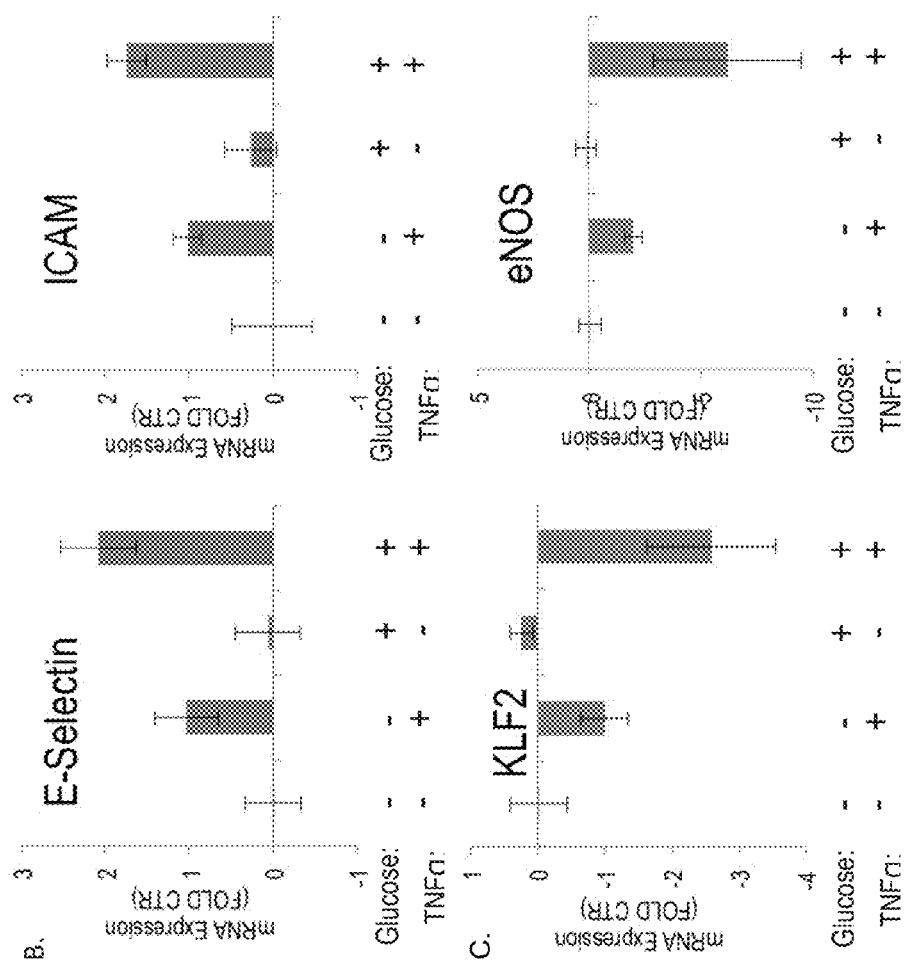
Fig. 12B-C

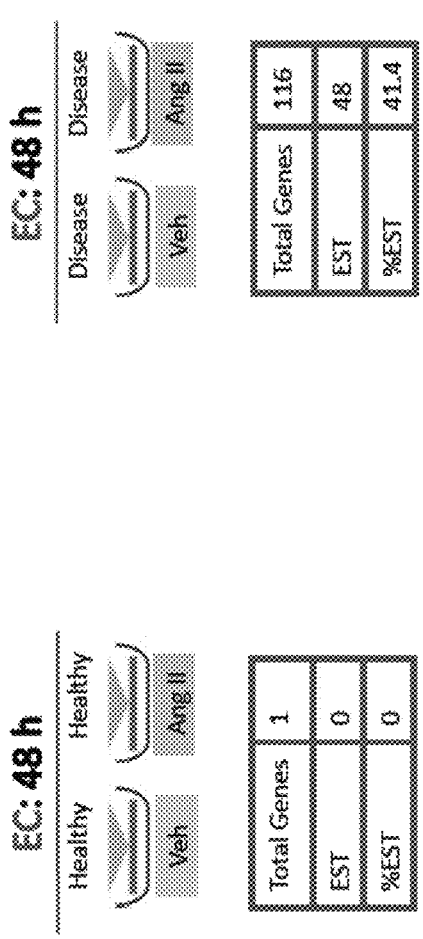
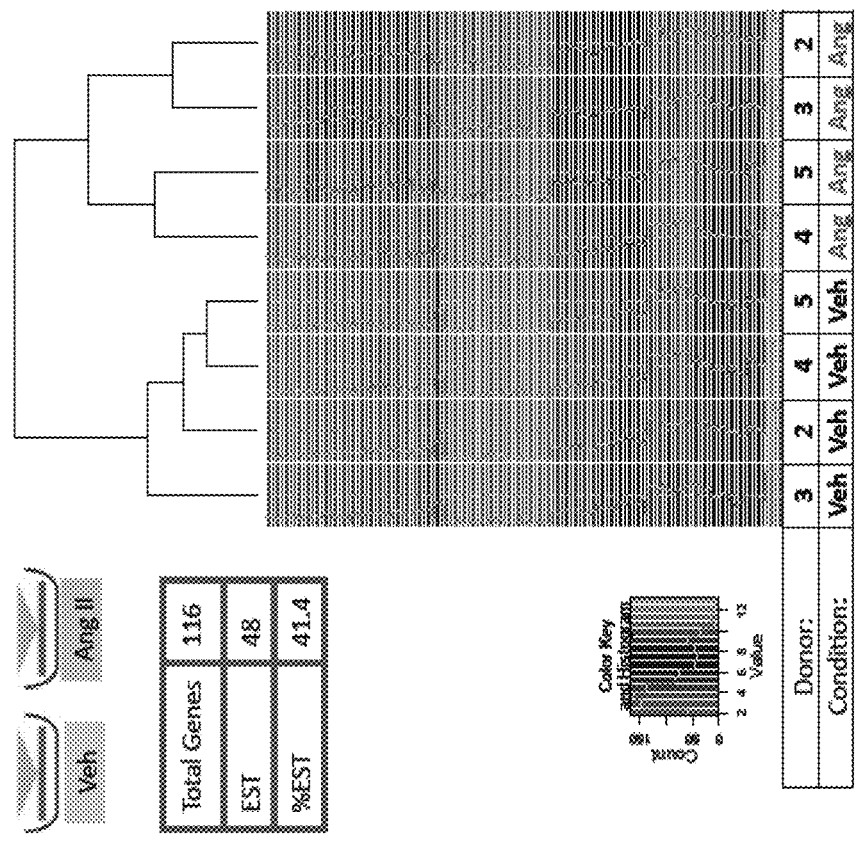
Fig. 13A

Fig. 25
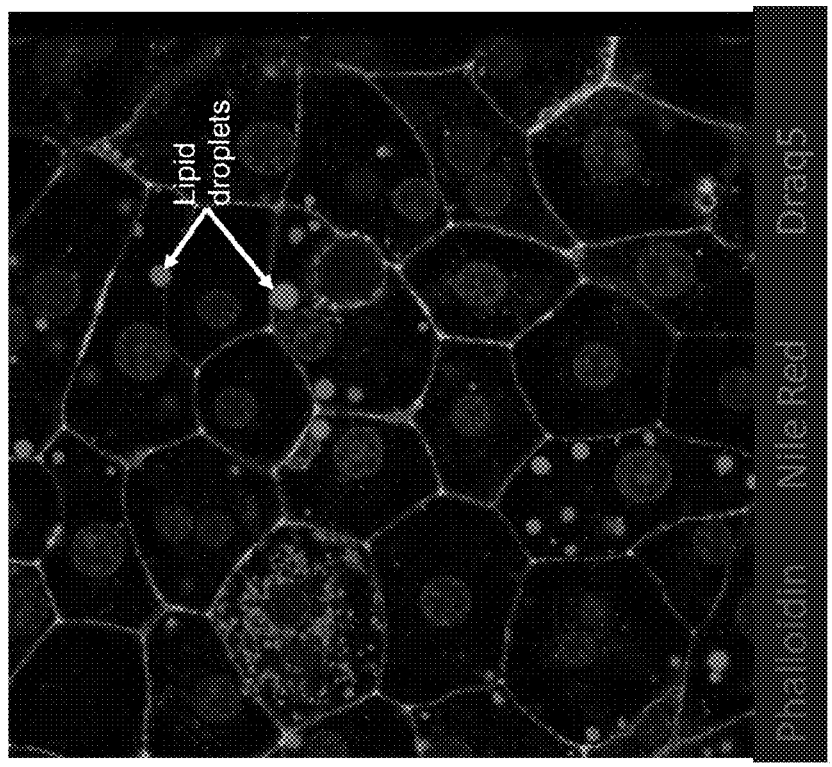
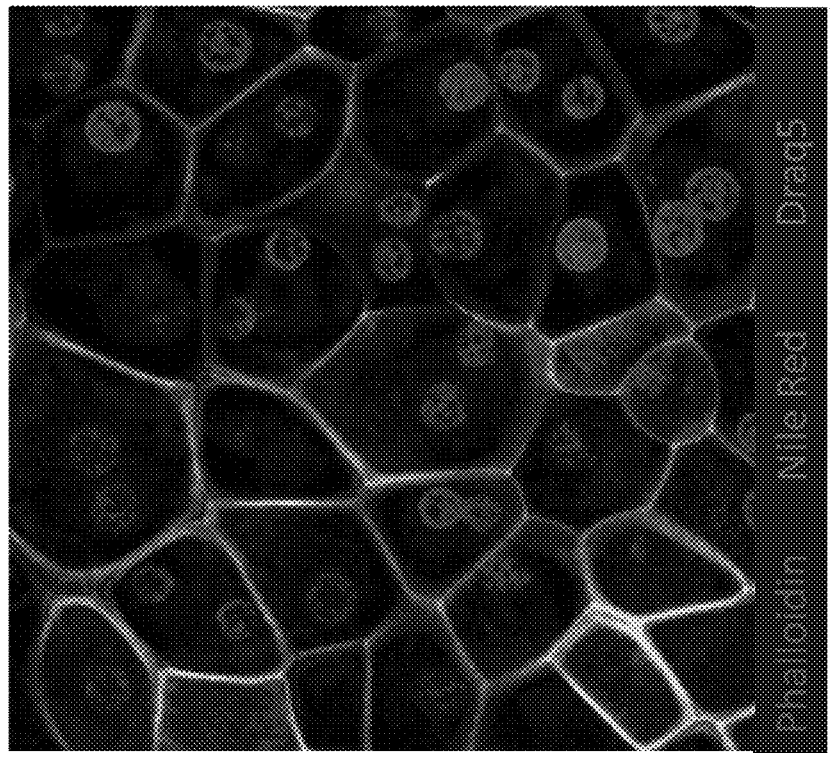

Fig. 27
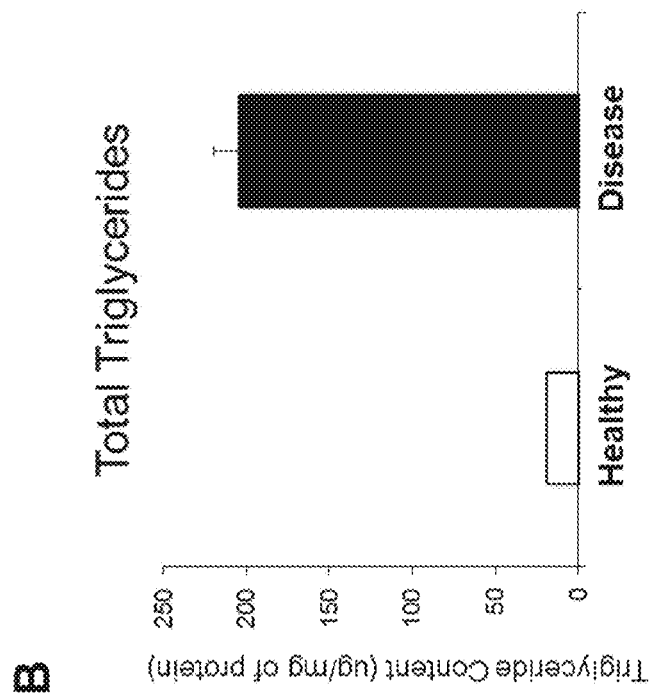
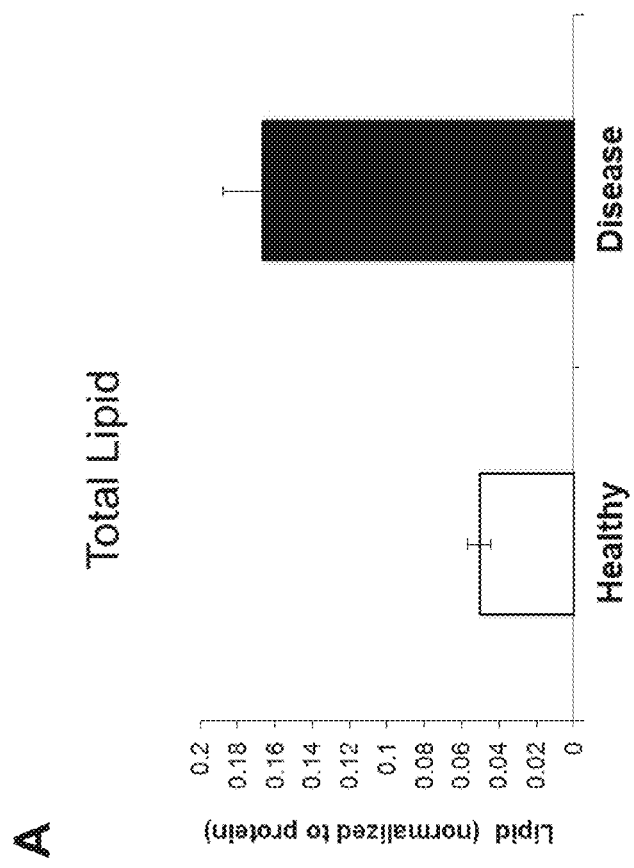

IN VITRO MODEL FOR PATHOLOGICAL OR PHYSIOLOGIC CONDITIONS

FIELD OF THE INVENTION

The present invention generally relates to in vitro methods for mimicking in vivo pathological or physiologic conditions. The present invention also relates to methods for testing drugs or compounds in such systems.

BACKGROUND OF THE INVENTION

Conventional in vitro models of pathological or physiological conditions generally involve culturing one or more cell types under static conditions. However, such models typically require the addition of one or more factors in concentrations much higher than those observed in vivo in the pathological or physiological condition. For example, in order to maintain hepatocytes in static tissue culture, insulin and glucose must be added to the culture media in concentrations significantly higher than the concentrations observed in vivo in healthy individuals (by approximately 2 to 4-fold for glucose, and about 10,000-fold to 40,000-fold for insulin). Similarly, in conventional static monocultures of endothelial cells used to model thrombosis, significantly elevated levels of TNFα as compared to those observed in human circulating blood are required to induce fibrin deposition.

Furthermore, the conventional systems often do not exhibit responses to drugs or compounds at concentrations that induce the response in vivo, instead requiring much higher concentrations of the drug or compound to induce the same response.

SUMMARY OF THE INVENTION

One aspect of the present invention is directed to a method of mimicking a pathological condition in vitro. The method comprises adding a culture media to a cell culture container, adding at least one factor to the culture media, plating at least one cell type on at least one surface within the cell culture container, and applying a shear force upon the at least one plated cell type. The shear force results from flow of the culture media induced by a flow device. The flow mimics flow to which the at least one cell type is exposed in vivo in the pathological condition. The concentration of the factor in the culture media can be within the in vivo concentration range of the factor observed in the pathological condition. Alternatively, the concentration of the factor in the culture media can be within the concentration range of the factor that would result in vivo from administration of a drug or a compound.

Another aspect of the present invention is an in vitro method of testing a drug or a compound for an effect on a pathological condition. The method comprises mimicking the pathological condition, adding a drug or a compound to the culture media, and applying the shear force upon the at least one plated cell type exposed to the drug or the compound. A change in the at least one plated cell type, in the presence of the drug or the compound, indicates that the drug or the compound has an effect on the pathological condition. In this in vitro method of testing a drug or compound, the pathological condition can be mimicked by the in vitro method of mimicking a pathological condition as described above.

The present invention also provides an in vitro method of testing a drug or compound for an effect. The method comprises adding a culture media to a cell culture container, plating at least one cell type on at least one surface within the cell culture container, adding a drug or a compound to the culture media, and applying a shear force upon the at least one plated cell type exposed to the drug or the compound. The concentration of the drug or the compound in the culture media is within the concentration range of the drug or the compound that achieves the effect in vivo. The shear force results from flow of the culture media induced by a flow device. The flow mimics flow to which the at least one cell type is exposed in vivo. A change in the at least one plated cell type, in the presence of the drug or the compound, indicates that the drug or the compound has the effect. The effect can be, for example, an effect on a physiologic condition or an effect on a pathological condition.

Another aspect of the present invention is a method of mimicking a physiologic condition in vitro. The method comprises adding a culture media to a cell culture container, adding at least one factor to the culture media, plating at least one cell type on at least one surface within the cell culture container, and applying a shear force upon the at least one plated cell type. The shear force results from flow of the culture media induced by a flow device. The flow mimics flow to which the at least one cell type is exposed in vivo in the physiologic condition. The concentration of the factor in the culture media can be within the in vivo concentration range of the factor observed in the physiologic condition. Alternatively, the concentration of the factor in the culture media can be within the concentration range of the factor that would result in vivo from administration of a drug or a compound.

The present invention is also directed to an in vitro method of testing a drug or a compound for an effect on a physiologic condition. The method comprises mimicking the physiologic condition, adding a drug or a compound to the culture media, and applying the shear force upon the at least one plated cell type exposed to the drug or the compound. A change in the at least one plated cell type, in the presence of the drug or the compound, indicates that the drug or the compound has an effect on the physiologic condition. In this in vitro method of testing a drug or compound, the physiologic condition can be mimicked by the in vitro method of mimicking a physiologic condition as described above.

Another aspect of the invention is a method of mimicking a pathological or physiologic condition of the liver in vitro. The method comprises adding a culture media to a cell culture container, adding at least one factor to the culture media, plating at least one hepatic cell type on at least one surface within the cell culture container, and applying a shear force upon the at least one plated hepatic cell type. The shear force results from flow of the culture media induced by a flow device. The flow mimics flow to which the at least one hepatic cell type is exposed in vivo in the pathological or physiologic condition. The concentration of the factor in the culture media for mimicking the pathological condition can be within the in vivo concentration range of the factor observed in the pathological condition. Alternatively, the concentration of the factor in the culture media can be within the concentration range of the factor that would result in vivo from administration of a drug or a compound. As a further alternative, the concentration of the factor in the culture media can be capable of maintaining the mimicked pathological condition in vitro for a period of time under the shear force, the same concentration of factor being incapable of maintaining the mimicked pathological condition in vitro for the period of time in the absence of the shear force. The concentration of the factor in the culture media for mimicking the physiologic condition can be within the in vivo concentration range of the factor observed in the physiologic condition. Alternatively, the concentration of the factor in the culture media can be within the concentration range of the factor that would result in vivo from administration of a drug or a compound. As a further alternative, the concentration of the factor in the culture media can be capable of maintaining the mimicked physiologic condition in vitro for a period of time under the shear force, the same concentration of factor being incapable of maintaining the mimicked physiologic condition in vitro for the period of time in the absence of the shear force.

The present invention also provides an in vitro method of testing a drug or a compound for an effect on a pathological or physiological condition. The method comprises mimicking the pathological or physiological condition, adding a drug or a compound to the culture media, and applying the shear force upon at least one plated hepatic cell type exposed to the drug or the compound. A change in the at least one plated hepatic cell type, in the presence of the drug or the compound, indicates that the drug or the compound has an effect on the pathological or physiological condition. In this in vitro method of testing a drug or compound, the pathological condition can be mimicked by the in vitro method of mimicking a pathological or physiological condition as described in the immediately preceding paragraph.

Another aspect of the invention is directed to a method of mimicking a pathological or physiologic condition of the liver in vitro. The method comprises adding a culture media to a cell culture container, depositing at least one extracellular matrix component on a surface within the cell culture container, plating hepatocytes on the at least one extracellular matrix component, and indirectly applying a shear force upon the at least one extracellular matrix component and the hepatocytes. The shear force results from flow of the culture media induced by a flow device. The flow mimics flow to which the hepatocytes are exposed in vivo in the pathological or physiologic condition.

The invention also provides another method of mimicking a pathological or physiologic condition of the liver in vitro. The method comprises adding a culture media to a cell culture container and plating hepatocytes on a first surface of a porous membrane. The porous membrane is suspended in the cell culture container such that the first surface is proximal and in spaced relation to a bottom surface of the container, thereby defining within the container a lower volume comprising the hepatocytes and an upper volume comprising a second surface of the porous membrane. A shear force is applied upon the second surface of the porous membrane in the upper volume of the container, the shear force resulting from flow of the culture media induced by a flow device. The flow mimics flow to which the hepatocytes are exposed in vivo in the pathological or physiologic condition. The flow device comprises a body adapted for being positioned in the culture media in the upper volume of the container and a motor adapted to rotate the body.

BRIEF DESCRIPTION OF THE DRAWINGS

FIG. 1A depicts an exemplary protocol for a thrombosis assay performed under static culture conditions.

FIGS. 1B and 1C show exemplary fluorescent microscopy results from a thrombosis assay performed under static culture conditions.

FIG. 3A shows an exemplary protocol for a thrombosis assay performed under hemodynamic culture conditions.

FIG. 4B depicts exemplary fluorescent microscopy results from a thrombosis assay performed under hemodynamic culture conditions, with continued application of shear stress during clot formation.

FIGS. 7A-E illustrate changes in gene expression in response to oxLDL.

FIGS. 12A-C depict exemplary data showing NFκB activity and changes expression of genes involved in inflammatory signaling in response to treatment with glucose and TNFα.

FIGS. 13A-B show exemplary gene array data for endothelial cells and smooth muscle cells treated with angiotensin II under hemodynamic conditions.

FIGS. 25A-B show exemplary fluorescent microscopy images of hepatocytes cultured under healthy conditions or conditions that mimic fatty liver disease.

FIGS. 27A-B show exemplary results from assays measuring total lipids and total triglycerides in hepatocytes cultured under healthy conditions or conditions that mimic fatty liver disease.

FIGS. 30A-3C show exemplary fluorescent microscopy images from hepatocytes cultured under healthy conditions or under conditions that mimic fatty liver disease, in the presence or absence of pioglitazone.

Corresponding reference characters indicate corresponding parts throughout the drawings.

DESCRIPTION OF THE PREFERRED EMBODIMENTS

Figure 2A:
FIG. 2A illustrates an exemplary protocol for application of atheroprone or atheroprotective hemodynamic flow to co-cultures of endothelial cells and smooth muscle cells.

The present invention provides in vitro methods for mimicking an in vivo pathological or physiologic condition. Unlike static models currently used as the standard in vitro models by the pharmaceutical and biopharmaceutical industries, the methods of the invention apply shear forces to cultured cells and replicate an in vivo pathological or physiological condition using in vivo pathological or physiologic concentrations of various factors. For example, an in vitro liver model has been discovered in which hepatocytes can be maintained at in vivo physiologic concentrations of insulin and glucose that are significantly decreased as compared to the concentrations used in the standard static model. It has further been discovered that when higher concentrations of insulin and glucose are used in such a model, the hepatocytes exhibit numerous hallmarks of fatty liver disease.

The present invention is also directed to a method of mimicking a pathological condition in vitro. The method comprises adding a culture media to a cell culture container, adding at least one factor to the culture media, plating at least one cell type on at least one surface within the cell culture container, and applying a shear force upon the at least one plated cell type. The shear force results from flow of the culture media induced by a flow device. The flow mimics flow to which the at least one cell type is exposed in vivo in the pathological condition.

The concentration of the factor in the culture media can be within the in vivo concentration range of the factor observed in the pathological condition. Alternatively, the concentration of the factor in the culture media can be within the concentration range of the factor that would result in vivo from administration of a drug or a compound.

To confirm that the in vivo pathological condition is mimicked, a change in a level of a marker of the pathological condition can be compared between the method of the invention and the same method in the absence of application of the shear force. The level of the marker in the at least one plated cell type or in the culture media upon application of the shear force is compared to the level of the marker in the at least one plated cell type or in the culture media in the absence of application of the shear force. For example, if a marker is known to be associated with a pathological condition and its concentration is known to increase in the serum when the condition is present in vivo, an increase in the level of the marker in the culture media of the method of the invention with application of the shear force as compared to the level of the marker in the culture media in the absence of application of the shear force confirms that the in vivo pathological condition is mimicked by the in vitro method of the invention.

Pathological conditions, effects on the pathological conditions, physiologic conditions, flow devices, hemodynamic patterns, cell types, and cell culture media including factors added to the cell culture media for use in the methods of the invention are described in detail below, following the description of the various methods of the invention.

The present invention is also directed to an in vitro method of testing a drug or a compound for an effect on a pathological condition. The method comprises mimicking the pathological condition, adding a drug or a compound to the culture media, and applying the shear force upon the at least one plated cell type exposed to the drug or the compound. A change in the at least one plated cell type, in the presence of the drug or the compound, indicates that the drug or the compound has an effect on the pathological condition.

In this in vitro method of testing a drug or compound, the pathological condition can be mimicked by the in vitro method of mimicking a pathological condition as described above.

The pathological condition of the in vitro method of testing a drug or compound can also be mimicked by plating primary cells or immortalized cells from a subject or subjects having the pathological condition, and culturing the cells in cell culture media.

The present invention is also directed to a method of mimicking a physiologic condition in vitro. The method comprises adding a culture media to a cell culture container, adding at least one factor to the culture media, plating at least one cell type on at least one surface within the cell culture container, and applying a shear force upon the at least one plated cell type. The shear force results from flow of the culture media induced by a flow device. The flow mimics flow to which the at least one cell type is exposed in vivo in the physiologic condition.

The concentration of the factor in the culture media can be within the in vivo concentration range of the factor observed in the physiologic condition. Alternatively, the concentration of the factor in the culture media can be within the concentration range of the factor that would result in vivo from administration of a drug or a compound.

To confirm that the in vivo physiologic condition is mimicked, a change in a level of a marker of the physiologic condition can be compared between the method of the invention and the same method in the absence of application of the shear force. The level of the marker in the at least one plated cell type or in the culture media upon application of the shear force is compared to the level of the marker in the at least one plated cell type or in the culture media in the absence of application of the shear force. For example, if a marker is known to be associated with a physiologic condition and its concentration is known to increase in the serum when the condition is present in vivo, an increase in the level of the marker in the culture media of the method of the invention with application of the shear force as compared to the level of the marker in the culture media in the absence of application of the shear force confirms that the in vivo physiologic condition is mimicked by the in vitro method of the invention.

The present invention is also directed to an in vitro method of testing a drug or a compound for an effect on a physiologic condition. The method comprises mimicking the physiologic condition, adding a drug or a compound to the culture media, and applying the shear force upon the at least one plated cell type exposed to the drug or the compound. A change in the at least one plated cell type, in the presence of the drug or the compound, indicates that the drug or the compound has an effect on the physiologic condition.

In this in vitro method of testing a drug or compound, the physiologic condition can be mimicked by the in vitro method of mimicking a physiologic condition as described above.

The physiologic condition of this in vitro method of testing a drug or compound can also be mimicked by plating primary cells or immortalized cells, and culturing the cells in cell culture media. The primary or immortalized cells are described in detail below.

The present invention also relates to an in vitro method of testing a drug or a compound for an effect. The method comprises adding a culture media to a cell culture container, plating at least one cell type on at least one surface within the cell culture container, adding a drug or a compound to the culture media, and applying a shear force upon the at least one plated cell type exposed to the drug or the compound. The concentration of the drug or the compound in the culture media is within the concentration range of the drug or the compound that achieves the effect in vivo. The shear force results from flow of the culture media induced by a flow device. The flow mimics flow to which the at least one cell type is exposed in vivo. A change in the at least one plated cell type, in the presence of the drug or the compound, indicates that the drug or the compound has the effect.

The effect can be an effect on a pathological condition. Alternatively, the effect can be an effect on a physiologic condition. Further effects are described in detail below.

In any of the methods of the invention, the method can further comprise analyzing the cell culture media for cytokine secretion, chemokine secretion, humoral factor secretion, microparticle secretion, growth factor secretion, shedding of a protein from the cellular surface, a metabolite of a compound, an immune cell, nitric oxide secretion, a vasodilator protein, a vasoconstrictive protein, miRNA, a secreted protein, or a secreted biological substance. The cell culture media can be analyzed for nitric oxide secretion by measuring nitrate or nitrite concentration.

When the cell culture media is analyzed for shedding of a protein from the cellular surface, the protein can comprise a vascular cell adhesion molecule (VCAM), E-selectin, or an intracellular adhesion molecule (ICAM).

In any of the methods of the invention, the method can further comprise the step of culturing the cell type or cell types.

In any of the methods of the invention wherein a drug or compound has been added to the culture media, the method can further comprise the step of comparing at least one of the cell types after applying the shear force for a period of time wherein the media includes the drug or the compound to the at least one of the cell types after applying the shear force for the period of time wherein the media does not include the drug or the compound, to determine the effect of the drug or compound on the at least one of the cell types.

In Vitro Liver Models

When a drug or a compound is tested for an effect on a healthy liver, the factors comprise insulin and glucose, hepatocytes are plated on the surface within the cell culture container, and the shear force is applied indirectly to the plated hepatocytes.

For example, the hepatocytes can be plated on a first surface of a porous membrane. The porous membrane is then suspended in the cell culture container such that the first surface is proximal and in spaced relation to a bottom surface of the cell culture container, thereby defining within the cell culture container a lower volume and an upper volume. The lower volume comprises the hepatocytes and the upper volume comprises a second surface of the porous membrane. The shear force is applied to the second surface of the porous membrane in the upper volume of the container.

In any of the methods of the invention, use of a porous membrane suspended in the cell culture container is preferred in plating the cells. When shear force is applied to plated cells or to the surface of the porous membrane (e.g., when the shear is applied on a surface of the membrane absent plated cells), the shear force can enable the cell culture media to perfuse from the upper volume to the lower volume. Such perfusion favorably impacts transport of factors from the upper volume to the lower volume, or vice versa.

The invention is also directed to a method of mimicking a pathological or physiologic condition of the liver in vitro. The method comprises adding a culture media to a cell culture container, adding at least one factor to the culture media, plating at least one hepatic cell type on at least one surface within the cell culture container, and applying a shear force upon the at least one plated hepatic cell type. The shear force results from flow of the culture media induced by a flow device. The flow mimics flow to which the at least one hepatic cell type is exposed in vivo in the pathological or physiologic condition.

In this method, the concentration of the factor in the culture media for mimicking the pathological condition can be within the in vivo concentration range of the factor observed in the pathological condition. Alternatively, in this method, the concentration of the factor in the culture media for mimicking the pathological condition can be within the concentration range of the factor that would result in vivo from administration of a drug or a compound. As a further alternative, in this method, the concentration of the factor in the culture media for mimicking the pathological condition can be capable of maintaining the mimicked pathological condition in vitro for a period of time under the shear force, the same concentration of factor being incapable of maintaining the mimicked pathological condition in vitro for the period of time in the absence of the shear force.

In this method, the concentration of the factor in the culture media for mimicking the physiologic condition can be within the in vivo concentration range of the factor observed in the physiologic condition. Alternatively, in this method, the concentration of the factor in the culture media for mimicking the physiologic condition can be within the concentration range of the factor that would result in vivo from administration of a drug or a compound. As a further alternative, in this method, the concentration of the factor in the culture media for mimicking the physiologic condition can be capable of maintaining the mimicked physiologic condition in vitro for a period of time under the shear force, the same concentration of factor being incapable of maintaining the mimicked physiologic condition in vitro for the period of time in the absence of the shear force.

In this method, a change in a level of a marker of the pathological or physiologic condition in the at least one plated hepatic cell type or in the culture media upon application of the shear force, as compared to the level of the marker in the at least one plated hepatic cell type or in the culture media in the absence of application of the shear force confirms mimicking of the pathological or physiologic condition.

The present invention is also directed to an in vitro method of testing a drug or a compound for an effect on a pathological or physiological condition. The method comprises mimicking the pathological or physiological condition, adding a drug or a compound to the culture media, and applying the shear force upon at least one plated hepatic cell type exposed to the drug or the compound. A change in the at least one plated hepatic cell type, in the presence of the drug or the compound, indicates that the drug or the compound has an effect on the pathological or physiological condition.

In this in vitro method of testing a drug or compound, the pathological condition can be mimicked by the in vitro method of mimicking a pathological or physiologic condition as described directly above.

The pathological or physiological condition of the in vitro method of testing a drug or compound can also be mimicked by plating primary cells or immortalized cells from a subject or subjects having the pathological condition, and culturing the cells in cell culture media.

The invention is also directed to a method of mimicking a pathological or physiologic condition of the liver in vitro. The method comprises adding a culture media to a cell culture container, depositing at least one extracellular matrix component on a surface within the cell culture container, plating hepatocytes on the at least one extracellular matrix component, and indirectly applying a shear force upon the at least one extracellular matrix component and the hepatocytes. The shear force results from flow of the culture media induced by a flow device. The flow mimics flow to which the hepatocytes are exposed in vivo in the pathological or physiologic condition.

In methods of the invention in which hepatic cells are plated on a porous membrane, at least one extracellular matrix component can be plated on a first surface of the porous membrane and the hepatic cells can subsequently be plated on the at least one extracellular matrix component. Optionally, nonparenchymal hepatic cells (e.g., sinusoidal endothelial cells) can be plated on the second surface of the porous membrane, and the shear stress applied to the nonparenchymal hepatic cells.

In the methods of the invention involving the deposition of an extracellular matrix component, for example, the at least one extracellular matrix component can be deposited on a first surface of a porous membrane. The hepatic cell type (e.g., hepatocytes) is subsequently plated on the at least one extracellular matrix component. The porous membrane is suspended in the cell culture container such that the first surface is proximal and in spaced relation to a bottom surface of the cell culture container, thereby defining within the cell culture container a lower volume and an upper volume. The lower volume comprises at least one extracellular matrix component and the hepatic cell type (e.g., hepatocytes), and the upper volume comprises a second surface of the porous membrane. The shear force is applied to the second surface of the porous membrane in the upper volume of the container. Optionally, nonparenchymal hepatic cells (e.g., sinusoidal endothelial cells) can be plated on the second surface of the porous membrane, and the shear stress applied to the nonparenchymal hepatic cells.

The invention also provides another method of mimicking a pathological or physiologic condition of the liver in vitro. The method comprises adding a culture media to a cell culture container, and plating hepatocytes on a first surface of a porous membrane. The porous membrane is suspended in the cell culture container such that the first surface is proximal and in spaced relation to a bottom surface of the container, thereby defining within the container a lower volume comprising the hepatocytes and an upper volume comprising a second surface of the porous membrane. A shear force is applied upon the second surface of the porous membrane in the upper volume of the container, the shear force resulting from flow of the culture media induced by a flow device. The flow mimics flow to which the hepatocytes are exposed in vivo in the pathological or physiologic condition. The flow device comprises a body adapted for being positioned in the culture media in the upper volume of the container and a motor adapted to rotate the body. Preferably, the body has a conical surface. It is also preferred that the flow device is adapted for positioning the conical surface of the body in the container and in contact with the cell culture media.

This method can further comprise plating nonparenchymal hepatic cells on the second surface of the porous membrane, wherein the shear stress is applied to the nonparenchymal hepatic cells. The nonparenchymal hepatic cells can comprise sinusoidal endothelial cells, hepatic stellate cells, Kupffer cells, or combinations thereof.

In the in vitro methods for mimicking a pathological or physiologic condition of the liver, a change in a level of a marker of the pathological or physiologic condition can be compared in the inventive method to the same method in the absence of application of the shear force. A change in the level of the marker in any of the hepatic cells or in the culture media upon application of the shear force as compared to the level of the marker in the hepatic cells or in the culture media in the absence of application of the shear force confirms mimicking of the pathological or physiologic condition. For example, a change in the level of the marker in the hepatocytes or nonparenchymal hepatic cells or in the culture media upon application of the shear force as compared to the level of the marker in the hepatocytes or nonparenchymal hepatic cells or in the culture media in the absence of application of the shear force confirms mimicking of the pathological or physiologic condition.

Pathological Conditions and Associated Factors

The pathological conditions include, but are not limited to, advanced inflammation, atherosclerosis, diabetic nephropathy, diabetic neuropathy, diabetic retinopathy, hypertension, hypertensive encephalopathy, hypertensive retinopathy, fatty liver disease, hypertension, heart failure, stroke, Marfan syndrome, carotid intima-medial thickening, atrial fibrillation, kidney disease, pulmonary fibrosis, chronic obstructive pulmonary disease, hyperlipidemia, hypercholesterolemia, diabetes, atherosclerotic plaque rupture, atherosclerotic plaque erosion, thoracic aortic aneurysm, cerebral aneurysm, abdominal aortic aneurysm, cerebral aneurysm, pulmonary artery disease, pulmonary hypertension, peripheral artery disease, deep vein thrombosis, vascular restenosis, vascular calcification, myocardial infarction, obesity, hypertriglyceridemia, hypoalphalipoproteinemia, fatty liver disease, hepatitis C, hepatitis B, liver fibrosis, bacterial infection, viral infection, cirrhosis, liver fibrosis, and alcohol-induced liver disease.

The pathological condition can comprise an anatomical condition, such as atrophy, calculi, choristoma, pathologic constriction, pathologic dilation, diverticulum, hypertrophy, polyps, prolapse, rupture, an arteriovenous fistula, or an appendage (e.g., left atrial appendage).

For a vascular pathological condition, endothelial cells, smooth muscle cells, or endocardial cells can be plated on the surface within the cell culture container, and the shear force applied upon the plated endothelial cells, smooth muscle cells, or endocardial cells.

For a vascular pathological condition, the factor can comprise oxidized low-density lipoprotein (oxLDL), tumor necrosis factor-α (TNFα), glucose, tissue growth factor-β (TGF-β), an elastin degradation product, elastase, vitamin D, an inorganic phosphate, leptin, adiponectin, apelin, aldosterone, angiotensin II, a triglyceride, high-density lipoprotein (HDL), oxidized high-density lipoprotein (oxHDL), a triglyceride-rich lipoprotein, low-density lipoprotein (LDL), insulin, a fatty acid, or a combination thereof.

The triglyceride-rich lipoprotein can comprise very low-density lipoprotein (vLDL), a vLDL remnant, a chylomicron, or a chylomicron remnant.

For a vascular pathological condition where a porous membrane is used, endocardial cells can be plated on a first surface of a porous membrane. The porous membrane is suspended in the cell culture container such that the first surface is proximal and in spaced relation to a bottom surface of the cell culture container, thereby defining within the cell culture container a lower volume comprising the endocardial cells and an upper volume comprising a second surface of the porous membrane. The shear force is applied to the second surface of the porous membrane in the upper volume. Optionally, endothelial cells can be plated on the second surface of the porous membrane, and the shear force applied upon the plated endothelial cells.

The endocardial cells can comprise smooth muscle cells.

When the vascular pathological condition is atrial fibrillation, or atrial fibrillation and associated hypertension, the cell types can comprise endothelial cells, smooth muscle cells, endocardial cells, or a combination thereof. Preferably, the cell types are endothelial; smooth muscle; endothelial and smooth muscle; endocardial; or endocardial and endothelial.

For a vascular pathological condition such as atrial fibrillation, or atrial fibrillation and associated hypertension, the plated cell types can be from a normal subject, a subject having diabetes, a hypertensive subject, an aged subject, or an animal genetically modified to model diabetes, hypertension, or aging.

When the vascular pathological condition is atrial fibrillation, or atrial fibrillation and associated hypertension, the flow or hemodynamic pattern can be derived from a cardiac sinus or from an atrial fibrillation rhythm.

When the vascular pathological condition is atrial fibrillation, or atrial fibrillation and associated hypertension, the factor can comprise oxLDL, TNFα, aldosterone, angiotensin II, or a combination thereof. For example, the factor(s) can comprise oxLDL; TNFα; oxLDL and TNFα; aldosterone; angiotensin II; aldosterone and angiotensin II; oxLDL, TNFα, and angiotensin II; oxLDL, TNFα, and aldosterone; or oxLDL, TNFα, aldosterone, and angiotensin II.

For a vascular pathological condition where a porous membrane is used, smooth muscle cells can be plated on a first surface of the porous membrane. The porous membrane is suspended in the cell culture container such that the first surface is proximal and in spaced relation to a bottom surface of the cell culture container, thereby defining within the cell culture container a lower volume comprising the smooth muscle cells and an upper volume comprising a second surface of the porous membrane. The shear force is applied to the second surface of the porous membrane in the upper volume. Optionally, endothelial cells can be plated on the second surface of the porous membrane.

For a vascular pathological condition where a porous membrane is used, endothelial cells can be plated on a second surface of a porous membrane. The porous membrane is suspended in the cell culture container such that a first surface of the porous membrane is proximal and in spaced relation to a bottom surface of the cell culture container, thereby defining within the cell culture container a lower volume comprising the first surface of the porous membrane and an upper volume comprising the endothelial cells. The shear force is applied to the endothelial cells in the upper volume. Optionally, smooth muscle cells can be plated on the first surface of the porous membrane.

When the vascular pathological condition is an advanced inflammation, such as atherosclerosis, the cell types can comprise endothelial cells, smooth muscle cells, or a combination thereof. Preferably, the cell types are endothelial; smooth muscle; or endothelial and smooth muscle.

When the vascular pathological condition is an advanced inflammation, such as atherosclerosis, the plated cell types can be from a normal subject, a subject having diabetes, a hypertensive subject, or an animal genetically modified to model diabetes or hypertension.

When the vascular pathological condition is advanced inflammation, such as atherosclerosis, the flow or hemodynamic pattern can be atheroprone, atheroprotective (i.e., also described herein as "healthy state"), derived from a femoral artery, or derived from an arteriole.

When the vascular pathological condition is advanced inflammation such as atherosclerosis, the factor can comprise LDL, oxLDL, TNFα, HDL, a triglyceride-rich lipoprotein, or a combination thereof. For example, the factor(s) can comprise LDL; LDL and oxLDL; oxLDL; HDL; HDL and oxLDL; TNFα; TNFα and oxLDL; TNFα, oxLDL, and HDL; or TNFα, oxLDL, and a triglyceride-rich lipoprotein.

When the vascular pathological condition is an advanced inflammation, such as hypertriglyceridemia, the cell types can comprise endothelial cells, smooth muscle cells, or a combination thereof. Preferably, the cell types are endothelial; smooth muscle; or endothelial and smooth muscle.

When the vascular pathological condition is an advanced inflammation, such as hypertriglyceridemia, the plated cell types can be from a normal subject, a subject having diabetes, a hypertensive subject, or an animal genetically modified to model diabetes or hypertension.

When the vascular pathological condition is advanced inflammation, such as hypertriglyceridemia, the flow or hemodynamic pattern can be atheroprone, atheroprotective, derived from a femoral artery, or derived from an arteriole.

When the vascular pathological condition is advanced inflammation such as hypertriglyceridemia, the factor can comprise a triglyceride-rich lipoprotein.

When the vascular pathological condition is abdominal aortic aneurysm, the cell types can comprise endothelial cells, smooth muscle cells, or a combination thereof. Preferably, the cell types are endothelial; smooth muscle; or endothelial and smooth muscle.

When the vascular pathological condition is abdominal aortic aneurysm, the plated cell types can be from a normal subject, a subject having diabetes, a hypertensive subject, a smoker, a subject having abdominal aortic aneurysm, or an animal genetically modified to model diabetes or hypertension or modified to model abdominal aortic aneurysm.

When the vascular pathological condition is abdominal aortic aneurysm, the flow or hemodynamic pattern can be derived from an abdominal artery or derived from an intra-abdominal aortic aneurysm rhythm.

When the vascular pathological condition is abdominal aortic aneurysm, the factor can comprise oxLDL, TNFα, glucose, an elastin degradation product, elastase, angiotensin II, aldosterone, insulin, TGF-β, or a combination thereof. For example, the factor(s) can be oxLDL; TNFα; glucose; an elastin degradation product; elastase; angiotensin II; aldosterone; insulin; TGF-β; oxLDL and TNFα; oxLDL and glucose; oxLDL and an elastin degradation product; oxLDL and elastase; oxLDL and angiotensin II; oxLDL and aldosterone; oxLDL and insulin; oxLDL and TGF-β; TNFα and glucose; TNFα and an elastin degradation product; TNFα and elastase; TNFα and angiotensin II; TNFα and aldosterone; TNFα and insulin; TNFα and TGF-β; glucose and an elastin degradation product; glucose and elastase; glucose and angiotensin II; glucose and aldosterone; glucose and insulin; glucose and TGF-β; an elastin degradation product and elastase; an elastin degradation product and angiotensin II; an elastin degradation product and aldosterone; an elastin degradation product and insulin; an elastin degradation product and TGF-β; elastase and angiotensin H; elastase and aldosterone; elastase and insulin; elastase and TGF-β; angiotensin II and aldosterone; angiotensin II and insulin; angiotensin II and TGF-3; aldosterone and insulin; aldosterone and TGF-β; insulin and TGF-β; oxLDL, TNFα, and glucose; oxLDL, TNFα, and an elastin degradation product; oxLDL, TNFα, and elastase; oxLDL, TNFα, and angiotensin II; oxLDL, TNFα, and aldosterone; oxLDL, TNFα, and insulin; oxLDL, TNFα, and TGF-β; TNFα, glucose, and an elastin degradation product; TNFα, glucose, and elastase; TNFα, glucose, and angiotensin II; TNFα, glucose, and aldosterone; TNFα, glucose, and insulin; TNFα, glucose, and TGF-β; and the like.

When the vascular pathological condition is abdominal aortic aneurysm, smoke extract can be added to the culture media.

When the vascular pathological condition is a diabetic vascular condition, such as diabetic nephropathy, diabetic neuropathy, or diabetic retinopathy, the cell types can comprise endothelial cells, smooth muscle cells, or a combination thereof. Preferably, the cell types are endothelial; smooth muscle; or endothelial and smooth muscle.

When the vascular pathological condition is a diabetic vascular condition, such as diabetic nephropathy, diabetic neuropathy, or diabetic retinopathy, the plated cell types can be from a normal subject, a subject having diabetes, or an animal genetically modified to model diabetes.

When the vascular pathological condition is a diabetic vascular condition, such as diabetic nephropathy, diabetic neuropathy, or diabetic retinopathy, the flow or hemodynamic pattern can be atheroprone, atheroprotective, derived from a femoral artery, or derived from an arteriole.

When the vascular pathological condition is a diabetic vascular condition, such as diabetic nephropathy, diabetic neuropathy, or diabetic retinopathy, the factor can comprise oxLDL, TNFα, glucose, HDL, oxHDL, a triglyceride-rich lipoprotein, insulin, or a combination thereof. For example, the factor(s) can comprise glucose; glucose and insulin; glucose, oxLDL, and TNFα; glucose, insulin, oxLDL, and TNFα; glucose, oxLDL, TNFα, and HDL; glucose, oxLDL, TNFα, and oxHDL; glucose, oxLDL, TNFα, HDL, and oxHDL; glucose, insulin, oxLDL, TNFα, and HDL; glucose, insulin, oxLDL, TNFα, and oxHDL; glucose, insulin, oxLDL, TNFα HDL, and oxHDL; glucose, oxLDL, TNFα, and a triglyceride-rich lipoprotein; or glucose, insulin, oxLDL, TNFα, and a triglyceride-rich lipoprotein.

When the vascular pathological condition is hypertension, the cell types can comprise endothelial cells, smooth muscle cells, or a combination thereof. Preferably, the cell types are endothelial; smooth muscle; or endothelial and smooth muscle.

When the vascular pathological condition is hypertension, the plated cell types can be from a normal subject, a subject having diabetes, a hypertensive subject, or an animal genetically modified to model diabetes or hypertension.

When the vascular pathological condition is hypertension, the flow or hemodynamic pattern can be atheroprone, atheroprotective, or derived from a femoral artery, a pulmonary artery, or an arteriole.

When the vascular pathological condition is hypertension, the factor can comprise oxLDL, TNFα, angiotensin II, aldosterone, or a combination thereof. For example, the factor(s) can comprise angiotensin II; aldosterone; angiotensin II and aldosterone; or angiotensin II, aldosterone, oxLDL and TNFα.

When the vascular pathological condition is artery calcification, the cell types can comprise endothelial cells, smooth muscle cells, or a combination thereof. Preferably, the cell types are endothelial; smooth muscle; or endothelial and smooth muscle.

When the vascular pathological condition is artery calcification, the plated cell types can be from a normal subject, a subject having diabetes, a hypertensive subject, or an animal genetically modified to model diabetes or hypertension.

When the vascular pathological condition is artery calcification, the flow or hemodynamic pattern can be atheroprone, atheroprotective, or derived from a femoral artery, a pulmonary artery, or an arteriole.

When the vascular pathological condition is artery calcification, the factor can comprise oxLDL, TNFα, vitamin D, an inorganic phosphate, leptin, adiponectin, or a combination thereof. For example, the factor(s) can comprise oxLDL; TNFα; vitamin D; an inorganic phosphate; leptin; adiponectin; oxLDL and TNFα; oxLDL and vitamin D; oxLDL and an inorganic phosphate; oxLDL and leptin; oxLDL and adiponectin; TNFα and vitamin D; TNFα and an inorganic phosphate; TNFα and leptin; TNFα and adiponectin; vitamin D and an inorganic phosphate; vitamin D and leptin; vitamin D and adiponectin; an inorganic phosphate and leptin; an inorganic phosphate and adiponectin; leptin and adiponectin; oxLDL, TNFα, and vitamin D; oxLDL, TNFα, and an inorganic phosphate; oxLDL, TNFα, and leptin; oxLDL, TNFα, and adiponectin; TNFα, vitamin D, and an inorganic phosphate; TNFα, vitamin D, and leptin; TNFα, vitamin D, and adiponectin; and the like.

When the vascular pathological condition is thrombosis, the cell types can comprise endothelial cells, smooth muscle cells, or a combination thereof. Preferably, the cell types are endothelial; smooth muscle; or endothelial and smooth muscle.

When the vascular pathological condition is thrombosis, the plated cell types can be from a normal subject, a subject having diabetes, a hypertensive subject, or an animal genetically modified to model diabetes or hypertension.

When the vascular pathological condition is thrombosis, the flow or hemodynamic pattern can be atheroprone, atheroprotective, or derived from a femoral artery, a pulmonary artery, or an arteriole.

When the vascular pathological condition is thrombosis, the factor can comprise TNFα, oxLDL, glucose, or a combination thereof. For example, the factor(s) can comprise TNFα; oxLDL; glucose; or oxLDL and glucose.

When the pathological condition is fatty liver disease, the cell types can comprise hepatocytes, nonparenchymal hepatic cells, or combinations thereof. The nonparenchymal hepatic cells can include sinusoidal endothelial cells, hepatic stellate cells, Kupffer cells, or combinations thereof.

When the vascular pathological condition is fatty liver disease, the flow or hemodynamic pattern can be from a normal subject, a subject having fatty liver disease, or an animal genetically modified to model fatty liver disease.

Where the pathological condition is fatty liver disease and a porous membrane is used, hepatocytes can be plated on a first surface of the porous membrane. The porous membrane is suspended in the cell culture container such that the first surface is proximal and in spaced relation to a bottom surface of the cell culture container, thereby defining within the cell culture container a lower volume comprising the hepatocytes and an upper volume comprising a second surface of the porous membrane. The shear force is applied to the second surface of the porous membrane in the upper volume. Optionally, nonparenchymal hepatic cells can be plated on the second surface of the porous membrane, and the shear force is applied to the nonparenchymal hepatic cells in the upper volume. Optionally, an extracellular matrix component can be deposited on the first surface of the porous membrane, and subsequently hepatoctyes can be plated on the extracellular matrix component.

Where the pathological condition is fatty liver disease and a porous membrane is used, nonparenchymal hepatic cells can be plated on a second surface of a porous membrane. The porous membrane is suspended in the cell culture container such that a first surface of the porous membrane is proximal and in spaced relation to a bottom surface of the cell culture container, thereby defining within the cell culture container a lower volume comprising the first surface of the porous membrane and an upper volume comprising the nonparenchymal hepatic cells. The shear force is applied to the nonparenchymal hepatic cells in the upper volume. Optionally, an extracellular matrix component can be deposited on the first surface of the porous membrane, and subsequently hepatoctyes can be plated on the extracellular matrix component.

When the vascular pathological condition is fatty liver disease, the factor can comprise insulin, glucose, or a combination thereof. For example, the factor(s) can comprise insulin; glucose; or insulin and glucose.

When the pathological condition is diabetes, the cell type can comprise β-cells and the factor can comprise insulin, glucose, or insulin and glucose.

Physiologic Conditions

The physiologic conditions that can be mimicked in the methods of the invention include the physiologic conditions corresponding to any pathological condition of interest, such pathological conditions being described herein. For example, a physiologic condition corresponding to fatty liver disease can be a healthy liver state, and a physiologic condition corresponding to atherosclerosis can be an atheroprotective state.

Flow Devices

The shear force can be applied using any suitable flow device which is capable of inducing flow of the culture media, wherein the flow mimics flow to which the cell type or cell types being cultured are exposed in vivo in the pathological or physiological condition. For example, the flow device can be a cone-and-plate device or a parallel plate flow device.

The flow device can be a cone-and-plate device substantially as described in U.S. Pat. No. 7,811,782 and in Hastings, et al., *Atherosclerosis prone hemodynamics differentially regulates endothelial and smooth muscle cell phenotypes and promotes pro-inflammatory priming*, AMERICAN J. PHYSIOLOGY & CELL PHYSIOLOGY 293:1824-33 (2007), the contents of each of which are hereby incorporated by reference. An example of such a device is depicted in FIG. 15B. The device 200 comprises an electronic controller for receiving a set of electronic instructions, a motor 220 operated by the electronic controller, and a shear force applicator operatively connected to the motor for being driven by the motor. The shear force applicator can comprise a cone 230 which is attached to the motor, and the cone can be directly driven by the motor. The motor causes the cone to rotate in either direction (clockwise or counterclockwise).

The cone-and-plate device accommodates a cell culture container, for example a Petri dish (e.g., a 75-mm diameter Petri dish). The cone is adapted to fit inside the cell culture container. Thus, for example, in a device adapted for use with 75-mm diameter Petri dishes, the cone has a diameter of about 71.4 mm. The cone generally has a shallow cone angle. For example, the angle between the surface of the cone and the surface within the Petri dish is approximately 1°.

When the cone of the device is submerged in culture media in the Petri dish and rotated by the motor, the cone exerts a rotational force upon the culture media, and this in turn applies shear force to cells plated within the cell culture container or to a surface of a porous membrane suspended in the cell culture container.

The cone-and-plate device can also include a base for securely holding the cell culture container. The device can also include clips that mount on the Petri dish and secure inflow and outflow tubing which is used to perfuse the upper and lower volumes, as described further below.

The flow can be derived from a previously measured hemodynamic pattern, and can be modeled into a set of electronic instructions. The shear force is based on the set of electronic instructions. The flow device comprises an electronic controller for receiving the set of electronic instructions. The motor is operated by the electronic controller. A shear force applicator operatively connected to the motor is driven by the motor. Preferably, the shear force applicator comprises a cone attached to the motor.

The flow device is used in conjunction with a cell culture container. The cell culture container can include inlets and outlets for the flow of cell culture media, factors, drugs, compounds and other components into and out of the cell culture container.

Figure 23:
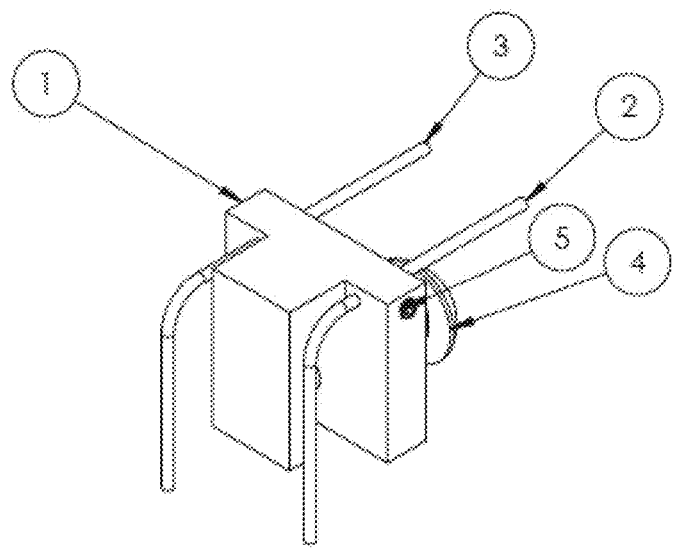
FIG. 23 is a perspective of the clip that mounts on the cell culture dish and secures inflow and outflow tubing to perfuse the upper and lower volumes.

The inlets and outlets for the flow device can be secured to the cell culture container by a clip. FIG. 23 depicts such a clip. Each clip is made up of three parts: the main body 1 and two pieces of thin metal tubing 2 and 3 as shown in FIG. 23. The clip can be secured to the side of a cell culture dish from the outside by a screw 4. For example, two clips can be attached and tightened to the side of the dish from the outside by a screw 4, as shown in FIGS. 24A and B). The main body 1 is made of treated stainless steel metal and angles around the edge of the dish for attachment and access purposes. Two pieces of thin metal tubing (2 and 3) per clip are bent to provide access to the dish for supplying and drawing off media efficiently, without obstructing the cone rotation. A set screw 5 on either side of the main body 1 secures the metal tubing 2, 3 to the main body and holds the metal tubing in place such that it extends to the correct depth within the culture media. Flexible tubing then slides over the metal tubing, which is used to draw media (e.g., from the source bottle to the dish via mechanical peristaltic pump in the device of the examples).

Figure 24:
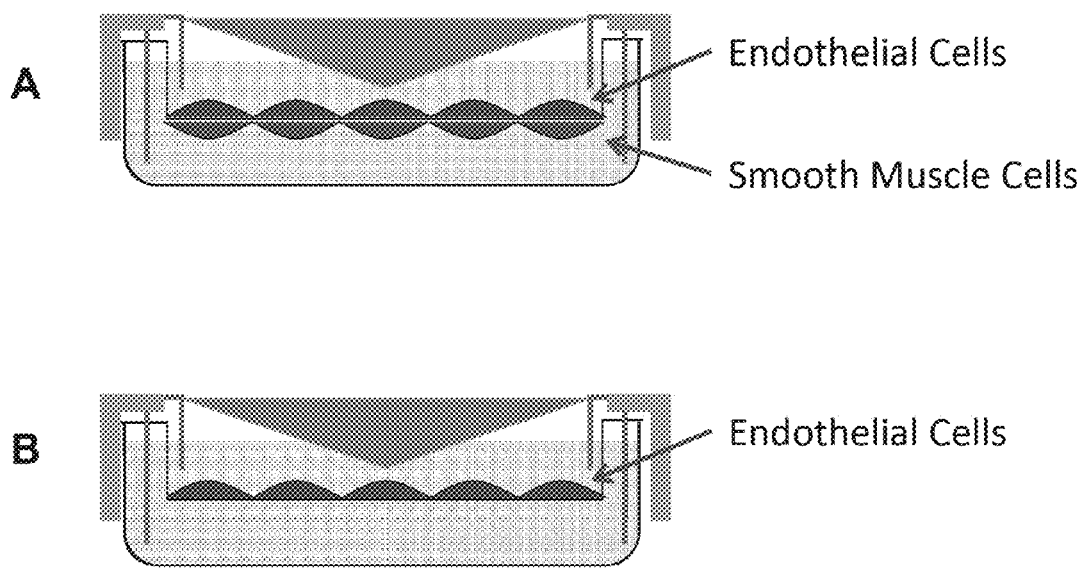
FIG. 24 shows exemplary plating configurations of endothelial cells and smooth muscle cells within the cell culture container.

FIGS. 24A and 24B show the clips positioned in a cell culture container. In the configurations shown in FIG. 24, a porous membrane suspended is suspended in the cell culture container, with endothelial cells only (FIG. 24B) or endothelial cells and smooth muscle cells (FIG. 24A) plated on surfaces of the porous membrane.

Hemodynamic Patterns

The hemodynamic pattern can be derived from a subject or subjects having the pathological condition or a disease-promoting condition. The disease-promoting condition can comprise atrophy, calculi, choristoma, pathologic constriction, pathologic dilation, diverticulum, hypertrophy, polyps, prolapse, rupture, an arteriovenous fistula, or an appendage (e.g., a left atrial appendage).

The hemodynamic pattern can be derived from at least a portion of an artery, an arteriole, a vein, a venule, or an organ.

When a hemodynamic pattern is derived from at least a portion of an artery or an arteriole, the artery or arteriole can comprise a carotid artery, thoracic artery, abdominal artery, pulmonary artery, femoral artery, renal efferent artery, renal afferent artery, coronary artery, brachial artery, internal mammary artery, cerebral artery, aorta, pre-capillary arteriole, hepatic artery, anterior cerebral artery, middle cerebral artery, posterior cerebral artery, basilar artery, external carotid artery, internal carotid artery, vertebral artery, subclavian artery, aortic arch, axillary artery, internal thoracic artery, branchial artery, deep branchial artery, radial recurrent artery, superior epigastric artery, descending aorta, inferior epigastric artery, interosseous artery, radial artery, ulnar artery, palmar carpal arch, dorsal carpal arch, superficial or deep palmar arch, digital artery, descending branch of the femoral circumflex artery, descending genicular artery, superior genicular artery, inferior genicular artery, anterior tibial artery, posterior tibial artery, peroneal artery, deep plantar arch, arcuate artery, common carotid artery, intercostal arteries, left or right gastric artery, celiac trunk, splenic artery, common hepatic artery, superior mesenteric artery, renal artery, inferior mesenteric artery, testicularis artery, common iliac artery, internal iliac artery, external iliac artery, femoral circumflex artery, perforating branch, deep femoral artery, popliteal artery, dorsal metatarsal artery, or dorsal digital artery.

When a hemodynamic pattern is derived from at least a portion of an vein or venule, the vein or venule can comprise a post-capillary venule, saphenous vein, hepatic portal vein, superior vena cava, inferior vena cava, coronary vein, Thesbian vein, superficial vein, perforator vein, systemic vein, pulmonary vein, jugular vein, sigmoid sinus, external jugular vein, internal jugular vein, inferior thyroid vein, subclavian vein, internal thoracic vein, axillary vein, cephalic vein, branchial vein, intercostal vein, basilic vein, median cubital vein, thoracoepigastric vein, ulnar vein, median antebranchial vein, inferior epigastric vein, deep palmar arch, superficial palmar arch, palmar digital vein, cardiac vein, inferior vena cava, hepatic vein, renal vein, abdominal vena cava, testicularis vein, common iliac vein, perforating branch, external iliac vein, internal iliac vein, external pudendal vein, deep femoral vein, great saphenous vein, femoral vein, accessory saphenous vein, superior genicular vein, popliteal vein, inferior genicular vein, great saphenous vein, small saphenous vein, anterior or posterior tibial vein, deep plantar vein, dorsal venous arch, or dorsal digital vein.

When a hemodynamic pattern is derived from at least a portion of an organ, the organ can comprise a liver, a kidney, a lung, a brain, a pancreas, a spleen, a large intestine, a small intestine, a heart, a skeletal muscle, an eye, a tongue, a reproductive organ, or an umbilical cord.

The hemodynamic pattern can be derived from analysis of ultrasound data.

The hemodynamic pattern can be derived from analysis of magnetic resonance imaging (MRI) data.

The flow or the hemodynamic pattern can be time-variant.

The flow or the hemodynamic pattern can be derived from a chamber of the heart, a left atrial appendage during sinus rhythm, an atrial fibrillation, or a ventricular fibrillation.

When the flow or the hemodynamic pattern is derived from a chamber of the heart, the chamber of the heart can comprise a left atrium, a right atrium, a left ventricle or a right ventricle.

The flow or the hemodynamic pattern can result from a physical change resulting from a pathological condition.

The flow or hemodynamic pattern can be derived from a subject wherein blood flow or a hemodynamic pattern has been altered as a direct or indirect effect of administration of a drug to a subject as compared to the flow or the hemodynamic pattern for the subject absent administration of the drug.

The flow or the hemodynamic pattern can be derived from an animal, such as a genetically modified animal or a human. Preferably, the pattern is derived from a human.

Cell Types

Cell types for use in methods of the invention include primary cells and immortalized cells. The primary cells or immortalized cells can comprise cells isolated from at least one subject having the pathological or physiologic condition, cells isolated from at least one subject having a risk factor for the pathological condition, cells isolated from at least one subject with a single nucleotide polymorphism linked to a pathological condition, cells isolated from at least one subject with an identified genotype linked to drug toxicity, or cells isolated from at least one subject with a single nucleotide polymorphism linked to drug toxicity.

The primary cells or the immortalized cells used in in vitro methods of the invention involving a physiologic condition comprise cells isolated from at least one subject having the physiologic condition, cells isolated from at least one subject having a risk factor for a pathological condition, cells isolated from at least one subject with a single nucleotide polymorphism linked to a pathological condition, cells isolated from at least one subject with an identified genotype linked to drug toxicity, or cells isolated from at least one subject with a single nucleotide polymorphism linked to drug toxicity.

The primary cells or immortalized cells used in in vitro methods of the invention involving a pathological condition can comprise cells isolated from at least one subject having the pathological condition, cells isolated from at least one subject having a risk factor for the pathological condition, cells isolated from at least one subject with a single nucleotide polymorphism linked to the pathological condition, cells isolated from at least one subject with an identified genotype linked to drug toxicity, or cells isolated from at least one subject with a single nucleotide polymorphism linked to drug toxicity.

The primary cells or immortalized cells used in in vitro methods of the invention involving a pathological condition can comprise cells isolated from at least one subject not having the pathological condition, cells isolated from at least one subject not having a risk factor for the pathological condition, cells isolated from at least one subject without a single nucleotide polymorphism linked to the pathological condition, cells isolated from at least one subject without an identified genotype linked to drug toxicity, or cells isolated from at least one subject without a single nucleotide polymorphism linked to drug toxicity.

The primary cells or immortalized cells used in in vitro methods of the invention involving a pathological condition can comprise cells isolated from at least one subject having a different pathological condition, cells isolated from at least one subject having a risk factor for a different pathological condition, or cells isolated from at least one subject with a single nucleotide polymorphism linked to a different pathological condition.

When the cells are isolated from at least one subject having a risk factor for the pathological condition, the risk factor can include, but is not limited to, smoking, age, gender, race, epigenetic imprinting, an identified genotype linked to the pathological condition, an identified single nucleotide polymorphism linked to the pathological condition, diabetes, hypertension, atherosclerosis, atherosclerotic plaque rupture, atherosclerotic plaque erosion, thoracic aortic aneurysm, cerebral aneurysm, abdominal aortic aneurysm, cerebral aneurysm, heart failure, stroke, Marfan syndrome, carotid intima-medial thickening, atrial fibrillation, kidney disease, pulmonary fibrosis, chronic obstructive pulmonary disease, pulmonary artery disease, pulmonary hypertension, hyperlipidemia, familial hypercholesterolemia, peripheral artery disease, deep vein thrombosis, vascular restenosis, vascular calcification, myocardial infarction, obesity, hypertriglyceridemia, hypoalphalipoproteinemia, fatty liver disease, hepatitis C, hepatitis B, liver fibrosis, bacterial infection, viral infection, cirrhosis, liver fibrosis, or alcohol-induced liver disease.

The primary cells can include a cell lineage derived from stem cells (e.g., adult stem cells, embryonic stem cells, inducible pluripotent stem cells, or bone marrow-derived stem cells) or stem-like cells. The cell lineage derived from stem cells or stem-like cells can comprise endothelial cells, smooth muscle cells, cardiac myocytes, hepatocytes, neuronal cells, or endocrine cells.

Cell types for use in methods of the invention include renal cells, cells of the airways, blood-brain barrier cells, vascular cells, hepatic cells, pancreatic cells, cardiac cells, muscle cells, spleen cells, gastrointestinal tract cells, skin cells, liver cells, immune cells, or hematopoietic cells.

Specific cell types for use in the methods include astrocytes, endothelial cells, glomerular fenestrated endothelial cells, renal epithelial podocytes, alpha cells, β-cells, delta cells, pancreatic polypeptide (PP) cells, epsilon cells, glial cells, hepatocytes, neurons, nonparenchymal hepatic cells, podocytes, smooth muscle cells, mesangial cells, pericytes, cardiac muscle cells, skeletal muscle cells, leukocytes, monocytes, myocytes, macrophages, neutrophils, dendritic cells, T-cells, B-cells, endothelial progenitor cells, stem cells, circulating stem cells, and circulating hematopoietic cells. The nonparenchymal hepatic cells include hepatic stellate cells, sinusoidal endothelial cells, and Kupffer cells. Preferably, the specific cell types can include endothelial cells, smooth muscle cells, hepatocytes, sinusoidal endothelial cells, or a combination thereof.

The cell types for use in the methods of the invention can be animal cell types, such as cells from a genetically modified animal. The animal cell types are preferably human cell types. The human cell types can be selected on the basis of age, gender, race, epigenetics, disease, nationality, the presence or absence of one or more single nucleotide polymorphisms, a risk factor as described herein, or some other characteristic that is relevant to the pathological or physiologic condition.

The shear force applied in the methods of the invention can be applied indirectly to the at least one plated cell type.

The shear force applied in the methods of the invention can be applied directly to the at least one plated cell type.

The cell types, additional components such as extracellular matrix component, and the porous membrane are within the culture media (i.e., covered with culture media) in the methods of the invention.

The methods of the invention can further comprise analyzing at least one of the cell types for toxicity, inflammation, permeability, compatibility, cellular adhesion, cellular remodeling, cellular migration, or phenotypic modulation resulting from the drug or the compound.

Cell Culture Media

Standard cell culture media can be used in the methods of the invention.

Factors Added to Cell Culture Media

The factors that can be added to the cell culture media are described throughout the specification in conjunction with an associated pathological or physiologic condition.

In Vivo Factor Concentrations

The physiologic in vivo concentrations of the factors are well known in the art, as are the methods of determining these in vivo concentrations. For example, the respective in vivo concentrations of HDL in a healthy human and in a human having atherosclerosis are greater than 30 mg/dl to 200 mg/dl, and less than 30 mg/dl, as determined from whole blood. Methods for determining in vivo concentrations of factors are available in the *United States Pharmacopeia* and in other literature.

A reported in vivo concentration range for a factor can vary depending upon the method used for determining the range, the source from which the factor is obtained (e.g., whole blood or serum), the medical condition of the patient (i.e., whether the patient has a pathological condition or physiologic condition), and time of day relative to normal sleep and eating schedule. However, it would be known to one of ordinary skill in the art that a concentration outside an in vivo physiological concentration range reported in the literature would be an in vivo pathological concentration using the method reported for determining the concentration. Likewise, a concentration below the lower endpoint or above the upper endpoint of an in vivo pathological concentration range reported in the literature would be an in vivo physiologic concentration using the method reported for determining the concentration; whether the in vivo physiologic concentration is below the lower endpoint or above the upper endpoint will depend upon the factor. For example, the in vivo physiologic concentration of the factor HDL would be above the upper endpoint of the range, but the in vivo physiologic concentration of the factor oxLDL would be below the lower endpoint of the range, as would be recognized by one of ordinary skill in the art.

Other Components

Extracellular Matrix Components

Extracellular matrix components for use in the methods of the invention can comprise heparan sulfate, chondroitin sulfate, keratan sulfate, hyaluronic acid, a collagen, an elastin, a fibronectin, a laminin, a vitronectin, or combinations thereof. Collagen is a preferred extracellular matrix component, and is preferably the type of collagen that is present in the in vivo environment of the cell type or cell type(s) that are plated for a particular pathological or physiologic condition.

The extracellular matrix component can be secreted by fibroblasts, chondrocytes, or osteoblasts plated on the surface within the cell culture container.

The extracellular matrix component is especially suitable for use in the methods of the invention involving the liver.

Drug or Compound

The drug or compound can be an anti-inflammatory agent, an anti-neoplastic agent, an anti-diabetic agent, a protein kinase inhibitor, an anti-thrombotic agent, a thrombolytic agent, an anti-platelet agent, an anti-coagulant, a calcium channel blocker, a chelating agent, a rho kinase inhibitor, an anti-hyperlipidemic agent, an agent that raises HDL, an anti-restenosis agent, an antibiotic, an immunosuppressant, an anti-hypertensive agent, a diuretic, an anorectic, an appetite suppressant, an anti-depressant, an anti-psychotic, a contraceptive, a calcimimetic, a biologic medical product, or a combination thereof.

When the drug is an anti-inflammatory agent, the anti-inflammatory agent can comprise a steroid (e.g., prednisone, hydrocortisone, prednisolone, betamethasone, or dexamethasone), a non-steroidal anti-inflammatory drug (NSAID) (e.g., a salicylate, ibuprofen, acetaminophen, naproxen, or ketoprofen), a selective cyclooxygenase inhibitor (e.g., celecoxib or rofecoxib), a non-selective cyclooxygenase inhibitor, an immune selective anti-inflammatory agent (e.g., phenylalanine-glutamine-glycine tripeptide), or a combination thereof.

When the drug comprises an anti-neoplastic agent, the anti-neoplastic agent can comprise an alkylating agent (e.g., cisplatin, carboplatin, oxaliplatin, mechlorethamine, cyclophosphamide, chlorambucide, or ifosfamide), an anti-metabolite (e.g., azathioprine or mercaptopurine), a plant alkaloid (e.g., a taxane such as paclitaxel or docetaxel, a vinca alkaloid such as vincristine, vinblastine, or vindesine, or a podophyllotoxin such as etoposide or teniposide), a topoisomerase inhibitor (e.g., irinotecan, topotecan, or amsacrine), a cytotoxic antibiotic (e.g., actinomycin, bleomycin, plicamysin, mitomycin, doxorubicin, daunorubicin, valrubicin, idarubicin, or epirubicin), or a combination thereof.

When the drug is an anti-diabetic agent, the anti-diabetic agent can comprise a biguanide (e.g., metformin), a thiazolidinedione (e.g., rosiglitazone, troglitazone, or pioglitazone), a sulfonylurea (e.g., tolbutamine, acetohexamide, tolazamide, chlorpropamide, glipazide, glyburide, glimepiride, gliclazide, glycopyraniide, or gliquidone), an incretin mimetic (e.g., exenatide, liraglutide, or taspoglutide), a dipeptidyl peptidase IV inhibitor (e.g., vildagliptin, sitagliptin, saxaglitpin, linagliptin, alogliptin, or septagliptin), a sodium-glucose co-transporter 2 inhibitor (e.g., dapagliflozin, canagliflozin, empagliflozin, ipragliflozin, remogliflozin, or sergliflozin), or a glucokinase activator (e.g., piragliatin).

When the drug comprises a protein kinase inhibitor, the protein kinase inhibitor can comprise a serine/threonine-specific kinase inhibitor, a tyrosine-specific kinase inhibitor (e.g., imatinib, bevacizumab, cetuximab, axitinib, lapatinib, ruxolitinib, or sorafenib), an epidermal growth factor (EGF) receptor inhibitor, a fibroblast growth factor (FGF) receptor inhibitor, a platelet-derived growth factor (PDGF) receptor inhibitor, or a vascular endothelial growth factor (VEGF) receptor inhibitor.

When the drug comprises the anti-thrombotic agent, the anti-thrombotic agent can comprise dipyridamole, urokinase, r-urokinase, r-prourokinase, reteplase, alteplase, streptokinase, rt-PA, TNK-rt-PA, monteplase, staphylokinase, pamiteplase, unfractionated heparin, or APSAC.

When the drug comprises the thrombolytic agent, the thrombolytic agent can comprise a streptokinase, a urokinase, or a tissue plasminogen activator.

When the drug comprises the anti-platelet agent, the anti-platelet agent can comprise a glycoprotein IIb/IIIa inhibitor, a thromboxane inhibitor, an adenosine diphosphate receptor inhibitor, a prostaglandin analogue, or a phosphodiesterase inhibitor. For example, the anti-platelet agent can comprise clopidogrel, abciximab, tirofiban, orbofiban, xemilofiban, sibrafiban, roxifiban, or ticlopinin.

When the drug comprises the anti-coagulant, the anti-coagulant can comprise a vitamin K antagonist (e.g., warfarin), a factor Xa inhibitor (e.g., apixaban, betrixaban, edoxaban, otamixaban, rivaroxaban, fondaparinux, or idraparinux), or a direct thrombin inhibitor (e.g., hirudin, bivalirudin, lepirudin, desirudin, dabigatran, ximelagatran, melagatran, or argatroban).

When the drug comprises the calcium channel blocker, the calcium channel blocker can comprise verapamil, diltiazem, amlodipine, aranidipine, azelnidipine, barnidipine, benidipine, cilnidipine, clevidipine, isradipine, efonidipine, felodipine, lacidipine, lercanidipine, manidipine, nicardipine, nifedipine, nilvadipine, nimodipine, nisoldipine, nitrendipine, or pranidipine.

When the drug comprises the chelating agent, the chelating agent can comprise penicillamine, triethylene tetramine dihydrochloride, EDTA, DMSA, deferoxamine mesylate, or batimastat.

When the drug comprises the rho kinase inhibitor, the rho kinase inhibitor can comprise Y27632.

When the drug comprises the anti-hyperlipidemic agent, the anti-hyperlipidemic agent can comprise a statin (e.g., atorvastatin, cerivastatin, fluvastatin, lovastatin, mevastatin, pitavastatin, pravastatin, rosuvastatin, or simvastatin), a fibrate (e.g., bezafibrate, ciprofibrate, clofibrate, gemfibrozil, or fenofibrate), a selective inhibitor of dietary cholesterol absorption (e.g., ezetimibe), or a cholesterylester transfer protein inhibitor (e.g., anacetrapib, dalcetrapib, torcetrapib, or evacetrapib).

When the drug comprises the agent that raises HDL, the agent that raises HDL can comprise an inhibitor of proprotein convertase subtilisin/kexin type 9 (PCSK9), such as AMG145.

When the drug comprises the anti-restenosis agent, the anti-restenosis agent can comprise dexamethasone ticlopidine, clopidogrel, sirolimus, paclitaxel, zotarolimus, everolimus, or umirolimus.

When the drug comprises the antibiotic, the antibiotic can comprise actinomycin-D.

When the drug comprises the immunosuppressant, the immunosuppressant can comprise a glucocorticoid, methotrexate, azathioprine, mercaptopurine, dactinomycin, mitomycin C, bleomycin, mithramycin, ciclosporin, tacrolimus, sirolimus, an interferon, infliximab, etanercept, or adalimumab.

When the drug comprises the anti-hypertensive agent, the anti-hypertensive agent can comprise a beta adrenergic receptor antagonist (e.g., alprenolol, bucindolol, carteolol, carvedilol, labetalol, nadolol, oxprenolol, penbutalol, pindolol, propranolol, sotalol, timolol, acebutolol, atenolol, betaxolol, bisoprolol, metoprolol, or nebivolol), an angiotensin II receptor antagonist (e.g., losartan, olmesartan, valsartan, telmisartan, irbesartan, or azilsartan), or an angiotensin converting enzyme inhibitor (e.g., captopril, enalapril, lisinopril, quinapril, zofenopril, imidapril, benazepril, trandolapril, or ramipril).

When the drug comprises the diuretic, the diuretic can comprise furoseamide, amiloride, spironolactone, or hydrochlorothiazide.

When the drug comprises the anorectic, the anorectic can comprise phentermine, fenfluramine, dexfenfluramine, sibutramine, lorcaserin, topiramate, or a combination thereof.

When the drug comprises the anti-depressant, the anti-depressant can comprise imipramine, desipramine, amityptiline, paroxetine, citalopram, fluoxetine, or escitalopram.

When the drug comprises the anti-psychotic, the anti-psychotic can comprise aripiprazole, risperidone, olanzapine, quetiapine, cariprazine, lurasidone, or asenapine.

When the drug comprises the contraceptive, the contraceptive can comprise a combination of drospirenone and ethinyl estradiol.

When the drug comprises the calcimimetic, the calcimimetic can comprise cinacalcet.

When the drug comprises the biologic medical product, the biologic medical product can comprise a synthetic polysaccharide, a synthetic, partially synthetic or humanized immunoglobulin, or a recombinant therapeutic protein.

The drug or the compound can comprise a radiocontrast agent, a radio-isotope, a prodrug, an antibody fragment, an antibody, a live cell, a therapeutic drug delivery microsphere, microbead, nanoparticle, gel or cell-impregnated gel, or a combination thereof.

The compound can be capable of inhibiting, activating, or altering the function of proteins or genes in the at least one cell type.

When the drug or the compound is to be evaluated for elution from a vascular stent material, the method can further comprise testing at least one of the cell types for compatibility with, cellular adhesion to, or phenotypic modulation by the vascular stent material. The vascular stent material can be adjacent to the endothelial cells or the smooth muscle cells.

Effect on the Physiologic or Pathological Condition

In methods of testing a drug or a compound for an effect, the effect can comprise an effect on a physiologic condition or an effect on a pathological condition. For example, the effect on the physiologic condition or the pathological condition can be a toxic effect, a protective effect, a pathologic effect, a disease-promoting effect, an inflammatory effect, an oxidative effect, an endoplasmic reticulum stress effect, a mitochondrial stress effect, an apoptotic effect, a necrotic effect, a remodeling effect, a proliferative effect, an effect on the activity of a protein, such as inhibition of a protein or activation of a protein, or an effect on the expression of a gene, such as an increase in the expression of the gene or a decrease in the expression of the gene.

Multiple Cell Type Configurations for the Flow Device

The methods of the invention can further comprise perfusing culture media, factors, drugs or compounds into and out of the cell container.

When the surface within the cell culture container comprises a porous membrane suspended in the cell culture container, the method can further include the step of plating at least one cell type on a surface within the cell culture container comprising plating a first cell type on a first surface of a porous membrane, and optionally plating a second cell type on a second surface of the porous membrane, wherein the porous membrane is suspended in the cell culture container such that the first surface is proximal and in spaced relation to a bottom surface of the cell culture container, thereby defining within the cell culture container a lower volume comprising the first cell type and an upper volume comprising the optional second cell type. The porous membrane can be adapted to permit fluid communication of the cell culture media and physical interaction and communication between cells of the first cell type and cells of the optional second cell type. The shear force is applied to the second cell type or the second surface of the porous membrane in the upper volume. The method can further comprise perfusing culture media into and out of the upper volume and perfusing culture media into and out of the lower volume. The method can further comprise perfusing a drug or the compound into at least one of the upper volume and the lower volume.

When the surface within the cell culture container comprises a porous membrane suspended in the cell culture container, the method can further include the step of plating at least one cell type on a surface within the cell culture container comprising optionally plating a first cell type on a first surface of a porous membrane, and plating a second cell type on a second surface of the porous membrane, wherein the porous membrane is suspended in the cell culture container such that the first surface is proximal and in spaced relation to a bottom surface of the cell culture container, thereby defining within the cell culture container a lower volume comprising the optional first cell type and an upper volume comprising the second cell type. The porous membrane can be adapted to permit fluid communication of the cell culture media and physical interaction and communication between cells of the optional first cell type and cells of the second cell type. The shear force is applied to the second cell type in the upper volume. The method can further comprise perfusing culture media into and out of the upper volume and perfusing culture media into and out of the lower volume. The method can further comprise perfusing a drug or the compound into at least one of the upper volume and the lower volume.

The inlets and outlets in the cell culture container can be within the portions of the cell culture container defining the upper and lower volumes.

The methods described in this section can further comprise analyzing at least one of the first cell type or the second cell type for toxicity, inflammation, permeability, compatibility, cellular adhesion, cellular remodeling, cellular migration, or phenotypic modulation resulting from the drug or the compound.

These methods can further comprise plating a third cell type on a surface of the container or the first surface or second surface of the porous membrane, suspending a third cell type in the culture media within the upper volume, or suspending a third cell type in the culture media within the lower volume.

These methods can further comprise plating a fourth cell type on a surface of the container or the first or second surface of the porous membrane, suspending a fourth cell type in the culture media within the upper volume, or suspending a fourth cell type in the culture media within the lower volume.

These methods can further comprise plating a fifth cell type on a surface of the container or the first or second surface of the porous membrane, suspending a fifth cell type in the culture media within the upper volume, or suspending a fifth cell type in the culture media within the lower volume.

The first, second, third, fourth and fifth cell types can be various primary or immortalized cell types as described in the section above regarding cell types.

In each of these combinations, the cells of the third cell type, the cells of the fourth cell type or the cells of the fifth cell type can be adhered to the bottom surface of the container.

DEFINITIONS

For purposes of the inventions described herein, the term "disease-promoting condition" means an abnormal anatomical condition (i.e., the anatomy of the vasculature that deviates significantly from a medically accepted normal anatomy) that can contribute to a disease state.

The term "factor" means a biological substance that contributes to the production of a pathological or physiologic condition. Preferably, the factor provides a change in a level of a marker of the pathological or physiologic condition in the at least one plated cell type or in the culture media upon application of the shear force, as compared to the level of the marker in the at least one plated cell type or in the culture media in the absence of application of the shear force.

The term "hemodynamic" means blood flow that mimics the blood flow in vivo in a tissue of interest. For example, when arterial blood flow is of interest, the acceleration/deceleration rates, flow reversal, forward basal flow, etc. are some parameters characterizing arterial hemodynamic flow. In other tissues, such as the liver, a constant blood flow may be used to characterize in vivo hemodynamics.

The term "pathological condition" means an abnormal anatomical or physiological condition, which includes the objective or subjective manifestation of a disease.

The term "physiologic condition" means a normal medical state that is not pathologic, and can be a medical state characteristic of or conforming to the normal functioning or state of the body or a tissue or organ.

The term "subject" means an animal (e.g., a genetically modified animal or a human). The animal can include a mouse, rat, rabbit, cat, dog, or primate, or any animal typically used in medical research.

The use of the methods of the invention for particular in vitro models is described below.

Thrombosis

The present methods can be used to model thrombosis in vitro. In the coagulation cascade, thrombin converts fibrinogen to fibrin, which is deposited on the surface of a blood vessel to begin blood clot formation (thrombosis). TNFα is a potent inflammatory cytokine. TNFα and other cytokines have been shown to be potent mediators of endothelial and smooth muscle cell-derived tissue factor in vitro, which mediates fibrin deposition in the vascular wall. Circulating levels of TNFα detected in humans with cardiovascular disease are about 0.01 ng/ml to about 0.1 ng/ml. In healthy individuals, circulating levels of TNFα are much lower or undetectable, for example about 0 ng/ml to about 0.001 ng/ml.

In the methods which model thrombosis in vitro, endothelial cells are plated on a surface within a cell culture container. The surface within the cell culture container can be the surface of a porous membrane, and the porous membrane can be suspended in the cell culture container such that a first surface of the porous membrane is proximal and in spaced relation to a bottom surface of the cell culture container, thereby defining within the cell culture media a lower volume comprising the first surface of the porous membrane and an upper volume comprising the second surface of the porous membrane and the endothelial cells. Alternatively, the surface upon which the endothelial cells are plated is the bottom of the cell culture container.

One or more additional cell types can be plated on a surface within the cell culture container or suspended in the media in the cell culture container. For example, smooth muscle cells can be plated on a first surface of a porous membrane within the cell culture container and endothelial cells can be plated on a second surface of the porous membrane. The porous membrane is suspended in the cell culture container such that the first surface of the porous membrane is proximal and in spaced relation to a bottom surface of the cell culture container, thereby defining within the cell culture media a lower volume comprising the first surface of the porous membrane and the smooth muscle cells and an upper volume comprising the second surface of the porous membrane and the endothelial cells.

Monocytes, macrophages, neutrophils, endothelial progenitor cells, circulating stem cells, circulating hematopoietic cells, or leukocytes can optionally be suspended in the cell culture media within the upper or lower volume.

A shear force is applied upon the plated endothelial cells, the shear force resulting from the flow of the culture media induced by a hemodynamic flow device. The flow mimics the flow to which endothelial cells are exposed in vivo at regions of the vasculature where thrombosis is likely to occur. For example, the flow is atheroprone hemodynamic flow.

The shear force can be applied upon the plated endothelial cells for a period of time prior to the addition of one or more factors to the culture media. For example, shear force may be applied to the endothelial cells for a period of about 12 hours to about 48 hours, about 12 hours to about 36 hours, about 16 hours to about 32 hours, or about 18 hours to about 28 hours prior to the addition of one or more factors to the culture media. For instance, the shear force can be applied to the plated endothelial cells for about 24 hours prior to the addition of one or more factors. Alternatively, the shear force can be applied upon the plated endothelial cells concurrently with the addition of the one or more factors to the culture media.

One or more factors can be added to the culture media. For example, the one or more factors added to the culture media can be factors which are involved in the development or progression of thrombosis. The factor or factors are added to the media in a concentration that is within an in vivo concentration range of the factor observed in subjects with vascular disease. For example, TNFα can be added to the culture media in a concentration that is within the in vivo concentration range for TNFα which is observed in individuals with vascular disease. For example, TNFα can be added to the culture media in a concentration of about 0.005 ng/ml to about 0.2 ng/ml, about 0.01 ng/ml to about 0.1 ng/ml, about 0.03 ng/ml to about 0.07 ng/ml, or about 0.04 ng/ml to about 0.06 ng/ml. TNFα can be added to the culture media at a concentration of about 0.05 ng/ml or about 0.1 ng/ml.

Other factors can also be added to the culture media in addition to the TNFα. For example, oxidized LDL (oxLDL), glucose, or both oxLDL and glucose can be added the culture media in combination with TNFα. Such factors are added to the culture media in concentrations which are within the in vivo concentration ranges of the factors observed in subjects with vascular disease. In healthy individuals, plasma concentrations of oxLDL are generally less than about 25 μg/ml, while in patients with vascular disease, the plasma concentration of oxLDL is greater than about 25 μg to about 100 μg/ml. Thus, for example, oxLDL can be added to the culture media in a concentration of about 25 μg/ml to about 120 μg/ml, about 30 μg/ml to about 100 μg/ml, about 40 μg/ml to about 80 μg/ml, or about 25 μg/ml to about 50 μg/ml. For instance, oxLDL can be added to the culture media in a concentration of about 25 μg/ml or about 50 μg/ml.

Glucose can also be added to the culture media. Diabetes and the associated elevated glucose levels are risk factors for thrombosis. In healthy individuals, blood glucose concentrations are about 5 mM to about 10 mM, while in diabetic individuals, blood glucose concentrations range from greater than about 10 mM to about 20 mM. Thus, for example, glucose can be added to the culture media in a concentration of about 10 mM to about 25 mM, about 12 mM to about 20 mM, or about 14 mM to about 18 mM. For instance, glucose can be added to the culture media in an amount of about 15 mM or about 17.5 mM.

Application of the shear stress to the plated endothelial cells is suitably continued for a period of time following the addition of the one or more factors to the cell culture media.

Application of the shear stress can be continued, for example, for a period of about 12 hours to about 48 hours, about 18 hours to about 36 hours, or about 20 to about 30 hours, about 18 hours to about 72 hours, or about 24 hours to about 72 hours. For instance, the shear stress can be continued for about 24 hours following the addition of the one or more factors to the cell culture media.

Clot formation can then induced by incubating the endothelial cells with platelet-free plasma (PLP), calcium, and fibrinogen. This incubation can be performed under static conditions. Alternatively, the shear force application to the endothelial cells can be continued during this incubation. The cell culture media can be removed from the upper volume and the endothelial cells can subsequently be incubated with the PLP, calcium, and fibrinogen, with or without continued application of shear to the endothelial cells. Alternatively, the PLP, calcium, and fibrinogen can be added to the cell culture media in the upper volume, with or without the continued application of shear forces.

Mimicking of thrombosis can be assessed by any of a number of methods. In general, a change in a level of a marker of thrombosis in the endothelial cells or smooth muscle cells or in the culture media upon application of the shear force, as compared to the level of the marker in the endothelial cells or smooth muscle cells or in the culture media in the absence of application of the shear force, confirms mimicking of thrombosis. For example, mimicking of thrombosis can be assessed by examining fibrin deposition, by examining the expression of genes or proteins and/or secreted microparticles or proteins relevant to thrombosis, or by examining the activity of proteins relevant to thrombosis.

Atherosclerosis

The present methods can also be used to model atherosclerosis in vitro. Atherosclerosis is a focal inflammatory disease marked by inflammatory signaling within regions of the vasculature where low and oscillating shear stresses (atheroprone shear stresses) "prime" the endothelium for an inflammatory response. An important mediator of the inflammatory response is the transcription factor NFκB, which is activated by atheroprone shear stresses in vivo and in vitro. Oxidized low-density lipoprotein (oxLDL) is a hallmark of advanced atherosclerosis, is found in atherosclerotic lesions, and is elevated in the circulation of patients with cardiovascular complications. Oxidized 1-palmitoyl-2-arachidonoyl-sn-glycero-3-phosphocholine (oxPAPC), a major component of oxLDL, has not been shown to act through the canonical NFκB pathway, and although oxLDL is capable of increasing the expression of NFκB-dependent genes in vitro in static monocultures, this often requires higher concentrations of oxLDL (>100 μg/ml) than those observed in vivo in individuals with cardiovascular disease. In healthy patients plasma concentrations of oxLDL are on average 7 μg/ml, while in patients with myocardial infarction average plasma concentrations are about 28 to about 34 μg/ml, with some patients having levels of about 60 μg/ml. TNFα is also secreted in advanced atherosclerotic lesions and is elevated in the circulation of patients who have experienced myocardial infarction. TNFα is a potent, pro-inflammatory cytokine capable of activating NFκB signaling at high concentrations (>1 ng/ml).

The previous in vitro studies were all performed within static monocultures of endothelial cells. In the present methods, by contrast, atheroprone hemodynamic shear forces "prime" monocultures of endothelial cells or co-cultures of endothelial cells and smooth muscle cells by activating NFκB signaling, and the addition of oxLDL and/or TNFα, and optionally certain other factors at concentrations which are within the in vivo concentration range of the factor which is observed in patients with vascular disease further enhances NFκB activity and downstream inflammatory signaling.

In the present methods which model atherosclerosis in vitro, endothelial cells are plated on a surface within a cell culture container. The surface within the cell culture container can be the surface of a porous membrane, and the porous membrane can be suspended in the cell culture container such that a first surface of the porous membrane is proximal and in spaced relation to a bottom surface of the cell culture container, thereby defining within the cell culture media a lower volume comprising the first surface of the porous membrane and an upper volume comprising the second surface of the porous membrane and the endothelial cells. Alternatively, the surface upon which the endothelial cells are plated is the bottom of the cell culture container.

One or more additional cell types can be plated on a surface within the cell culture container or suspended in the media in the cell culture container. For example, smooth muscle cells can be plated on a first surface of a porous membrane within the cell culture container and endothelial cells can be plated on a second surface of the porous membrane. The porous membrane is suspended in the cell culture container such that the first surface of the porous membrane is proximal and in spaced relation to a bottom surface of the cell culture container, thereby defining within the cell culture media a lower volume comprising the first surface of the porous membrane and the smooth muscle cells and an upper volume comprising the second surface of the porous membrane and the endothelial cells.

Monocytes, macrophages, neutrophils, endothelial progenitor cells, circulating stem cells, circulating hematopoietic cells, or leukocytes can optionally be suspended in the cell culture media within the upper or lower volume.

A shear force is applied upon the plated endothelial cells, the shear force resulting from the flow of the culture media induced by a hemodynamic flow device. The flow mimics the flow to which endothelial cells are exposed in vivo at regions of the vasculature where atherosclerosis is likely to occur. For example, the flow is atheroprone hemodynamic flow.

The shear force can be applied upon the plated endothelial cells for a period of time prior to the addition of one or more factors to the culture media. For example, shear force can be applied to the endothelial cells for a period of about 12 hours to about 48 hours, about 12 hours to about 36 hours, about 16 hours to about 32 hours, or about 18 hours to about 28 hours prior to the addition of one or more factors to the culture media. For instance, the shear force can be applied to the plated endothelial cells for about 24 hours prior to the addition of one or more factors. Alternatively, the shear force can be applied upon the plated endothelial cells concurrently with the addition of the one or more factors to the culture media.

One or more factors can be added to the culture media. For example, the one or more factors added to the culture media can be factors which are involved in the development or progression of atherosclerosis. Such factor or factors are added to the media in a concentration which is within the in vivo concentration range of the factor observed in the individuals with vascular disease.

oxLDL can be added to the culture media in a concentration that is within the in vivo concentration range of oxLDL observed in the individuals with vascular disease. Thus, for example, oxLDL can be added to the culture media in a concentration of about 25 µg/ml to about 120 µg/ml, about 30 µg/ml to about 100 µg/ml, about 40 µg/ml to about 80 µg/ml, or about 25 µg/ml to about 50 µg/ml. For instance, oxLDL can be added to the culture media in a concentration of about 25 µg/ml or about 50 µg/ml.

Other factors can also be added to the culture media, either instead of or in combination with oxLDL. These factors include, but are not limited to: TNFα, high-density lipoprotein (HDL); triglycerides; triglyceride-rich lipoproteins including very low-density lipoprotein (vLDL), vLDL remnants, chylomicrons, and/or chylomicron remnants; low-density lipoprotein (LDL); glucose; insulin; a fatty acid; TGFβ or combinations thereof. For example, TNFα can be added to the media instead of oxLDL. Alternatively, both oxLDL and TNFα can be added to the media. HDL can also optionally be added to the media. For example, HDL can be added to the media alone, or in combination with other factors such as TNFα and oxLDL. Triglycerides or triglyceride rich lipoproteins including vLDL, vLDL remnants, chylomicrons, and/or chylomicron remnants can also optionally added to the media. Glucose can also optionally be added to the media. For example, glucose may be added to the media alone, or in combination with other factors such as TNFα. LDL or TGFβ can also be added to the media.

The factors are added to the media in concentrations which are within the in vivo concentration range of the factor observed in the individuals with vascular disease. Thus, for example, TNFα can be added to the culture media in a concentration of about 0.005 ng/ml to about 0.2 ng/ml, about 0.01 ng/ml to about 0.1 ng/ml, about 0.03 ng/ml to about 0.07 ng/ml, or about 0.04 ng/ml to about 0.06 ng/ml. For example, TNFα can be added to the culture media in a concentration of about 0.05 ng/ml or about 0.1 ng/ml.

oxLDL can be added to the media in a concentration of about 50 µg/ml.

TNFα can be added to the culture media at a concentration of about 0.05 ng/ml.

HDL can be added to the culture media in a concentration that is within an in vivo concentration range of HDL observed in individuals with vascular disease or in individuals at risk for vascular disease. HDL concentrations in individuals at risk for vascular disease are generally less than about 300 µg/ml, while HDL concentrations in healthy individuals range from greater than about 300 µg/ml up to about 2,000 µg/ml in healthy exercising patients. Thus, for example, HDL can be added to the culture media in a concentration of about 1 µg/ml to about 300 µg/ml, about 10 µg/ml to about 250 µg/ml, about 45 µg/ml to about 200 µg/ml, or about 90 µg/ml to about 150 µg/ml. For example, HDL can be added to the culture media at a concentration of about 45 µg/ml or about 90 µg/ml.

HDL may suitably be added to the culture media in combination with TNFα and oxLDL. The HDL, TNFα, and oxLDL are suitably each present at a concentration that is within the in vivo concentration ranges for these factors which are observed in individuals with vascular disease, for example, the concentration ranges listed above for each of these components. For example, HDL is added to the culture media in a concentration of 45 µg/ml or 90 µg/ml, TNFα is added to the culture media in a concentration of about 0.05 ng/ml, and oxLDL is added to the culture media in a concentration of about 50 µg/ml.

Triglycerides or triglyceride-rich lipoproteins including very low-density lipoprotein (vLDL), vLDL remnants, chylomicrons, and/or chylomicron remnants can be added to the culture media in concentrations that are within the in vivo concentration ranges for these factors which are observed in individuals with vascular disease. Triglyceride levels in healthy patients range from about 40 mg/dL to about 150 mg/dL. In patients with hypertriglyceridemia, triglyceride levels range from greater than about 200 mg/dL to about 1500 mg/dL. Thus, for example triglycerides are suitably added to the culture media in a concentration of about 175 mg/dL to about 1600 mg/dL, about 200 mg/dL to about 1500 mg/dL, about 400 mg/dL to about 1200 mg/dL, or about 600 mg/dL to about 1000 mg/dL.

Diabetes and the associated elevated levels of blood glucose are risk factors for atherosclerosis. Therefore, glucose may also suitably be added to the media in the present methods for modeling atherosclerosis in vitro. The glucose is added to the culture media at a concentration that is within the in vivo concentration range for glucose as observed in individuals with diabetes. In healthy individuals, blood glucose concentrations are about 5 to about 10 mM, while in diabetic individuals, blood glucose concentrations range from greater than about 10 mM to about 20 mM. Thus, for example, glucose is suitably added to the culture media in a concentration of about 10 mM to about 25 mM, about 12 mM to about 20 mM, or about 14 mM to about 18 mM. For instance, glucose can be added to the culture media in an amount of about 15 mM or about 17.5 mM.

Glucose can be added to the culture media together with TNFα. The glucose and TNFα are added to the culture media in concentrations that are within the in vivo concentration ranges for glucose and TNFα which are observed in individuals with diabetes or vascular disease for example, the concentration ranges listed above for each of these components. For example, glucose is suitably added to the media at a concentration of about 15 mM and TNFα is suitably added to the culture media at a concentration of 0.05 ng/ml.

When both glucose and TNFα are added to the culture media, the glucose can be added to the culture media and the cells cultured in the presence of the glucose for a period of time prior to the application of the shear stress. For example, the cells are suitably cultured in the presence of the glucose for about 1 to about 7 days, for example about 3 to about 5 days, or about 4 days prior to the application of shear stress. Shear stress can then applied to the upon the plated endothelial cells for a period of time prior to the addition of the TNFα to the culture media. For example, shear stress can be applied to the endothelial cells for a period of about 12 hours to about 48 hours, about 12 hours to about 36 hours, about 16 hours to about 32 hours, about 18 hours to about 28 hours, or about 24 hours prior to the addition of the TNFα to the culture media.

LDL or TGFβ can added to the media at concentrations that are within an in vivo concentration range of LDL or TGFβ which is observed in individuals with vascular disease. In healthy individuals, LDL levels generally range from about 50 mg/dL to about 100 mg/dL, while in individuals with atherosclerosis, LDL levels are generally above about 100 mg/dL. Thus, for example, LDL is suitably added to the culture media at a concentration of about 100 mg/dL to about 500 mg/dL, about 100 mg/dL to about 300 mg/dL, or about 100 mg/dL.

TGFβ levels in healthy individuals are generally less than about 30 ng/ml, while levels in individuals with vascular disease are about 30 ng/ml to about 100 ng/ml. Thus, TGFβ is suitably added to the culture media in a concentration of about 30 ng/ml to about 150 ng/ml, about 30 ng/ml to about 100 ng/ml, about 50 to about 100 ng/ml, or about 60 to about 90 ng/ml.

Application of the shear stress to the plated endothelial cells is suitably continued for a period of time following the addition of the one or more factors to the cell culture media. Application of the shear stress can be continued, for example, for a period of about 12 hours to about 48 hours, about 18 hours to about 36 hours, or about 20 to about 30 hours, about 18 hours to about 72 hours, or about 24 hours to about 72 hours. For instance, the shear stress can be continued for about 24 hours following the addition of the one or more factors to the cell culture media.

Mimicking of atherosclerosis can be assessed by a of a number of methods. In general, a change in a level of a marker of atherosclerosis in the endothelial cells or smooth muscle cells or in the culture media upon application of the shear force, as compared to the level of the marker in the endothelial cells or smooth muscle cells or in the culture media in the absence of application of the shear force confirms mimicking of atherosclerosis. For example, mimicking of atherosclerosis can be assessed by examining the expression of genes or proteins relevant to atherosclerosis, by examining the activity of proteins relevant to atherosclerosis, or by examining levels of secreted cytokines.

Hypertension

The methods of the present invention can also be used to model hypertension in vitro. Angiotensin II (ANG2) levels are increased in patients with cardiovascular complications, such as atherosclerosis, diabetes or hypertension. Typical concentrations of ANG2 range from about 1 nM to about 5 nM in healthy patients, and from greater than about 6 nM to about 20 nM in hypertensive patients. In addition, aldosterone is an important signaling hormone downstream of ANG2 in the renin-angiotensin system. Its levels can vary under a number of pathologies, including atherosclerosis, diabetes, and hypertension. Concentrations of aldosterone in healthy individuals are about 0.3 mM. Concentrations of aldosterone in individuals with hyperaldosteronism range from about 0.8 mM to about 1 mM.

In the methods which model hypertension in vitro, endothelial cells are plated on a surface within a cell culture container. The surface within the cell culture container can be the surface of a porous membrane, and the porous membrane can be suspended in the cell culture container such that a first surface of the porous membrane is proximal and in spaced relation to a bottom surface of the cell culture container, thereby defining within the cell culture media a lower volume comprising the first surface of the porous membrane and an upper volume comprising the second surface of the porous membrane and the endothelial cells. Alternatively, the surface upon which the endothelial cells are plated can be the bottom of the cell culture container.

One or more additional cell types can be plated on a surface within the cell culture container or suspended in the media in the cell culture container. For example, smooth muscle cells can be plated on a first surface of a porous membrane within the cell culture container and endothelial cells can be plated on a second surface of the porous membrane. The porous membrane is suspended in the cell culture container such that the first surface of the porous membrane is proximal and in spaced relation to a bottom surface of the cell culture container, thereby defining within the cell culture media a lower volume comprising the first surface of the porous membrane and the smooth muscle cells and an upper volume comprising the second surface of the porous membrane and the endothelial cells.

Monocytes, macrophages, neutrophils, endothelial progenitor cells, circulating stem cells, circulating hematopoietic cells, or leukocytes can optionally be suspended in the cell culture media in the upper or lower volume.

A shear force is applied upon the plated endothelial cells, the shear force resulting from the flow of the culture media induced by a hemodynamic flow device. The flow mimics the flow to which endothelial cells are exposed in vivo in hypertension.

The shear force can be applied upon the plated endothelial cells for a period of time prior to the addition of one or more factors to the culture media. For example, shear force can be applied to the endothelial cells for a period of about 12 hours to about 48 hours, about 12 hours to about 36 hours, about 16 hours to about 32 hours, or about 18 hours to about 28 hours prior to the addition of one or more factors to the culture media. For instance, the shear force is applied to the plated endothelial cells for about 24 hours prior to the addition of one or more factors. Alternatively, the shear force is applied upon the plated endothelial cells concurrently with the addition of the one or more factors to the culture media.

One or more factors can be added to the culture media. For example, the one or more factors added to the culture media can be factors which are involved in the development or progression of hypertension. The factor or factors are added to the media in a concentration that is within an in vivo concentration range of the factor observed in subjects with vascular disease. For example, angiotensin is suitably added to the culture media at a concentration of about 5.5 nM to about 25 nM, about 6 nM to about 20 nM, about 8 nM to about 15 nM, or about 9 nM to about 12 nM, e.g., a concentration of 10 nM.

The angiotensin may be added to the culture media either alone or in combination with another factor such as aldosterone. Alternatively, aldosterone can be added to the culture media by itself or in combination with factors other than angiotensin. When aldosterone is added to culture media, it is suitably present at a concentration of about 0.5 mM to about 1.5 mM, or about 0.8 mM to about 1 mM, e.g., at a concentration of about 1 mM.

Application of the shear stress to the plated endothelial cells is suitably continued for a period of time following the addition of the one or more factors to the cell culture media. Application of the shear stress can be continued, for example, for a period of about 12 hours to about 48 hours, about 18 hours to about 36 hours, or about 20 to about 30 hours, about 18 hours to about 72 hours, or about 24 hours to about 72 hours. For example, the shear stress can be continued for about 24 hours following the addition of the one or more factors to the cell culture media.

Mimicking of atherosclerosis can be assessed by a number of methods. In general, a change in a level of a marker of atherosclerosis in the endothelial cells or smooth muscle cells or in the culture media upon application of the shear force, as compared to the level of the marker in the endothelial cells or smooth muscle cells or in the culture media in the absence of application of the shear force confirms mimicking of atherosclerosis. For example, mimicking of atherosclerosis can be assessed by examining the expression of genes or proteins and/or secreted microparticles or proteins relevant to atherosclerosis, by examining the activity of proteins relevant to atherosclerosis, or by examining levels of secreted cytokines, chemokines, or growth factors.

Physiologic Liver Model

The present methods can also be used to create a physiologic in vitro model of the liver. In such methods, hepatocytes are plated on a surface within a cell culture container, and shear forces are applied indirectly to the plated hepatocytes. For example, the hepatocytes are suitably plated on a first surface of a porous membrane, where the porous membrane is suspended in a cell culture container such that the first surface is proximal and in spaced relation to a bottom surface of the cell culture container, thereby defining within the cell culture container a lower volume comprising the hepatocytes and an upper volume comprising a second surface of the porous membrane. The shear force is applied to the second surface of the porous membrane in the upper volume of the container. Thus, the configuration of cells in the device (FIG. 15C) is based on in vivo microarchitecture of hepatic lobules (FIG. 15A).

Figure 15A:
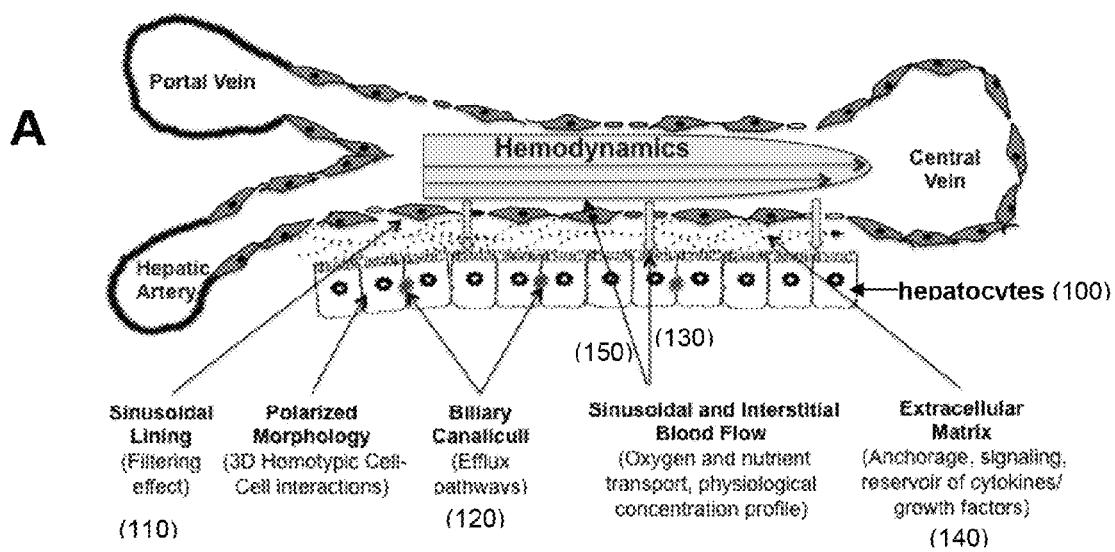
FIG. 15A is a schematic drawing of a liver sinusoid.
Figure 15B:
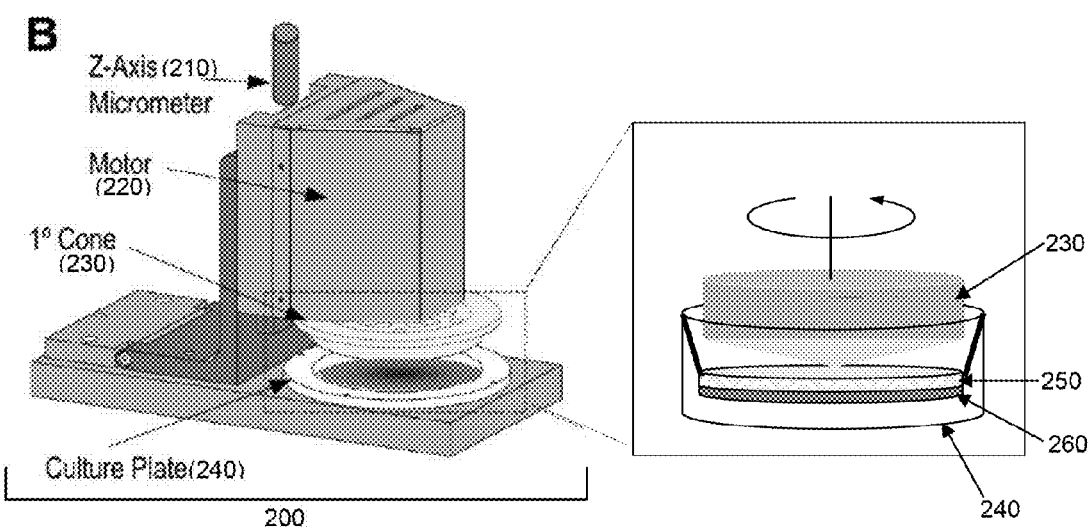
FIG. 15B depicts the cone-and-plate device and the application of indirect shear forces to hepatocytes.

As shown in FIG. 15A, in hepatic lobules in vivo, cords of hepatocytes 100 are separated from sinusoidal blood flow 150 by a filtering layer of sinusoidal endothelial cells 110 and a layer of extracellular matrix 140. The layer of extracellular matrix 140 provides for anchorage of the hepatocytes, is involved in signaling, and provides a reservoir of cytokines and growth factors. The hepatocytes 110 have a polarized morphology and biliary canaliculi 120 are present in the hepatocyte layer. Sinusoidal blood flow 150 and interstitial blood flow 130 provide for oxygen and nutrient transport.

Figure 15C:
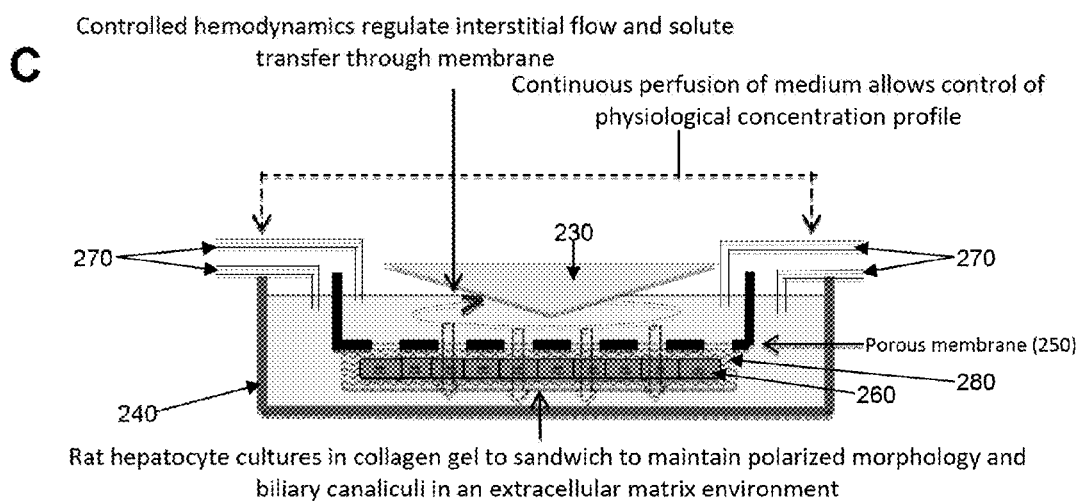
FIG. 15C depicts the plating configuration of hepatocytes in the in vitro liver model.
Figure 16:
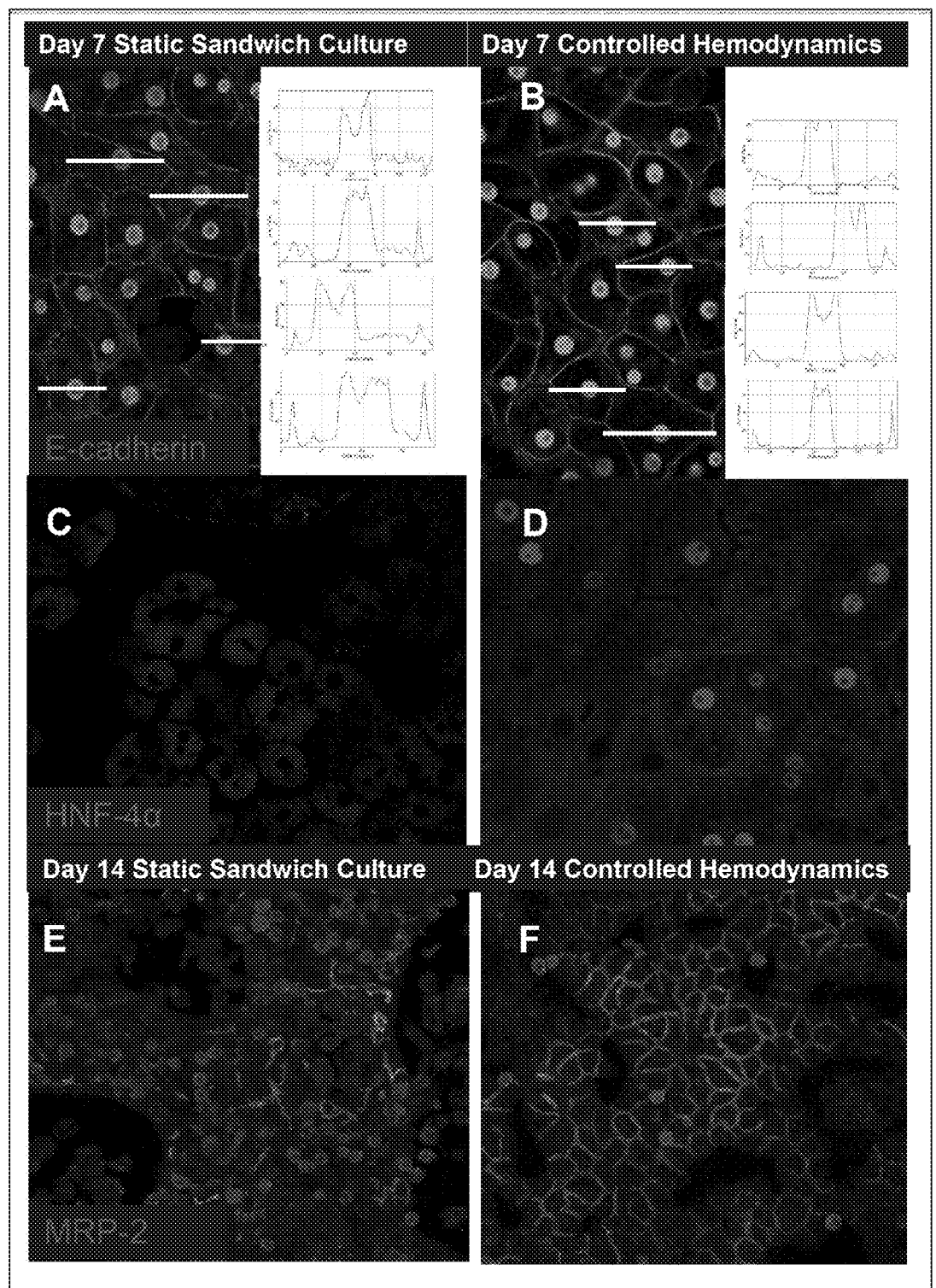
FIGS. 16A-F are exemplary fluorescent microscopy images of hepatocytes cultured under static conditions or in the presence of controlled hemodynamics.
Figure 17:
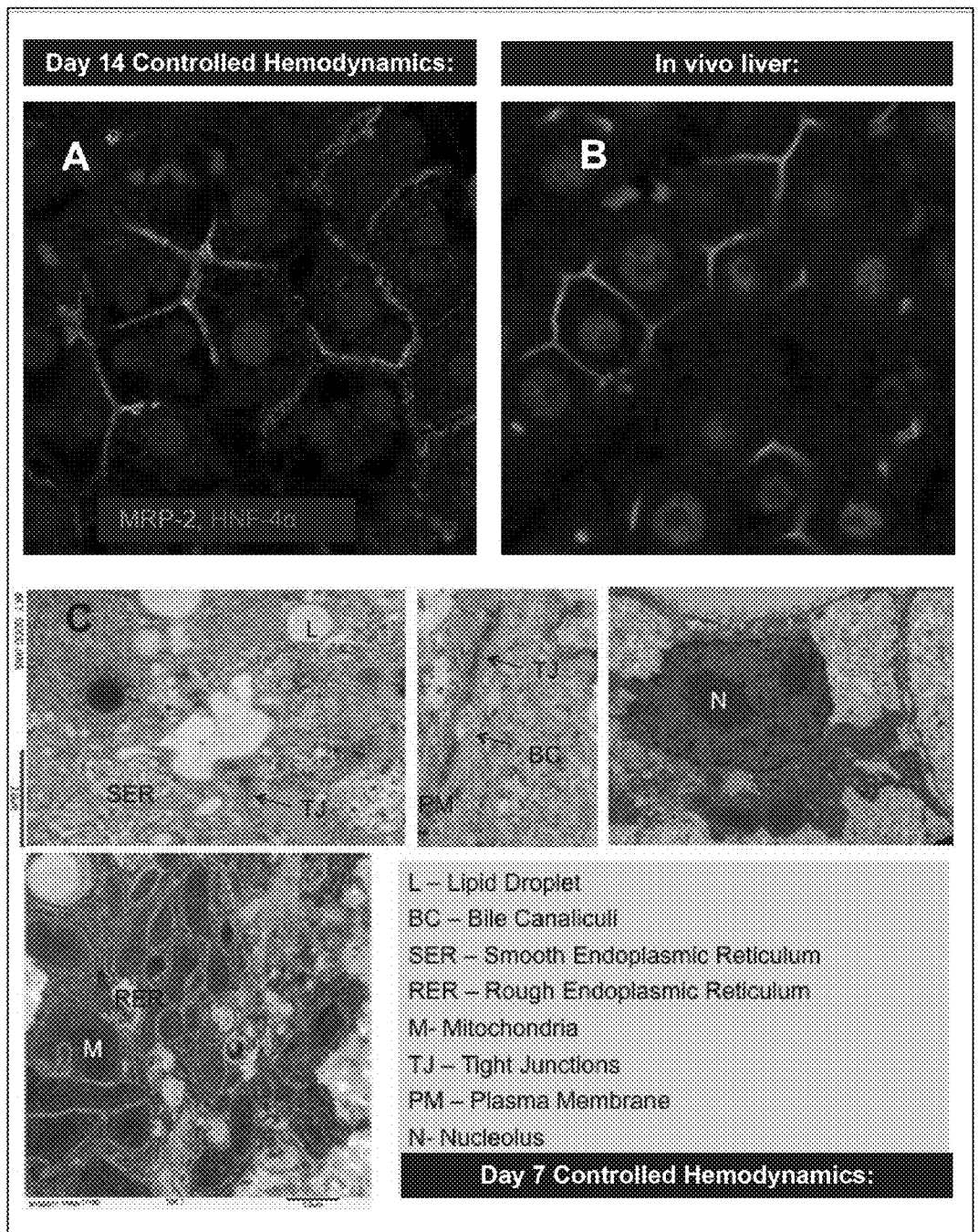
FIG. 17A is an exemplary fluorescent microscopy image of hepatocytes cultured under controlled hemodynamics.
FIG. 17B is an exemplary fluorescent microscopy image of in vivo liver.
FIG. 17C shows exemplary transmission electron microscopy images of hepatocytes cultured under controlled hemodynamics.
Figure 18:
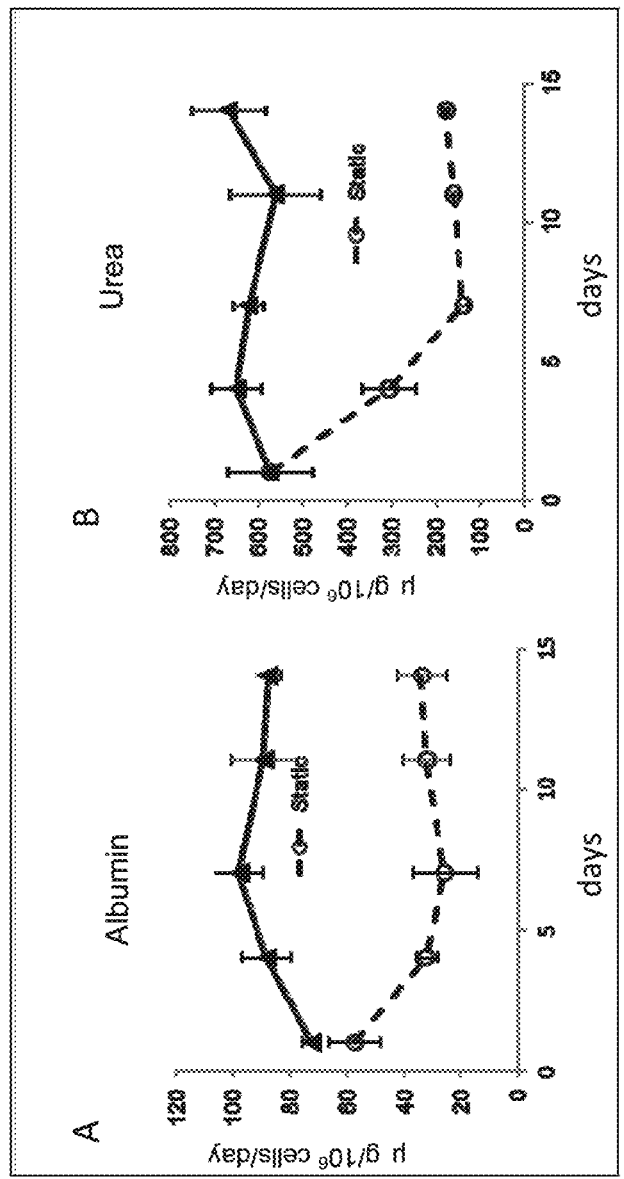
FIGS. 18A-B show exemplary data for urea and albumin secretion in hepatocytes cultured under static conditions or controlled hemodynamics.
Figure 19:
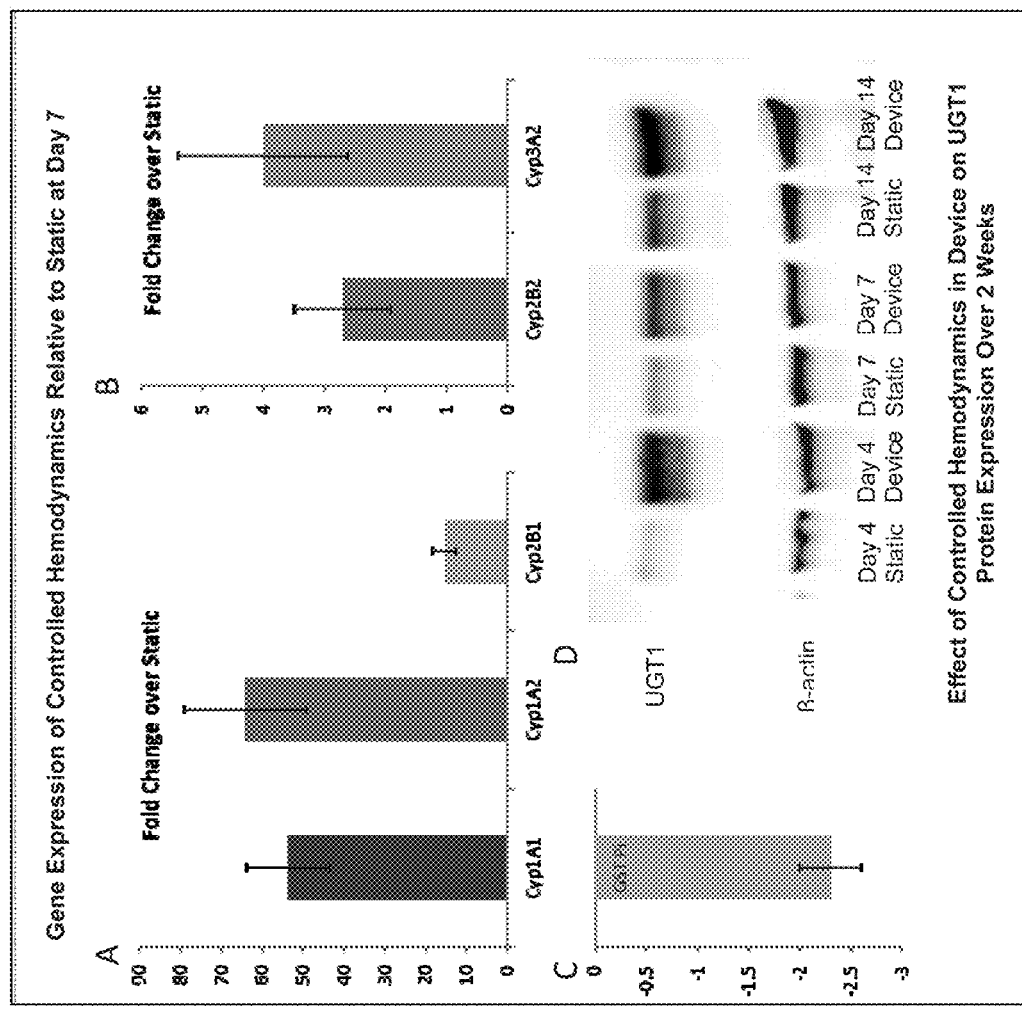
FIGS. 19A-D show exemplary metabolic gene expression data for hepatocytes cultured under static conditions or controlled hemodynamics.
Figure 20:
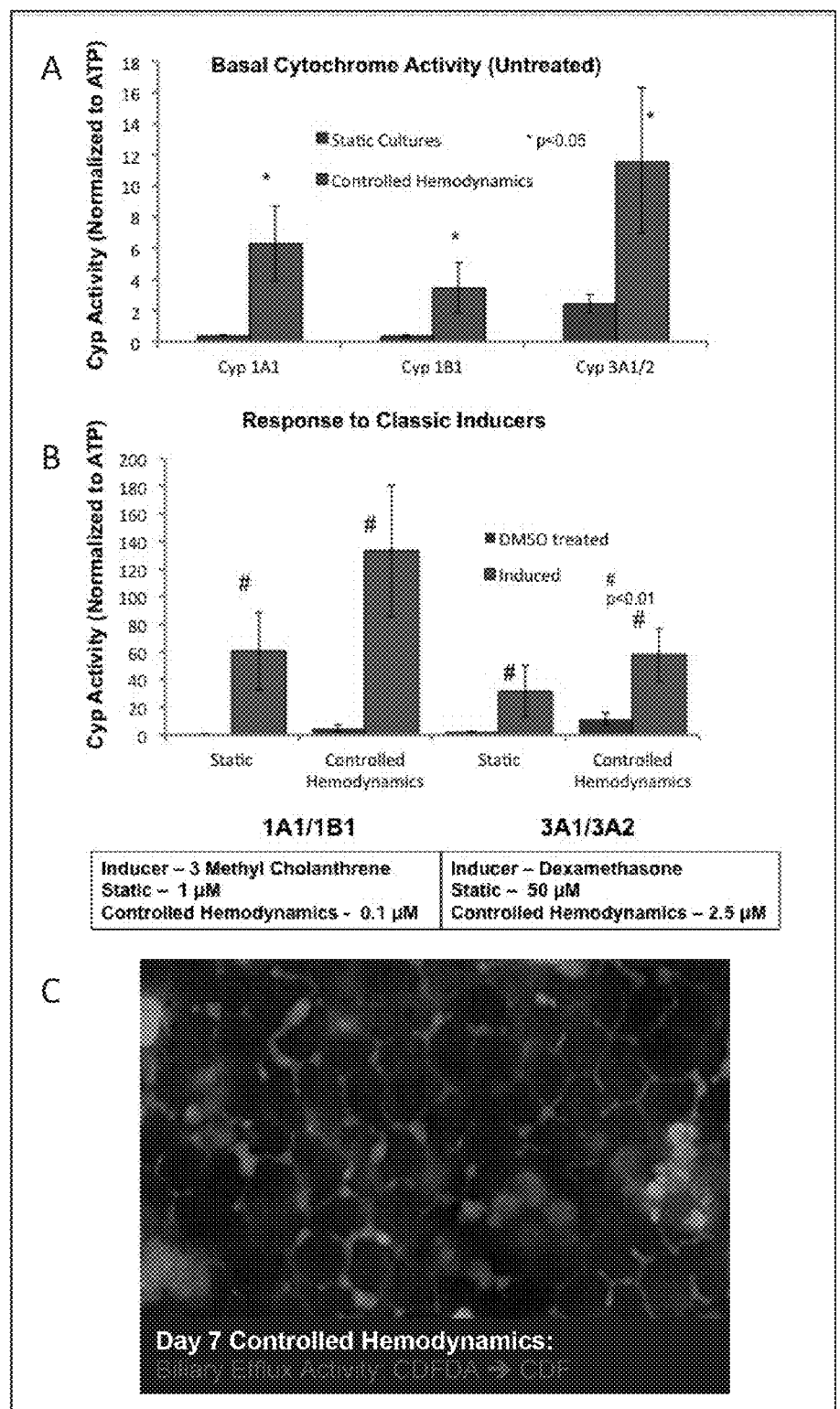
FIGS. 20A-B show exemplary cytochrome p450 activity data for hepatocytes cultured under static conditions or controlled hemodynamics.
FIG. 20C is an exemplary fluorescent microscopy image from an assay for transporter activity in hepatocytes cultured under controlled hemodynamics.

FIGS. 15B and 15C depict an exemplary configuration used in the present in vitro liver model. As shown in the inset in FIG. 15B and in FIG. 15C, hepatocytes 260 are plated on a porous membrane 250 suspended in a cell culture container 240, and a shear force applicator (shown as a cone 230 in FIGS. 15B and 15C) is used to apply a shear force upon the opposing side of the porous membrane. The shear force results from the flow of culture media in the cell culture container. The porous membrane acts analogously to the filtering layer of sinusoidal endothelial cells which is present in the liver. The hepatocytes are shielded from direct effects of flow, as they would be in vivo. Inlets and outlets 270 in the upper and lower volumes within the cell culture container allow for the continuous perfusion of culture media and for perfusion of drugs or compounds into and out of the cell culture media. Application of the shear force creates controlled hemodynamics that regulate interstitial flow and solute transfer through the porous membrane. In the in vitro models of the present invention, the hepatocytes maintain their polarized morphology and bile canaliculi.

As illustrated in FIG. 15C, at least one layer of one or more extracellular matrix components 280 (e.g., a collagen gel) can suitably be deposited on a first surface of the porous membrane. The hepatocytes 260 are then plated on the extracellular matrix component(s). One or more additional layers of the extracellular matrix component(s) can then be deposited on top of the hepatocytes, such that the hepatocytes are substantially surrounded by the extracellular matrix component(s). The extracellular matrix component suitably comprises heparan sulfate, chondroitin sulfate, keratan sulfate, hyaluronic acid, a collagen, an elastin, a fibronectin, a laminin, a vitronectin, or combinations thereof. For example, the extracellular matrix component can comprise collagen.

One or more additional cell types can be plated on a surface within the cell culture container or suspended in the culture media. For example, nonparenchymal hepatic cells are suitably plated on the second surface of the porous membrane, and the shear force is applied to the plated non-parenchymal cells. The nonparenchymal cells may include hepatic stellate cells, sinusoidal endothelial cells, Kupffer cells, or combinations thereof. The hepatocytes and nonparenchymal hepatic cells are suitably primary cells isolated from the liver of an animal, for example from the liver of a human. Alternatively, the hepatocytes and/or the nonparenchymal hepatic cells are immortalized cells.

Media is suitably continuously perfused on both sides of the porous membrane, while shear forces, derived from a range of physiological blood flow values, are continuously applied to the second surface of the porous membrane or to the plated nonparenchymal hepatic cells. The shear forces applied to the second surface of the porous membrane mimic the flow through hepatic sinusoids which occurs in vivo. The shear rate is suitably about 0.1 dynes/cm$^2$ to about 3.0 dynes/cm$^2$, about 0.2 dynes/cm$^2$ to about 2.5 dynes/cm$^2$, about 0.3 dynes/cm$^2$ to about 1.0 dynes/cm$^2$ or about 0.4 dynes/cm$^2$ to about 0.8 dynes/cm$^2$. For example, the shear rate can be about 0.6 dynes/cm$^2$. Alternatively, the shear rate can be about 2.0 dynes/cm$^2$.

In the physiologic in vitro liver model, one or more factors are present in the culture media. These one or more factors can be added to the media at concentrations which are capable of maintaining the mimicking of the physiologic liver condition in vitro for a period of time under the shear force, where the same concentrations of these factors are incapable of maintaining the mimicking of the physiologic liver condition in vitro for the period of time in the absence of the shear force. For example, the factors may comprise insulin, glucose, or a combination of insulin and glucose. The glucose and insulin are suitably present in reduced concentrations as compared to the concentrations which are typically used in static cultures (about 17.5 mM glucose and about 2μM insulin). For example, the glucose may be present in the culture media at a concentration of about 5 mM to about 10 mM, or at a concentration of about 5.5 to about 7 mM, e.g., at a concentration of about 5.5 mM. The insulin may be present in the culture media at a concentration of about 0.05 nM to about 5 nM, for example 0.1 nM to about 3 nM, or about 0.5 to about 2.5 nM, e.g., at a concentration of about 2 nM. The one or more factors are suitably added to the culture media before or concurrently with application of the shear force.

The concentrations of the one or more factors are suitably capable of maintaining the mimicking of the physiologic liver condition in vitro for at least about 7 days, at least about 14, days, at least about 21 days, at least about 30 days, or longer.

Mimicking of the physiologic liver condition can be assessed by a number of methods. In general, a change in a level of a marker of the physiologic liver condition in the hepatocytes or nonparenchymal hepatic cells or in the culture media upon application of the shear force, as compared to the level of the marker in the hepatocytes or nonparenchymal hepatic cells or in the culture media in the absence of application of the shear force confirms mimicking of the physiologic liver condition. For example, mimicking of the physiologic liver condition can be assessed by examining the hepatocytes or nonparenchymal hepatic cells for the expression of genes or proteins involved in maintaining the liver in a physiologic state (e.g., in hepatocytes, metabolic and insulin/glucose/lipid pathway genes); examining the hepatocytes for lipid accumulation; examining the hepatocytes or nonparenchymal hepatic cells for changes in differentiated function (e.g., in hepatocytes, measuring urea and albumin secretion); examining the hepatocytes or nonparenchymal hepatic cells for changes in metabolic activity (e.g., in hepatocytes, using cytochrome p450 assays) or transporter activity; or by examining the hepatocytes or nonparenchymal hepatic cells for morphological changes. The physiologic condition of the liver can also be assessed by comparing the response of the hepatocytes or nonparenchymal hepatic cells to xenobiotics, nutrients, growth factors or cytokines to the in vivo liver response to the same xenobiotics, nutrients, growth factors or cytokines.

Fatty Liver

The methods described herein can also be used to create an in vitro model of fatty liver disease. Lipid regulation within hepatocytes is a complex and dynamic process. Triglyceride buildup can occur as a consequence of increased fatty acid uptake from a high fat diet, increased peripheral lipolysis, or from increased de novo lipogenesis. Insulin and glucose are key regulators of de novo lipogenesis and contribute to increased triglyceride content within hepatocytes by stimulating triglyceride synthesis as well as inhibiting fatty acid metabolism by beta oxidation.

Non-alcoholic fatty liver disease (NAFLD) is correlated with obesity, type II diabetes, and metabolic syndrome in the presence of insulin resistance. NAFLD is characterized by hepatic steatosis (excessive lipid accumulation in the liver) that if left untreated progresses to inflammatory changes (steatohepatitis) and cirrhosis. Many animal models induce steatosis through a hyperglycemic-hyperinsulinemic environment (e.g., through use of a low fat/high carbohydrate diet to stimulate lipogenesis). However, current in vitro hepatocyte models lack an adequate insulin-glucose response to induce the same, probably on account of the superphysiological levels of insulin/glucose required to maintain hepatocytes in culture under static conditions. Such in vitro models fail to induce fatty changes in hepatocytes through insulin and glucose, perhaps due to impaired insulin responsiveness of hepatocytes under static culture conditions and rapid dedifferentiation of the hepatocytes in vitro.

By contrast, as described above with respect to the physiological liver model, hepatocytes cultured in the presence of controlled liver-derived hemodynamics and transport retain differentiated function, morphology, and response at physiological glucose and insulin levels. In this system, introducing high concentrations of insulin and glucose (a "disease milieu") induces fatty changes in the hepatocytes. Thus, controlled hemodynamics and transport produces a more physiological response to insulin and glucose in the hepatocytes, thereby inducing the fatty changes associated with steatosis in a hyperinsulemic, hyperglycemic environment as is typically seen initially under insulin resistant conditions of diabetes. In addition, hepatocytes cultured in the presence of controlled hemodynamics and transport display induction and toxicity responses to drugs at concentrations much closer to in vivo and clinical $C_{max}$ levels than static culture systems. The present system therefore provides an in vitro model of fatty liver disease.

In this model, the hepatocytes are generally plated in the same manner as described above for the physiological liver model. Hepatocytes are plated on a surface within a cell culture container, and shear forces are applied indirectly to the plated hepatocytes. For example, the hepatocytes are suitably plated on a first surface of a porous membrane, where the porous membrane is suspended in a cell culture container such that the first surface is proximal and in spaced relation to a bottom surface of the cell culture container, thereby defining within the cell culture container a lower volume comprising the hepatocytes and an upper volume comprising a second surface of the porous membrane. The shear force is applied to the second surface of the porous membrane in the upper volume of the container.

At least one layer of one or more extracellular matrix components can suitably be deposited on the first surface of the porous membrane. The hepatocytes are then plated on the extracellular matrix component(s). One or more additional layers of the extracellular matrix component(s) can then be deposited on top of the hepatocytes, such that the hepatocytes are substantially surrounded by the extracellular matrix component(s). The extracellular matrix component suitably comprises heparan sulfate, chondroitin sulfate, keratan sulfate, hyaluronic acid, a collagen, an elastin, a fibronectin, a laminin, a vitronectin, or combinations thereof. For example, the extracellular matrix component can comprise collagen.

One or more additional cell types can be plated on a surface within the cell culture container or suspended in the culture media. For example, nonparenchymal hepatic cells are suitably plated on the second surface of the porous membrane, and the shear force is applied to the plated non-parenchymal cells. The nonparenchymal cells may include hepatic stellate cells, sinusoidal endothelial cells, Kupffer cells, or combinations thereof. The hepatocytes and nonparenchymal hepatic cells are suitably primary cells isolated from the liver of an animal, for example from the liver of a human. Alternatively, the hepatocytes and/or the nonparenchymal hepatic cells are immortalized cells.

Media is suitably continuously perfused on both sides of the porous membrane, while shear forces, derived from a range of physiological blood flow values, are continuously applied to the second surface of the porous membrane or to the plated nonparenchymal hepatic cells. The shear forces applied to the second surface of the porous membrane mimic the flow through hepatic sinusoids which occurs in vivo. The shear rate is suitably about 0.1 dynes/cm$^2$ to about 3.0 dynes/cm$^2$, about 0.2 dynes/cm$^2$ to about 2.5 dynes/cm$^2$, about 0.3 dynes/cm² to about 1.0 dynes/cm² or about 0.4 dynes/cm² to about 0.8 dynes/cm². For example, the shear rate can be about 0.6 dynes/cm². Alternatively, the shear rate can be about 2.0 dynes/cm².

In the in vitro fatty liver model, one or more factors are present in the culture media. These one or more factors are added to the media at concentrations which are capable of maintaining the mimicking of fatty liver disease in vitro for a period of time under the shear force, the same concentration of factor being incapable of maintaining the mimicking of fatty liver disease for the period of time in the absence of the shear force. The factors may comprise, for example, insulin, glucose, or a combination thereof. The glucose is suitably present in the culture media at a concentration of about 10 mM to about 25 mM, about 12 mM to about 20 mM, or about 14 mM to about 18 mM, e.g., about 17.5 mM. The insulin is suitably present in the culture medium at a concentration of about 1 µM to about 3 µM, about 1.5 µM to about 2.5 µM, or about 1.8 µM to about 2.2 µM, e.g., about 2 µM. The one or more factors are suitably added to the culture media before or concurrently with application of the shear force.

The concentrations of the one or more factors are suitably capable of maintaining the mimicking of fatty liver disease condition in vitro for at least about 7 days, at least about 14, days, at least about 21 days, at least about 30 days, or longer.

Mimicking of fatty liver disease can be assessed by a number of methods. In general, a change in a level of a marker of fatty liver disease in the hepatocytes or nonparenchymal hepatic cells or in the culture media upon application of the shear force, as compared to the level of the marker in the hepatocytes or nonparenchymal hepatic cells or in the culture media in the absence of application of the shear force confirms mimicking of fatty liver disease. For example, mimicking of fatty liver disease can be assessed by examining the hepatocytes or nonparenchymal hepatic cells for the expression of genes or proteins involved in the fatty liver disease state (e.g., in hepatocytes, metabolic and insulin/glucose/lipid pathway genes); examining the hepatocytes for lipid accumulation (e.g., in hepatocytes, measuring triglyceride levels or visualizing lipid droplets); examining the hepatocytes or nonparenchymal hepatic cells for changes in differentiated function (e.g., in hepatocytes, measuring urea and albumin secretion); examining the hepatocytes or nonparenchymal hepatic cells for changes in metabolic activity (e.g., in hepatocytes, using cytochrome p450 assays) or transporter activity; or by examining the hepatocytes or nonparenchymal hepatic cells for morphological changes. Sequelae to fatty liver changes can also be assessed by measuring the changes in oxidative state of the hepatocytes and the changes in surrounding extracellular matrix composition and amount.

Having described the invention in detail, it will be apparent that modifications and variations are possible without departing from the scope of the invention defined in the appended claims.

EXAMPLES

Example 1: An In Vitro Model for Arterial and Venous Thrombosis

In the coagulation cascade, thrombin converts fibrinogen to fibrin, which is deposited on the surface of a blood vessel to begin blood clot formation (thrombosis). TNFα is a potent inflammatory cytokine. TNFα and other cytokines have been shown to be potent mediators of endothelial and smooth muscle cell-derived tissue factor in vitro, which mediates fibrin deposition in the vascular wall. Circulating levels of TNFα detected in humans with cardiovascular disease are about 0.01 ng/ml to about 0.1 ng/ml. In healthy individuals, circulating levels of TNFα are much lower or undetectable, for example about 0 ng/ml to about 0.001 ng/ml.

Methods:

Human endothelial cells were co-cultured with or without smooth muscle cells in the presence or absence of human-derived, region-specific hemodynamics. Endothelial cells were exposed to TNFα at various concentrations and incubated in human, platelet-free plasma supplemented by ALEXA FLUOR 488 (A488, a fluorescent dye)-labeled fibrinogen. Conversion of A488-fibrinogen to A488-fibrin and deposition on the endothelium was quantified by confocal microscopy.

(i) Static Monoculture Thrombosis Assay

For static monocultures of endothelial cells, endothelial cells were plated at 100,000 cells/cm² on coverslips and allowed to adhere for 24 hours. After 24 hours, media was exchanged with media containing 0 ng/ml, 1 ng/ml, 10 ng/ml, or 20 ng/ml TNFα. Cells were incubated for 4 hours at 37° C. Following incubation, media was removed and cells were washed twice with PBS. Cells were then incubated an additional 15 minutes at 37° C. with Human Platelet Free Plasma (PFP) supplemented with 37.5 µg/mL ALEXA-488 human fibrinogen, 20 µg/mL corn trypsin inhibitor, and 10 mM calcium. This protocol is depicted in FIG. 1A. After 15 minutes, the cells were fixed with 4% paraformaldehyde (PFA) and stained with 0.5 nM SYTO83 (a fluorescent nucleic acid stain) in 10 mM Tris, 1 mM EDTA buffer for 45 minutes. Coverslips were mounted onto coverglass using FLUOROMOUNT-G (a mounting agent) and imaged.

(ii) Monoculture Thrombosis Assay with Shear Stress

Endothelial cells were plated at a plating density of 100,000 cells/cm² on the porous membrane of a TRANSWELL (polycarbonate, 10 µm thickness and 0.4 µm pore diameter, no. 3419, Corning), and subjected to atheroprone or atheroprotective hemodynamic patterns using a cone-and-plate device.

Following 24 hours of shear stress application (atheroprone or atheroprotective), the media was supplemented with TNFα at a concentration of 0.05 ng/mL or 0.10 ng/mL and the shear stress was continued for an additional 24 hours, as shown in FIG. 3A. Media was then removed from both the upper and lower chambers, and endothelial cells were washed twice with PBS. Endothelial cells were then incubated for 15 minutes at 37° C. with PFP supplemented with 37.5 µg/mL ALEXA-488 human fibrinogen, 20 µg/mL corn trypsin inhibitor, and 10 mM calcium. After 15 minutes, the cells were fixed with 4% PFA and stained with 0.5 nM SYTO83 in 10 mM Tris, 1 mM EDTA buffer for 45 minutes. Small portions of the porous membrane were mounted onto coverglass using FLUOROMOUNT-G and imaged.

(iii) Coculture Thrombosis Assays with Shear Stress—Protocol A

Smooth muscle cells were plated on a first surface of the porous membrane of a TRANSWELL at a plating density of 20,000 cells/cm² and allowed to adhere to the membrane for two hours. The TRANSWELL was then inverted and the cells were incubated in reduced serum growth media (M199 supplemented with 2% FBS, 2 mM L-glutamine, and 100 U/ml penicillin-streptomycin) for forty-eight hours. Endothelial cells were then plated on a second surface of the TRANSWELL porous membrane at a density of 100,000 cells/cm², under the same media conditions and incubated for an additional twenty-four hours prior to the application of shear stress.

Following 24 hours of shear stress application (atheroprone or atheroprotective), the media was supplemented with TNFα at a concentration of 0.05 ng/mL or 0.10 ng/mL and shear stress was continued for an additional 24 hours, as shown in FIG. 3A. Media was then removed from both the upper and lower chambers, and both the endothelial cells and smooth muscle cells are washed twice with PBS. Endothelial cells were then incubated for 15 minutes at 37° C. with PFP supplemented with 37.5 µg/mL ALEXA-488 human fibrinogen, 20 µg/mL corn trypsin inhibitor, and 10 mM calcium, and fixed and imaged as described above for monocultures.

(iv) Coculture Thrombosis Assays with Shear Stress—Protocol B

Smooth muscle cells and endothelial cells were plated, subjected to atheroprone or atheroprotective shear stress, and treated with TNFα as described above for Protocol A. PFP supplemented with 37.5 µg/mL ALEXA-488 human fibrinogen and 20 µg/mL corn trypsin inhibitor was added to the upper volume to create a final concentration of PFP of approximately 27%. The PFP was further supplemented with calcium for a final concentration of 10 mM calcium in the PFP/media combination. Endothelial cells were then incubated for an additional 15 minutes at 37° C. and fixed and imaged as described above.

(v) Coculture Thrombosis Assays with Shear Stress—Protocol C

Figure 4A:
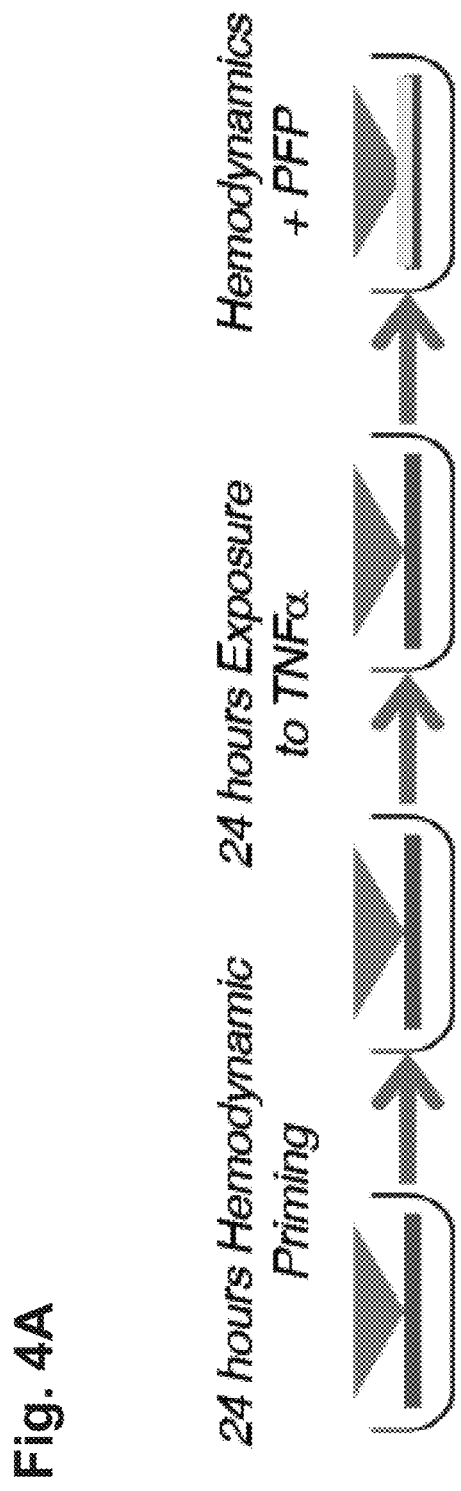
FIG. 4A depicts an exemplary protocol for a thrombosis assay performed under hemodynamic culture conditions, with continued application of shear stress during clot formation.

Smooth muscle cells and endothelial cells were plated, subjected to atheroprone or atheroprotective shear stress, and treated with TNFα as described above for Protocol A. The cone of the cone-and-plate device was then raised by about 2 mm and the in-flow/out-flow clips were removed. The cone was then lowered back to the operating height. PFP supplemented with 37.5 µg/mL ALEXA-488 human fibrinogen, 20 µg/mL corn trypsin inhibitor, was added to the upper volume to create a final concentration of PFP of approximately 27%. The PFP was further supplemented with calcium for a final concentration of 10 mM calcium in the PFP/media combination. The co-culture was then incubated for an additional 30 minutes with application of atheroprone or atheroprotective shear stress, as shown in FIG. 4A. After 30 minutes, the cell culture dish was removed from the device and media was removed from the lower volume. The endothelial cells were then fixed and imaged as described above.

Results:

(i) Static Endothelial Cell Monocultures

In cultures of endothelial cells cultured for 24 hours under static conditions and treated with TNFα for 4 hours, samples treated with 1 ng/ml TNFα demonstrated minimal fibrin deposition, whereas samples treated with 10 ng/ml or 20 ng/ml exhibited dense fibrin networks (1.17e5 vs. 2.69e7 vs. 3.61e7 mean fluorescence intensity, respectively) (FIG. 1B; insets are color images). A cross-section of the clot with the "x-axis" going from left to right and the "z-axis" going up and down was imaged in a stack as shown in the lower middle panel of FIG. 1B, to measure the height of the clot above the surface (z-axis). The mean grey value is the fluorescence intensity of each image of the stack at the designated height above the cell surface (lower far right panel of FIG. 1B).

Fibrin deposition was tissue factor-dependent and blocked by an anti-CD142 antibody. The upper panels of FIG. 1C show fibrin deposition in the presence of an antibody to tissue factor (anti-CD142, left) or a control antibody (IgG1K, right). The lower panels show staining of nuclei in the same fields, demonstrating the presence of cells.

Thus, under static conditions, endothelial cells require activation by TNFα to initiate the clotting cascade. This activation is dependent on tissue factor activity and TNFα concentrations that are approximately 200-fold higher than physiological levels.

(ii) Endothelial Cell/Smooth Muscle Cell Co-Cultures Subjected to Shear

Figure 2B:
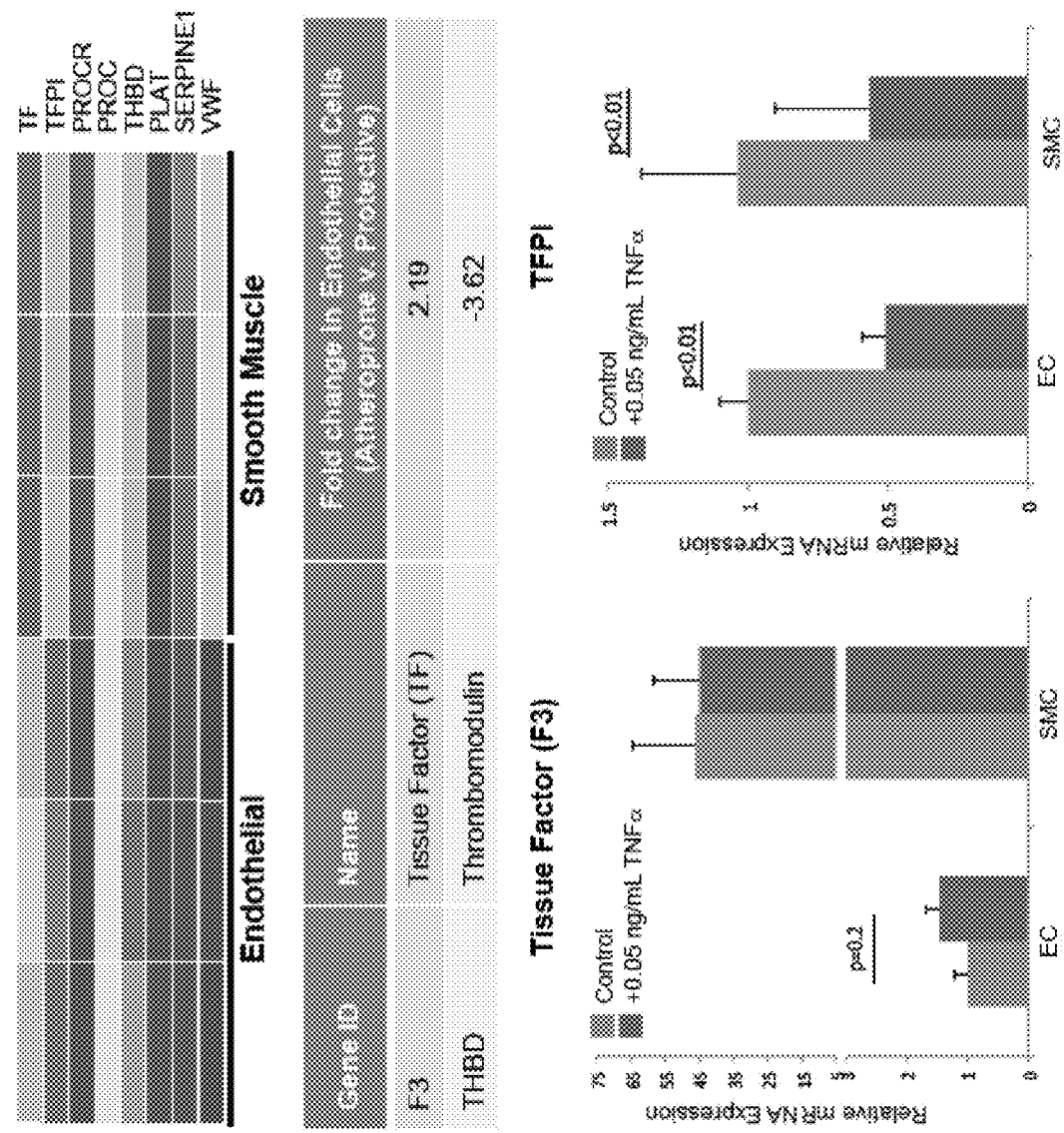
FIG. 2B shows exemplary heat maps of gene expression of genes relevant to thrombosis in endothelial cells and smooth muscle cells grown under atheroprone or atheroprotective hemodynamic flow conditions.

FIG. 2B depicts a heat map of relative gene expression in endothelial and smooth muscle cells (grown under atheroprone or atheroprotective conditions; see FIG. 2A) of several genes relevant to thrombosis. The relative changes in gene expression of Tissue Factor (F3) and Thrombomodulin (THBD) are presented below the heat map. Atheroprone hemodynamics up-regulate Tissue Factor (F3) compared to atheroprotective shear stress. Further, thrombomodulin, which binds thrombin and inhibits the clotting cascade, is down-regulated. In addition, TNFα stimulation reduces Tissue Factor Pathway Inhibitor (TFPI) in both endothelial and smooth muscle cells.

Figure 3B:
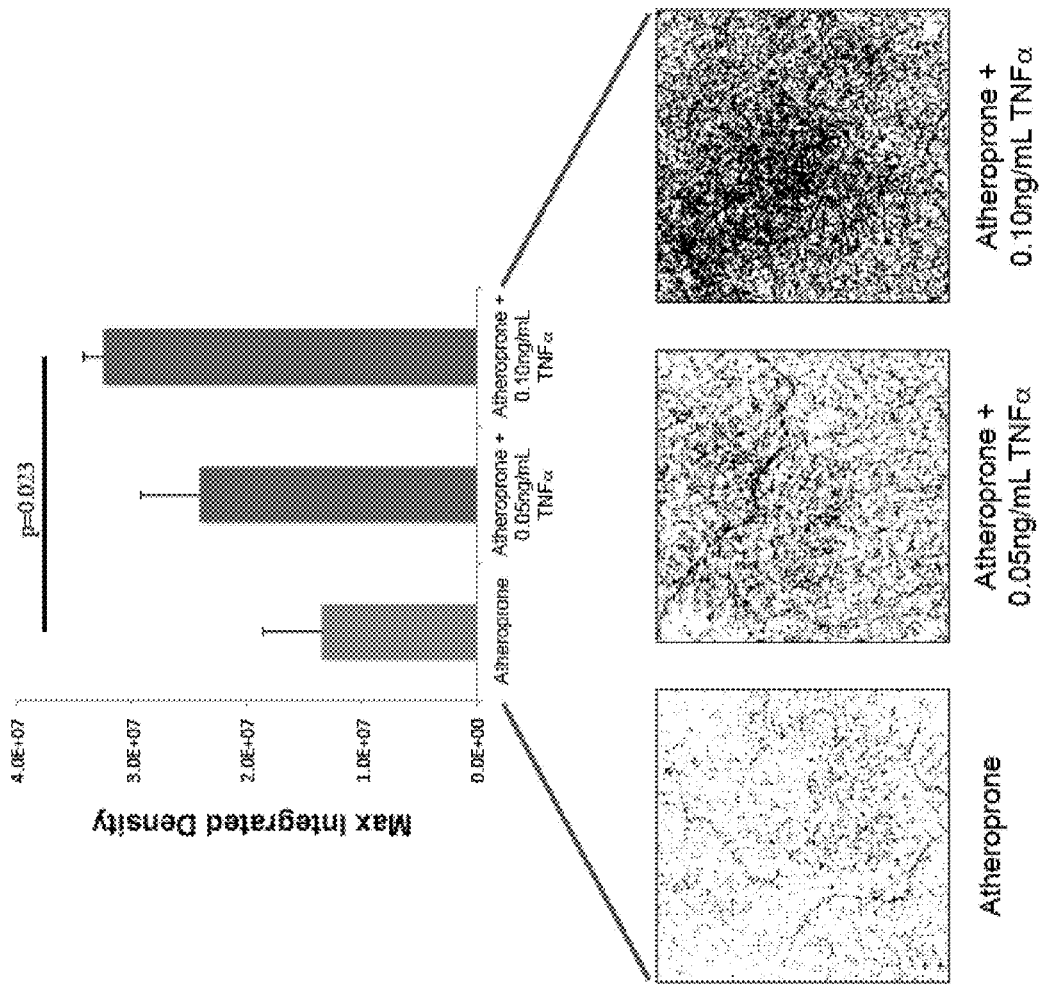
FIG. 3B shows exemplary fluorescent microscopy results from a thrombosis assay performed under hemodynamic culture conditions.

Endothelial/smooth muscle cell co-cultures primed with inflammatory-prone hemodynamics derived from the internal carotid sinus and treated with 0.05 ng/ml TNFα deposited a dense fibrin network (1.9e7 mean fluorescence intensity) (FIG. 3B; data generated using Protocol A as described above). Thus, atheroprone hemodynamics prime the endothelial layer to be more responsive to cytokine activation, allowing for 100- to 200-fold lower levels of TNFα to induce fibrin deposition as compared to static cultures.

Identical experiments in which only endothelial cells were cultured yielded similar results (data not shown), demonstrating that the result is hemodynamic-specific and not a consequence of the presence of smooth muscle cells.

FIG. 4B shows results from experiments performed according to Protocol C as described above, where shear stress was maintained during clot formation, more closely mimicking physiological conditions. The two upper panels in FIG. 4B show stacked images for each condition and are slightly angled to show the topography of the clot. The bar graph in FIG. 4B shows the fluorescence intensity of each of these images at the indicated distance above the cell surface. Representative images at 6 µm and 21 µm above the cell surface are shown in the lower right-hand panel of FIG. 4B.

Conclusions:

Static monoculture of endothelial cells requires significantly elevated levels of TNFα that are not relevant to human circulating blood concentrations in order to induce fibrin deposition. Atheroprone hemodynamics up-regulate clotting factors and down-regulate clotting inhibitors compared to atheroprotective hemodynamics. Hemodynamic priming of endothelial cells in vitro shifts the dose-dependent fibrin deposition response to TNFα into a concentration range similar to the circulating levels of TNFα observed in humans with cardiovascular disease, two orders of magnitude below that required to induce fibrin deposition in static endothelial cell cultures.

Example 2: An In Vitro Model for Atherosclerosis (i) Effects of oxLDL in a Hemodynamic Environment
(a) Methods To oxidize LDL, native LDL (nLDL) was dialyzed with PBS for 24 hours to remove EDTA. The LDL was then dialyzed for 3 days in PBS containing 13.8 µM CuSO₄. The LDL was then dialyzed with PBS containing 50 µM EDTA for an additional 24 hours. A relative electrophoretic migration number was used to confirm the oxidation level for each batch. Upon completion of oxidation, the oxLDL was stored under nitrogen at 4° C. until use.

Smooth muscle cells were plated on a first surface of the porous membrane of a TRANSWELL (polycarbonate, 10 µm thickness and 0.4 µm pore diameter, no. 3419, Corning) at a plating density of 20,000 cells/cm$^2$ and allowed to adhere to the membrane for two hours. The TRANSWELL was then inverted and the cells were incubated in reduced serum growth media (M199 supplemented with 2% FBS, 2 mM L-glutamine, and 100 U/ml penicillin-streptomycin) for forty-eight hours. Endothelial cells were then plated on a second surface of the TRANSWELL porous membrane at a density of 100,000 cells/cm$^2$, under the same media conditions and incubated for an additional twenty-four hours prior to the application of shear stress.

Figure 5:
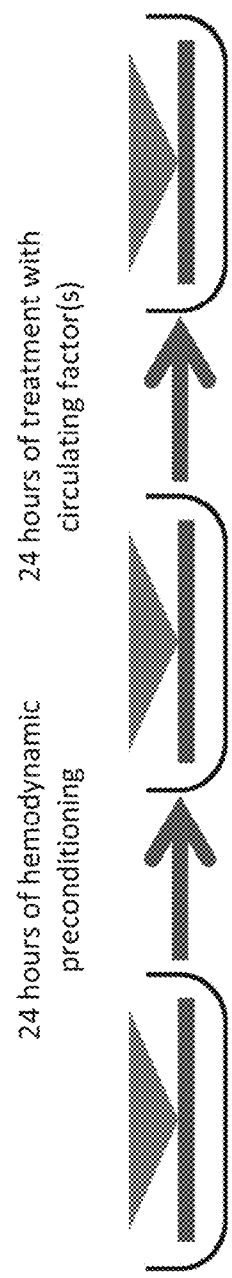
FIG. 5 shows a protocol for assays wherein co-cultures of endothelial cells and smooth muscle cells are subjected to hemodynamic preconditioning, followed by treatment with one or more factors.

Following 16-24 hours of shear stress preconditioning with atheroprotective or atheroprone hemodynamic forces, oxLDL was added to upper volume (containing the endothelial cells) at a concentration of 10-50 µg/ml (FIG. 5). In devices not receiving oxLDL, nLDL was added to the upper volume at the same concentration and used as a vehicle control. This concentration of oxLDL is similar to plasma concentrations of oxLDL observed in patients with cardiovascular disease. Shear stress application was continued for an additional 24 hours in the presence of oxLDL.

Five different donor pairs were used to analyze the oxLDL (50 µg/ml) response compared to nLDL (50 µg/ml) within the atheroprone hemodynamic environment in endothelial cells and smooth muscle cells. Upon completion of the experiment, RNA was collected for gene array analysis. Significant genes were considered using an FDR of 0.01. Gene expression results are reported as the relative expression of the gene as compared to the expression of β-2 microglobulin (B2M). Protein expression results are reported as the relative expression of the protein as compared to the expression of actin. Activity of NFκB was assessed using an adenovirus NFκB-luciferase (Ad-NFκB-luc) reporter infected in ECs and SMCs.

(b) Results

Figure 6:
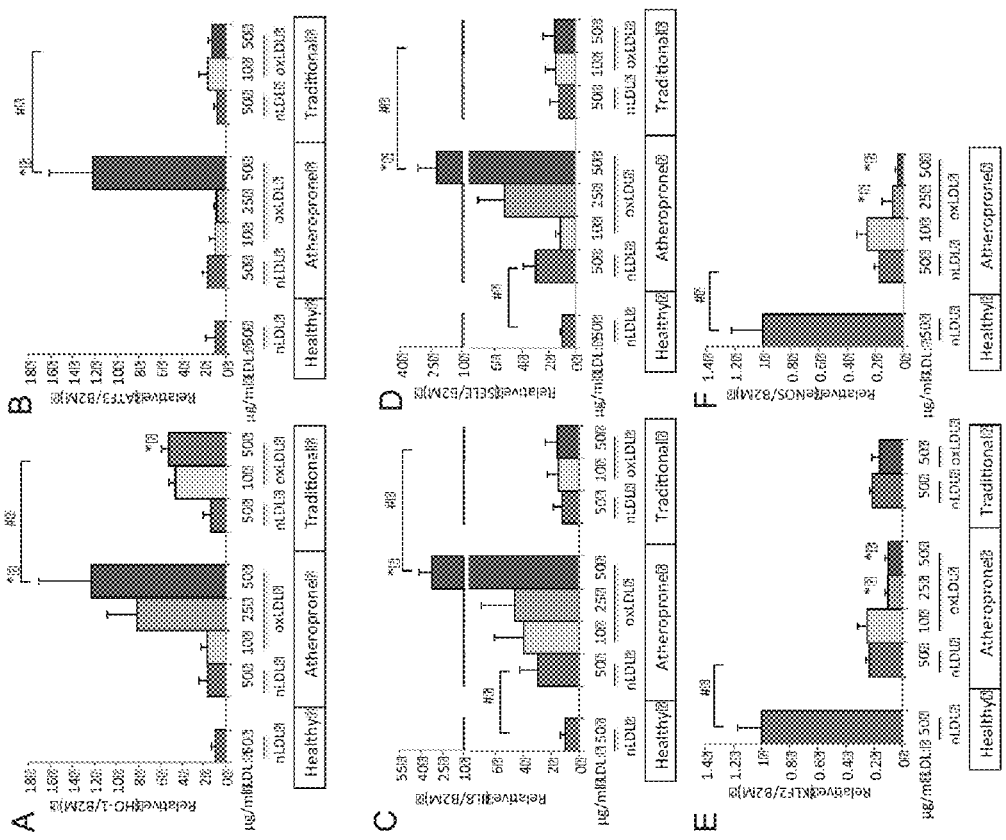
FIGS. 6A-F depict exemplary gene expression data for assays using oxLDL.

As shown in FIG. 6, the effect of different concentrations of oxLDL on gene expression was compared between the atheroprone hemodynamic environment and traditional static cultures. These data were further compared to "Healthy" hemodynamic conditions without oxLDL. (In FIG. 6, "Healthy" indicates the application of atheroprotective hemodynamics, "Atheroprone" indicates the application of atheroprone hemodynamics; and "Traditional" indicates the application of static culture conditions. mean±SE, n=4, *p<0.05, t-test.) The hemodynamic environment significantly regulated many pro- and anti-inflammatory genes (IL8, E-selectin (SELE), KLF2, eNOS). The response to the addition of oxLDL compared to nLDL created dose-dependent changes in gene expression that was dependent on the hemodynamic environment.

In particular, previous published studies in traditional static cultures have shown that HO-1 and ATF3 are "classic" oxLDL-sensitive genes. As shown in FIGS. 6A and 6B oxLDL activates these genes at much higher levels under the atheroprone conditions compared to traditional static conditions.

Unique to atheroprone conditions, oxLDL was also found to activate inflammatory genes such as IL8 and E-Selectin (SELE), which were not regulated in traditional static cultures (FIGS. 6C and 6D). Interestingly, oxLDL reduced atheroprotective signaling (eNOS and KLF2) (FIGS. 6E and 6F).

FIG. 7 illustrates changes in protein expression in response to oxLDL treatment within the atheroprone hemodynamic environment. In agreement with gene expression, oxLDL treatment resulted in elevated VCAM-1 protein expression (pro-inflammatory; FIG. 7A) and reduced phosphorylation of atheroprotective eNOS signaling (FIG. 7B). Further, oxLDL treatment resulted in increased levels of secreted cytokines, such as IL6, IL8, and MCP-1 (FIGS. 7C-7E). In FIG. 7, mean±SE, n=4, *p<0.05, t-test.

Figure 8:
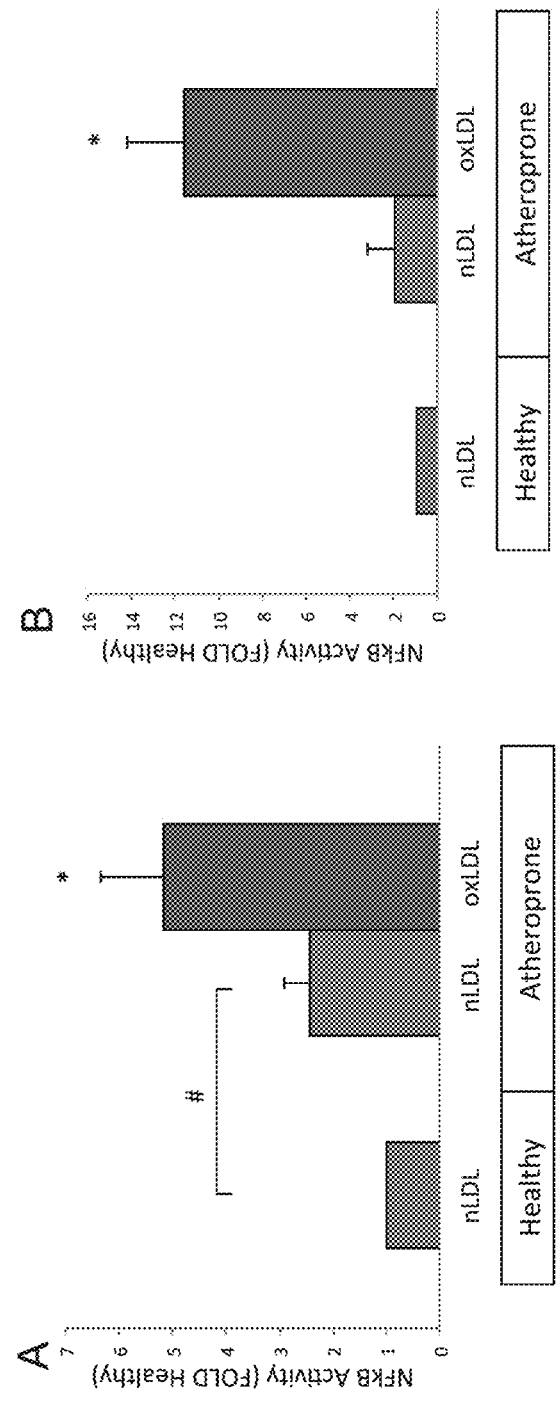
FIG. 8 depicts exemplary data showing NFκB activity in response to oxLDL.

Because many of the affected genes and proteins by oxLDL are NFκB-dependent, NFκB activity was assessed using a luciferase reporter in endothelial cells and smooth muscle cells. FIG. 8 shows that in endothelial cells (FIG. 8A), atheroprone hemodynamics "prime" the cells for elevated NFκB activity compared to the healthy condition. This response is further heightened with treatment of oxLDL. Likewise, smooth muscle cells (FIG. 8B) showed elevated NFκB signaling with treatment of oxLDL (even though the oxLDL was added to the upper volume, which contained only endothelial cells). In FIG. 8, mean±SE, n=4, *p<0.05, t-test.

Figure 9:
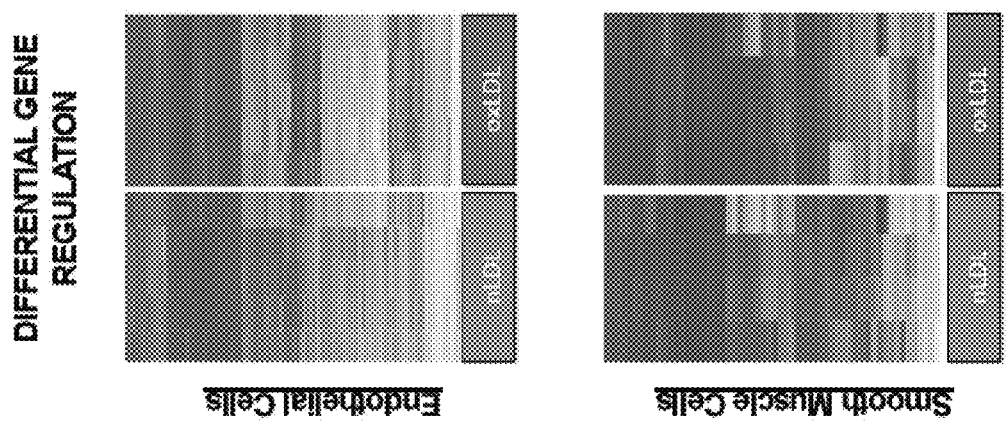
FIG. 9 shows exemplary differential gene regulation data for cells treated with oxLDL.

Full genome arrays were used to interrogate gene expression differences in ECs and SMCs within the atheroprone condition between 50 µg/ml nLDL and 50 µg/ml oxLDL. FIG. 9 shows heatmaps for gene expression across the two different conditions for 5 donors (endothelial cells) or 4 donors (smooth muscle cells). Using stringent statistical cut-off criteria (SAM and wLPE methods), 688 genes were regulated in endothelial cells and 304 in smooth muscle cells as compared to cells treated with nLDL. These gene panels were enriched with shear stress-regulated, pro-(VCAM, E-Selectin) and anti-(KLF2, eNOS) inflammatory genes.

In sum, oxLDL is known to activate some pathways (HO-1, ATF3), but not others (E-Selectin, IL6) in traditional static cultures. Here, it was found that the addition of oxLDL within the atheroprone hemodynamic environment preferentially reduced endothelial "atheroprotective" signaling (KLF2, eNOS expression and phosphorylation), and further activated pro-inflammatory signaling, including adhesion molecule expression and cytokine secretion. Though not directly exposed to either atheroprone shear stress or LDL, many genes were regulated by these conditions in the underlying SMCs in this coculture system, including inflammatory genes. Investigating the role of oxLDL within the context of physiologic shear stress was found to enhance the atheroprone-regulated gene profile towards a more pro-inflammatory phenotype. These conditions mimic vessel wall inflammation found in human arteries and provide an ideal environment for testing drugs intended for treating advanced atherosclerosis.

(ii) Effects of TNFα in a Hemodynamic Environment (a) Methods

TNF-α is a potent inflammatory cytokine. The concentration of TNF-α is modulated by severity of patients with chronic heart failure to levels of ~0.02 ng/ml, while in healthy individuals TNF-α is typically much lower or undetectable. As noted above, circulating levels of TNFα detected in humans with cardiovascular disease are about 0.01 ng/ml to about 0.1 ng/ml. In healthy individuals, circulating levels of TNFα are much lower or undetectable, for example about 0 ng/ml to about 0.001 ng/ml. By comparison, static in vitro experiments typically use TNFα concentrations of 1-10 ng/ml.

Smooth muscle cells and endothelial cells were plated on first and second surfaces of a porous membrane of a TRANSWELL in the same manner as described above for the oxLDL experiments.

Following 24 hours of shear stress preconditioning with atheroprotective or atheroprone hemodynamic forces, TNFα was added to upper volume (containing the endothelial cells) at a concentration of 0.05-1 ng/ml (see FIG. 5). This concentration of TNFα is similar to plasma concentrations of TNFα observed in patients with cardiovascular disease. Shear stress application was continued for an additional 24 hours in the presence of TNFα.

(b) Results

Figure 10:
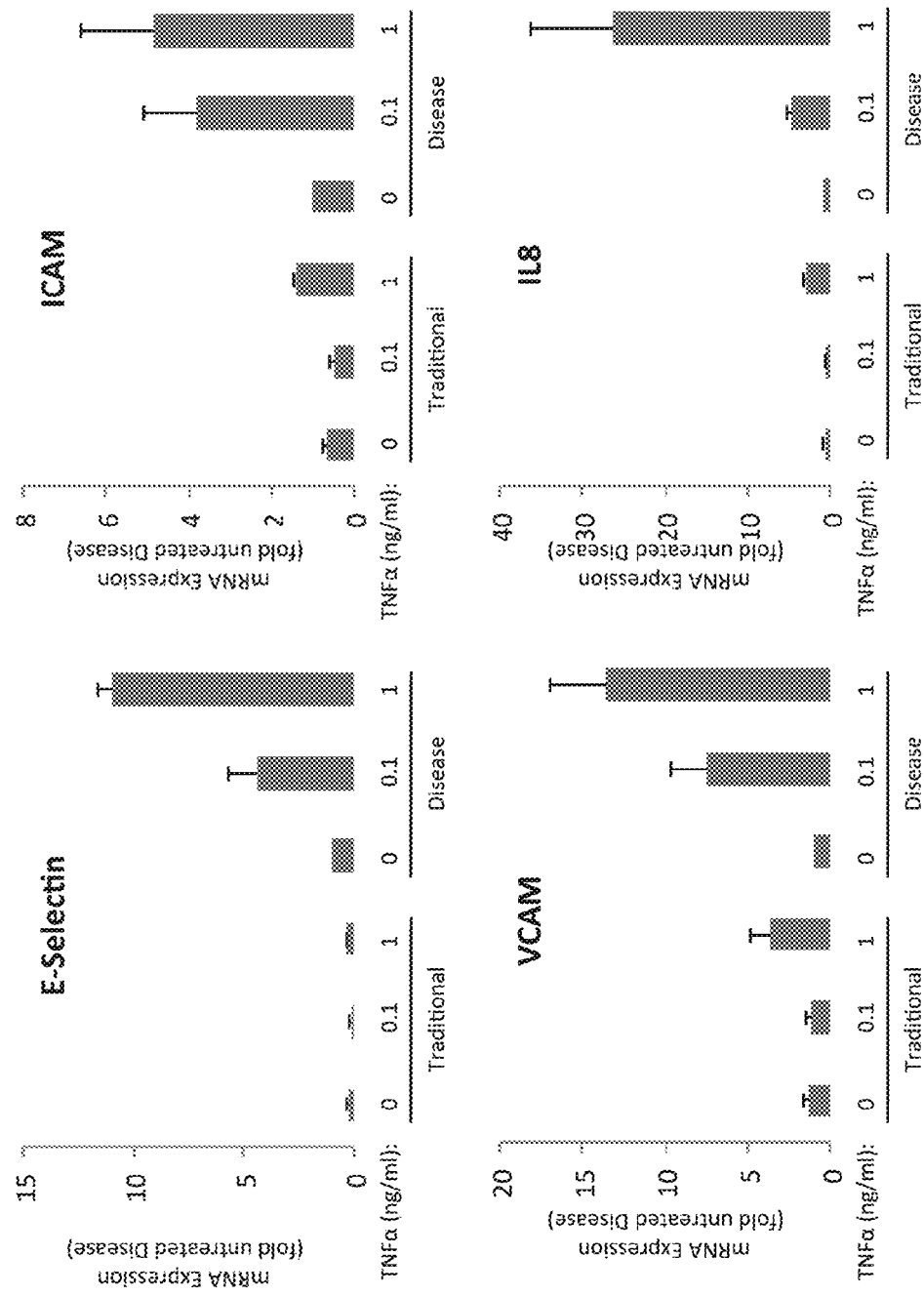
FIG. 10 shows exemplary data showing gene expression in response to TNFα.

As shown in FIG. 10, it was found that hemodynamic priming for 18-24 hours sensitized endothelial cells and smooth muscle cells to lower levels of TNFα compared to traditional static cultures. Treating endothelial cells with 0.1-1 ng/ml TNFα induced an inflammatory response that was not seen at the same levels in static cultures, as illustrated by increased expression of E-Selectin, ICAM, VCAM, and IL8 in the cultures subjected to atheroprone hemodynamic forces. In FIG. 10, "traditional" indicates that the cells were cultured under static conditions, and "disease" indicates that the cells were subjected to atheroprone hemodynamic forces. The data in FIG. 10 are shown as mean±SE, n=4, *$p<0.05$, t-test.

(iii) Effects of oxLDL and TNFα in a Hemodynamic Environment (a) Methods

To emulate more inflammatory stages of atherosclerosis, it is desirable to combine multiple circulating factors to better emulate the complexity found within human blood vessels. For these experiments, endothelial cells and smooth muscle cells were plated in the same manner as described above and subjected to atheroprone shear stress preconditioning for 18-24 hours. The media in the upper volume was then exchanged for media containing 0.05 ng/ml TNFα and 50 μg/ml of oxLDL. Media containing only 50 μg/ml of nLDL was used as a control.

Following 24 hours of shear stress preconditioning with atheroprotective or atheroprone hemodynamic forces, 50 μg/ml of oxLDL and 0.05 ng/ml of TNFα were added to upper volume (containing the endothelial cells). This concentration of TNFα is similar to plasma concentrations of TNFα observed in patients with cardiovascular disease. In devices not receiving oxLDL, nLDL was added to the upper volume at the same concentration and used as a vehicle control. Shear stress application was continued for an additional 24 hours in the presence of TNF-α and oxLDL (see FIG. 5). Gene expression analysis was performed using RT-PCR.

(b) Results

Figure 11:
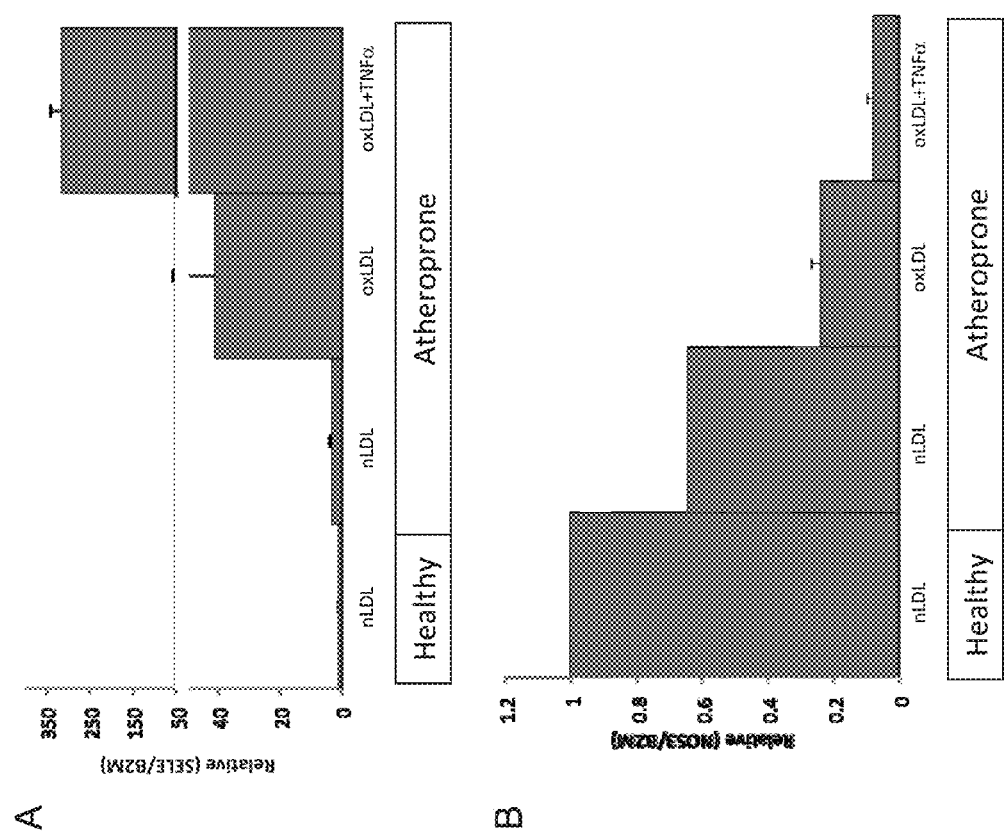
FIGS. 11A-B show exemplary gene expression data in response to treatment with oxLDL and TNFα.

The combination of these factors (oxLDL and TNFα) have shown both synergistic increases in gene and protein expression, while also providing broader signaling activation than by either oxLDL or TNFα alone. FIG. 11A shows elevated gene expression of E-Selectin (SELE), a pro-inflammatory adhesion molecule compared to oxLDL alone. Thus, similar to the results shown in FIG. 6, oxLDL causes higher levels of E-Selectin gene expression than controls treated with nLDL. The addition of TNFα with oxLDL caused even greater levels of inflammatory gene expression.

In addition, the atheroprotective signaling through eNOS transcription (NOS3) is strongly reduced in inflammatory conditions. This response was amplified with the combination of atheroprone shear stress+oxLDL+TNFα (FIG. 11B). Thus, eNOS gene expression (NOS3) was reduced by oxLDL, but with the combination of TNF-α and oxLDL, the atheroprotective signaling is even further repressed. The end product is a system with a higher basal level of inflammatory signaling compared to the atheroprone alone.

(iv) Effects of High-Density Lipoprotein (HDL) in a Hemodynamic Environment (a) Methods An additional component of plasma cholesterol distinct from nLDL or oxLDL is HDL. To assess the effects of HDL in the hemodynamic environment, endothelial cells and smooth muscle cells were plated as described above and subjected to 24 hours of shear stress preconditioning with atheroprone hemodynamic forces. HDL was then added to the upper volume at a concentration of 45-1,000 μg/ml. This broad range reflects the broad range of HDL concentrations that can exist within human patients. HDL concentrations in individuals at risk for vascular disease are generally less than about 300 μg/ml, while HDL concentrations in healthy individuals range from greater than about 300 μg/ml up to about 2,000 μg/ml in healthy exercising patients.

In additional experiments, endothelial cell/smooth muscle cell co-cultures plated as described above were preconditioned for 16 hours with hemodynamic shear stress. From hours 16-24 the cells were additionally primed with 0.05 ng/ml TNFα and 50 μg/ml of oxLDL (compared to a vehicle control containing 50 μg/ml nLDL) in the upper volume. At 24 hours, 45 μg/ml or 90 μg/ml HDL was added to the media in the upper volume and hemodynamic shear stress was continued for the next 24 hours (hours 24-48).

(b) Results

Addition of HDL at 45 μg/ml or 90 μg/ml activates many atheroprotective genes while blocking activation of pro-inflammatory genes and proteins.

(v) Effects of Triglycerides Containing Lipoproteins in a Hemodynamic Environment Triglycerides (TG) are an important biomarker of cardiovascular disease. Several species of triglyceride-rich lipoproteins (TRLs) including very low-density lipoprotein (vLDL) and vLDL remnants, as well as chylomicron (CM) remnants appear to promote atherogenesis independently of LDL. TG levels in healthy patients range from about 40 to about 150 mg/dL. In patients with hypertriglyceridemia, TG levels range from greater than about 200 mg/dL to about 1500 mg/dL.

Endothelial cell/smooth muscle cell co-cultures can be plated as described above and preconditioned for 24 hours with atheroprone shear stress. TG-containing lipoproteins, containing very low density lipoprotein (vLDL), chylomicrons (CM), and remnant particles for vLDL and CM can be added to the system at 500 mg/dL, a concentration representative of levels seen in patients with hypertriglyceridemia. Treatment concentrations of each component are based on the fraction of TGs each of these components represent: vLDL makes up about 53% of TGs, thus 0.53× 500 mg/dL=265 mg/dL; CM makes up about 38% of TGs, thus 0.38×500 mg/dL=190 mg/dL for hypertriglyceridemia conditions. This can be compared to control conditions based on circulating levels of triglycerides of 150 mg/dL (representative of levels seen in healthy patients) of 80 mg/dL for vLDL and 57 mg/dL of CM. After 24 hours of hemodynamics preconditioning, vLDL, CM, or vLDL+CM can be added for the remaining 24 hours of the experiment. vLDL and CM remnant-like proteins (RLPs) can be generated by treating the same concentrations listed above with Lipoprotein Lipase (LPL). RLPs can be added individually or in combination with vLDL and/or CM.

(vi) Effects of Glucose in Combination with TNFα in a Hemodynamic Environment (a) Methods Diabetes is a disease characterized altered insulin and glucose homeostasis. In healthy individuals, blood glucose concentrations are about 5 to about 10 mM, while in diabetic individuals, blood glucose concentrations range from greater than about 10 mM to about 20 mM. Diabetes and associated elevated glucose levels are risk factors for atherosclerosis.

Endothelial cells and smooth muscle cells were plated as described above. For a period of four days prior to the application of shear stress, the endothelial cells and smooth muscle cells were cultured in the presence of elevated glucose (15 mM) or basal glucose (5 mM) conditions found in most media formulations, supplemented with mannose as a vehicle control for glucose to account of potential changes in osmolarity. Cultures were then preconditioned for 24 hours under atheroprone hemodynamics, followed by exposure to 0.05 ng/ml TNFα (a concentration similar to circulating levels observed in patients with cardiovascular disease) for an additional 24 hours. Upon completion of the experiment, RNA was collected for gene expression analysis via RT-PCR. In some experiments, endothelial cells were infected with adenovirus with NFκB-luciferase construct measuring NFκB activity via luciferase assay. NFκB activity was assessed as well as pro-inflammatory genes (E-selectin and ICAM) and anti-inflammatory genes (KLF2 and eNOS).

(b) Results

Cells were chronically exposed to elevated levels of glucose prior to plating for hemodynamic experiments. For the experiment shown in FIG. 12, endothelial cells were preconditioned using atheroprone hemodynamic forces in the presence of elevated glucose for the remainder of the experiment. At the conclusion of the experiment gene expression and NFκB activity were assessed as a function of the glucose treatment in combination with TNFα.

While elevated glucose had no effect on basal levels of genes (untreated), samples treated with atheroprone shear stress and TNF-α had higher levels of inflammatory signaling when pretreated with elevated glucose, compared to mannose controls. FIGS. 12A and 12B show that elevated glucose increased activation of inflammatory signaling, including NFκB (FIG. 12A) activity and downstream gene activation of adhesion molecules E-Selectin and ICAM (FIG. 12B). Elevated glucose also caused larger decreases in atheroprotective signaling (eNOS, KLF2) compared to mannose treated controls (FIG. 12C). The results in FIG. 12 are presented as mean±SE, n=4, *p<0.05, t-test.

Example 3: An In Vitro Model for Hypertension (i) Angiotensin II (ANG2)

Angiotensin II (ANG2) levels are increased in patients with cardiovascular complications, such as atherosclerosis, diabetes or hypertension. Typical concentrations of ANG2 range from about 1 nM to about 5 nM in healthy patients, and from greater than about 6 nM to about 20 nM in hypertensive patients.

To assess the effects of ANG2 in the hemodynamic environment, endothelial cells and smooth muscle cells were plated as described above and subjected to 24 hours of shear stress preconditioning with healthy and atheroprone hemodynamic forces. ANG2 at a concentration of 10 nM (10.46 ng/ml) or a DMSO vehicle control (VEH) was added to the upper volume and RNA was collected for gene array analysis.

Figure 13B:
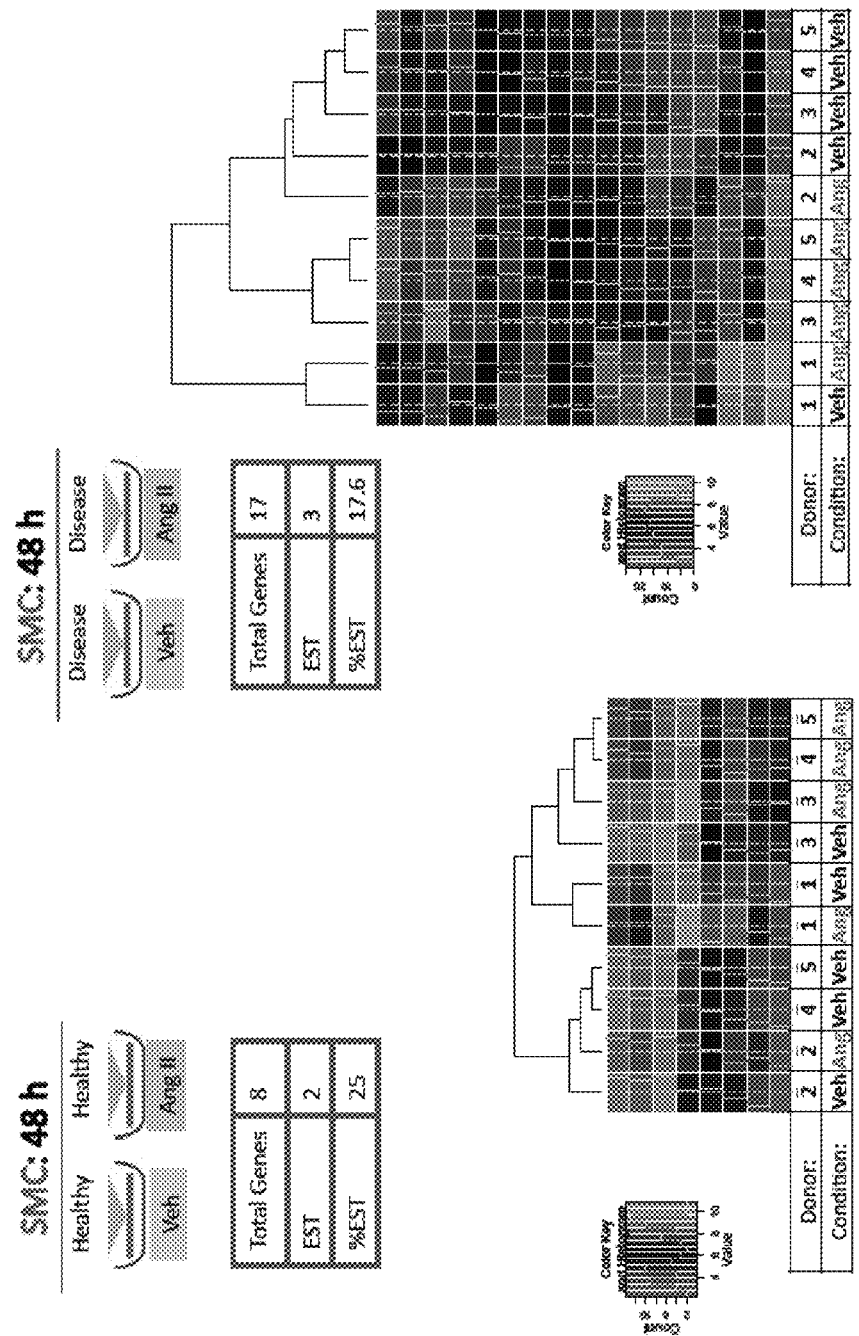

Gene array analysis of this condition compared to DMSO vehicle controls revealed many significant inflammatory genes that are upregulated by ANG2. FIG. 13 shows gene expression heat maps for both endothelial cells (FIG. 13A) and smooth muscle cells (FIG. 13B) treated with ANG2 under both healthy and atheroprone (disease) conditions. As seen in FIG. 13, numerous genes were significantly regulated by ANG2 and the ANG2 conditions sorted together in an unbiased way.

(ii) Aldosterone

Aldosterone is an important signaling hormone downstream of ANG2 in the renin-angiotensin system. Its levels can vary under a number of pathologies, including atherosclerosis, diabetes, and hypertension. Concentrations of aldosterone in healthy individuals are about 0.3 mM. Concentrations of aldosterone in individuals with hperaldosteronism range from about 0.8 mM to about 1 mM.

To assess the effects of aldosterone in the hemodynamic environment, endothelial cells and smooth muscle cells were plated as described above and subjected to 24 hours of shear stress preconditioning with healthy and atheroprone hemodynamic forces. Aldosterone at a concentration of 1 mM or a vehicle control (VEH) was added to the upper volume and RNA was collected for gene array analysis.

Figure 14A:
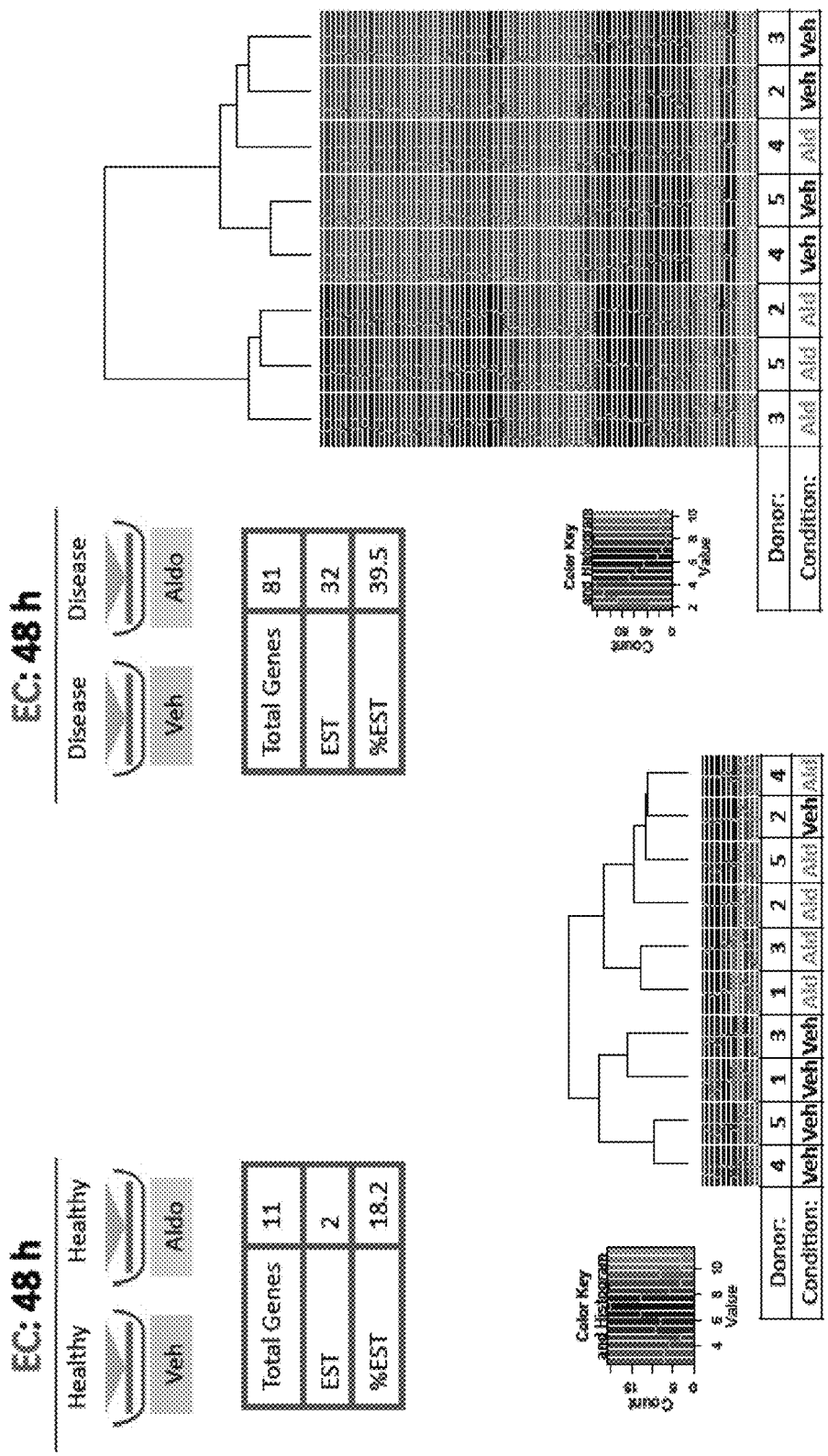
FIGS. 14A-B show exemplary gene array data for endothelial cells and smooth muscle cells treated with aldosterone under hemodynamic conditions.
Figure 14B:
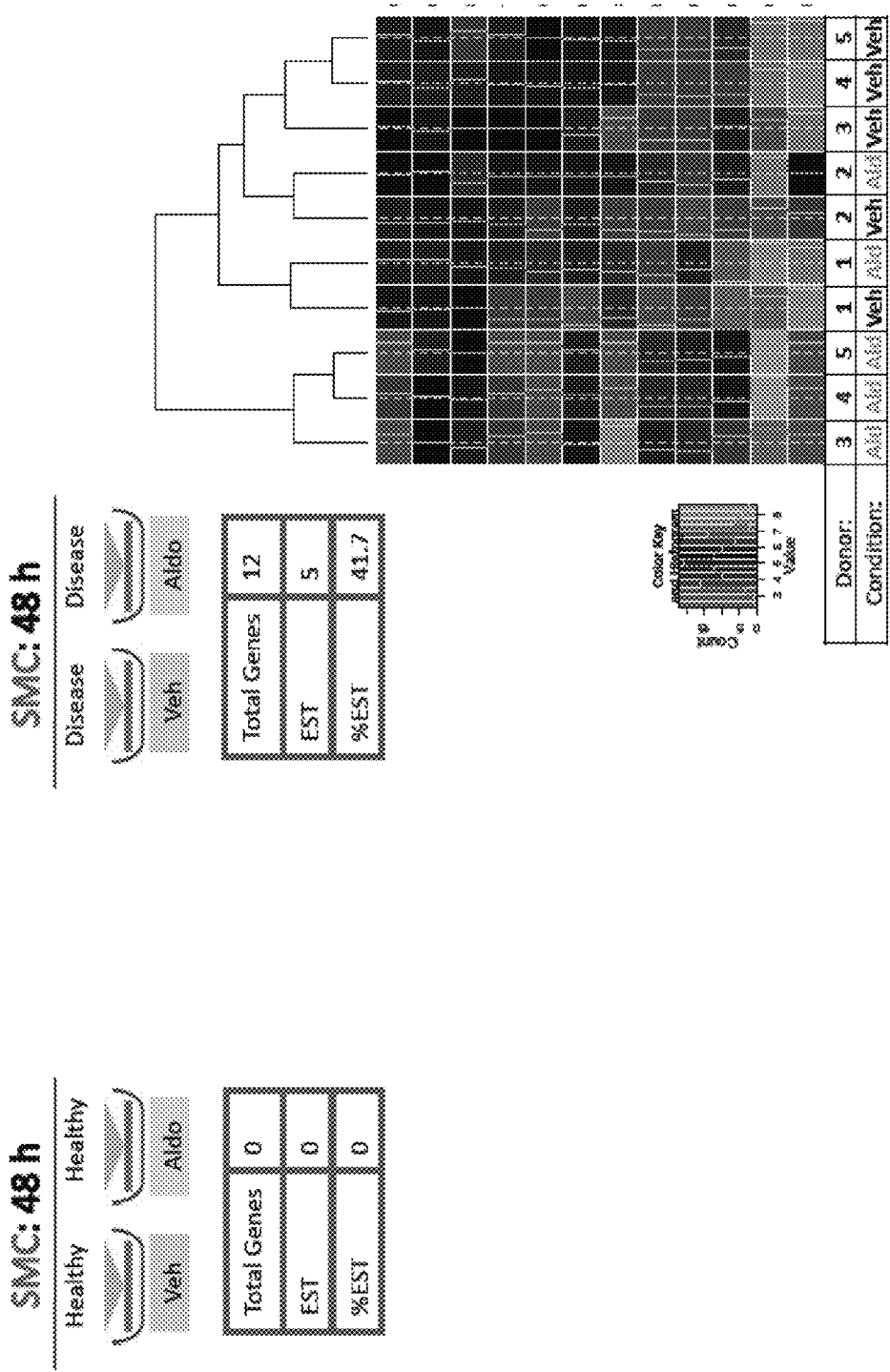

Gene array analyses of this condition compared to DMSO vehicle controls reveal many significant inflammatory genes that are upregulated by aldosterone. FIG. 14 shows the gene expression heat maps for endothelial cells and smooth muscle cells treated with aldosterone (Aldo) in both healthy and atheroprone (disease) conditions. Many significant genes were regulated by these conditions, with the majority of regulated genes found within the atheroprone hemodynamic environment.

Example 4: A Physiologic In Vitro Liver Model

Static hepatocyte cell culturing methods are associated with poor in vitro to in vivo correlations, due in part to the absence of physiological parameters which maintain metabolic phenotype over time in vivo. The inventors have now discovered that restoring physiological hemodynamics and transport retains hepatocyte phenotype and function in vitro compared to the standard static hepatocyte collagen gel configuration.

To recreate a cellular hepatocyte system with fluid dynamics and transport analogous to in vivo liver circulation, a cone-and-plate device-based technology was employed that has been extensively used to re-establish in vivo blood vessel cell phenotypes by recreating the exposure of vascular endothelial cells to human-derived hemodynamic blood flow forces in vitro. This technology is described in U.S. Pat. No. 7,811,782, the contents of which are hereby incorporated by reference. The technology (FIG. 15B) was adapted and modified to design a rat liver monoculture system which applies hemodynamic flow and transport conditions reflective of in vivo hepatic circulatory values. The configuration of cells in the device (FIG. 15C) is based on in vivo microarchitecture of hepatic lobules (see FIG. 15A) where cords of hepatocytes are separated from sinusoidal blood flow by a filtering layer of endothelial cells. This design uses a porous polycarbonate membrane suspended in a cell culture container, with primary rat hepatocytes sandwiched in a collagen gel on one side of the porous membrane. The porous membrane acts analogously to the filtering layer of sinusoidal endothelial cells which is present in the liver. Media is continuously perfused on both sides of the porous membrane, while hemodynamic forces, derived from a range of physiological blood flow values, are continuously applied to the non-cellular side of the porous membrane. The entire set up is housed in a controlled environment with 5% $CO_2$ and at 37° C. A flow-based culture system was effectively created whereby hepatocytes are shielded from direct effects of flow, as they would be in vivo. Recapitulating the hemodynamics and in a system designed to be analogous to the microstructure of the hepatic sinusoid results in stable retention of a differentiated hepatic and metabolic phenotype similar to that of in vivo liver.

Methods (i) Animal Surgery and Hepatocyte Isolation

All animals used for the experiments were treated according to protocols approved by HemoShear's Animal Care & Use Committee. Hepatocytes were isolated from male Fischer rats (250 g-350 g) by a modification of Seglen's two-step collagenase perfusion procedure using a 20 mL/min flow rate (Seglen, *Hepatocyte Suspensions and Cultures as Tools in Experimental Carcinogegnesis, J. Toxicology & Environmental Health,* 5(2-3): 551-560 (1979), the contents of which are hereby incorporated by reference). Briefly, the rats were anaesthetized with isoflurane, following which the abdominal cavity was incised and the inferior vena cava was canulated while making an excision was made in the portal vein for outflow. The liver was perfused in two steps, first with a $Ca^{++}$-free buffer to flush out blood and break up intercellular junctions, followed by collagenase in a $Ca^{++}$-containing buffer to digest the extracellular collagen matrix. After the liver was suitably perfused it was excised and freed of the capsule in a Petri dish under a sterile hood. An enriched hepatocyte population (~95% purity) was obtained by two sequential 65 g centrifugation and washing cycles of 10 minutes each followed by a 10 minute spin with 90% PERCOLL (colloidal silica particles of 15-30 nm diameter (23% w/w in water) coated with polyvinylpyrrolidone (PVP); used to establish density gradients that can be used to isolate cells). The viability of hepatocytes was determined by trypan blue exclusion test and cells with a viability over 85% are used.

(ii) Cell Culture and Device Operating Conditions

Hepatocyte Culture Media:

For the data shown in FIGS. 16-20, the rat hepatocyte culture media contained base media of DMEM/F12 containing high glucose (17.5 mM), supplemented by fetal bovine serum (10% at the time of plating and reduced to 2% for maintenance after 24 hours). The media also contained gentamycin (50 µg/ml), ITS (insulin concentration 2 µMol), 1% NEAA, 1% GLUTAMAX, and dexamethasone (1 µM at plating and 250 nM for maintenance after 24 hours).

Collagen Coating and Plating:

Collagen solution was made by mixing Type I Rat Tail Collagen in sterile distilled water, 10× phosphate buffered saline (PBS) and 0.2N sodium hydroxide in a predefined ratio (To make up 1 ml, the components were 440 µl, 375 µl, 100 µl and 85 µl respectively).

For cultures to be subjected to static conditions, 100 mm tissue culture-treated sterile cell culture dishes were coated with 7 µl/$cm^2$ of collagen solution. For cultures to be subjected to controlled hemodynamics, the lower surface of the porous membrane of 75 mm TRANSWELLS (polycarbonate, 10 µm thickness and 0.4 µm pore diameter, no. 3419, Corning) were coated with 7 µl/$cm^2$ of collagen solution. After allowing an hour for the solution to gel, the surfaces were washed with DPBS, hepatocytes were plated at a seeding density of 125,000 viable cells/$cm^2$, and a second layer of collagen gel added after 4 hours. After 1 hour, the TRANSWELLS were inverted and placed into cell culture dishes, and media was added (9 ml in the lower volume and 6 ml in the upper volume). 7 ml of media was added to the tissue culture dishes to be used for static cultures. After 24 hours, the media was switched to maintenance media (containing 2% FBS), and the cell culture dishes containing TRANSWELLS were placed into the cone-and-plate device. Controlled hemodynamics were applied to the surface of the porous membrane of the TRANSWELL in the upper volume.

Operating conditions: The shear stress in dynes/$cm^2$ ($\tau$) was calculated for a typical hepatic sinusoid based on the formula for pressure driven flow of a Newtonian fluid through a cylinder, $$\tau = \frac{\Delta P \cdot r}{2l}$$

using reference values for pressure gradient across the sinusoid ($\Delta P$), radius of sinusoids (r) and length of the sinusoids (l) from the literature. As part of an initial optimization process, a range of applied shear stress conditions obtained by altering media viscosity and cone speed that resulted in rates within an order of magnitude of the value predicted from literature were seen to be correlated with different transport profiles of horse radish peroxidase dye across the membrane. These were tested for gene expression profiles of the hepatocytes 7 days into culture (data not shown). No differences were observed between static cultures and those that were simply perfused without any applied shear and based on the gene expression profiles, an operational shear rate of 0.6 dynes/$cm^2$ was selected for all the experiments described in this Example.

(iii) Assessment of Phenotypic, Functional, and Metabolic Parameters

RT-PCR:

Changes in metabolic and insulin/glucose/lipid pathway genes were assessed by extracting RNA from hepatocytes from devices run under healthy and steatotic conditions at the end of the culture period (7 or 14 days) and performing RT-PCR on this RNA. The TRANSWELLS were are removed from the devices and washed with PBS prior to scraping the cells off the porous membrane. Total RNA was isolated using a PURELINK RNA Mini Kit (a kit for purification of total RNA from cells) and reverse transcribed to cDNA using the ISCRIPT cDNA Synthesis Kit (a cDNA synthesis kit). Primers were designed for the metabolic genes CYP1A1, CYP1A2, CYP3A2, MDR, and GST as well as the insulin/glucose/lipid pathway genes GPAT, ACC1, IRS-2, PPAR-γ, SREBP, ChREBP, LXR, SCD1, CPT1. Primer sequences are shown below in Table 1:

TABLE 1

Rat Primer Sequences

| Gene | Forward (SEQ ID NO.) | Reverse (SEQ ID NO.) |
|---|---|---|
| CYP1A1 | GCTGCTCTTGGCCGTCACCA (1) | TGAAGGGCAAGCCCCAGGGT (2) |
| CYP1A2 | CCTGCGCTACCTGCCCAACC (3) | GGGCGCCTGTGATGTCCTGG (4) |
| CYP3A2 | CGGCGGGATTTTGGCCCAGT (5) | CAGGCTTGCCTGTCTCCGCC (6) |
| MDR | GCTGCTGGGAACTCTGGCGG (7) | CCGGCACCAATGCCCGTGTA (8) |
| GST (Pi subunit) | CGCAGCAGCTATGCCACCGT (9) | CTTCCAGCTCTGGCCCTGGTC (10) |
| GPAT | AGCGTTGCTCCATGGGCATATAGT (11) | TGTCAGGGATGGTGTTGGATGACA (12) |
| ACC1 | TGTCATGGTTACACCCGAAGACCT (13) | TTGTTGTTGTTTGCTCCTCCAGGC (14) |
| IRS-2 | GCGAGCTCTATGGGTATATG (15) | AGTCCTCTTCCTCAGTCCTC (16) |
| PPAR-g | ATATCTCCCTTTTTGTGGCTGCTA (17) | TCCGACTCCGTCTTCTYGATGA (18) |
| SREBP | GGAGCCATGGATTGCACATT (19) | AGGCCAGGGAAGTCACTGTCT (20) |
| ChREBP | CTATGTCCGGACCCGCACGC (21) | CTATGTCCGGACCCGCACGC (22) |
| LXR | ACTCTGCAACGGAGTTGTGGAAGA (23) | TCGGATGACTCCAACCCTATCCTT (24) |
| SCD1 | TGTGGAGCCACAGGACTTACAA (25) | AGCCAACCCACGTGAGAGAAGAAA (26) |
| CPT1 | ATGTGGACCTGCATTCCTTCCCAT (27) | TTGCCCATGTCCTTGTAATGTGCG (28) |
| CYP2B1 | GAGGAGTGTGGAAGAACGGATTC (29) | AGGAACTGGCGGTCTGTGTAG (30) |
| CYP2B2 | TCATCGACACTTACCTTCTGC (31) | AGTGTATGGCATTTGGTACGA (32) |

RNA expression was analyzed by real-time RT-PCR using IQ SYBR Green Supermix (a PCR reagent mixture for RT-PCR) and a CFX96 Real-Time System with C1000 Thermal Cycler (an RT-PCR detection system and thermal cycler). RNA data were normalized to endogenous expression of β2-microglobulin and reported as a relative quantity compared to healthy cultures.

Urea and Albumin Assays:

Media collected from static cultures and devices at various time points was assayed for albumin using a rat-specific ELISA based kit (Bethyl Laboratories) as per the manufacturer's protocols. Urea was estimated from the media samples using a standard colorimetric assay (QUANTICHROM Urea Assay Kit, DIUR-500, Gentaur). All measurements between the systems were normalized to a per million cells/day rate for comparison based on the volume of media perfused and the number of initially plated cells.

Western Blots: Following application of controlled hemodynamics, ⅓ of the plated surface of the porous membrane of the TRANSWELL (~1.8 million cells) was harvested for protein in 150 μl 1×RIPA buffer containing fresh 150 mM DTT and protease inhibitors (HALT Protease Inhibitor Cocktail (Pierce)+1 mM PMSF+200 mM DTI). Samples were sonicated on ice with 5×1 second pulses, allowed to sit on ice for 30 minutes and centrifuged at 17,000×g for 10 minutes in a chilled microcentrifuge. Protein determination was done using A660 nm Protein Reagent (Pierce). Samples were boiled 70° C. for 10 minutes and then run on a 7.5% TGX gel (a pre-cast polyacrylamide gel, BioRad) before wet-transferring to 0.2 μm PVDF membrane and blocking in 5% non-fat milk at room temperature for 10 minutes. Membranes were incubated overnight at 4° C. in rabbit anti UGT antibody (Cell Signaling, 1:500 dilution). Secondary antibody (Santa Cruz, Goat anti Rabbit HRP, 1:5000 dilution) incubation was at room temperature for one hour. Chemiluminescent signal was developed using SUPERSIGNAL WEST PICO (a chemiluminescent substrate for horseradish peroxidase, Pierce) reagent and captured using an Innotech ALPHAEASE imaging system. For normalization, gels were probed for mouse anti β-Actin (Sigma A1978, 1:2000 dilution) followed by secondary goat anti mouse HRP (Santa Cruz sc-2005, 1:10,000 dilution).

Immunostaining and Biliary Activity Stain:

Antibodies used: Hnf4a (Santa Cruz sc-8987), E-cadherin (Santa Cruz sc-71009), and anti-MRP2 (Abcam ab3373). At the chosen time points in the experimental design, the static cultures and cultures subjected to controlled hemodynamics were washed gently with 1×PBS, following which they were fixed with 4% paraformaldehyde for 30 minutes. The samples were stored in PBS at 4° C. until they were to be immunostained. For immunostaining, the samples were first permeabilized with 0.1% TRITON X (a nonionic surfactant) for 20 minutes and then washed with PBS and blocked with 5% goat serum. The incubation with primary antibodies was at a dilution of 1:100 for 1 hour. After 3 washes with PBS with 1% BSA, the secondary antibody was added at a dilution of 1:500 for another hour. The samples were then washed with PBS plus 1% BSA and then mounted for confocal imaging.

For imaging of the biliary activity at canalicular junctions, sections of the porous membrane of the TRANSWELL were washed with PBS and incubated with media containing 10 μM carboxy-2,7-dichlorofluorescein diacetate (CDFDA) for 10 minutes. Samples were then washed with PBS and placed on glass slide for confocal imaging.

Transmission Electron Microscopy:

Transmission electron microscopy was performed as described below in Example 5.

Cytochrome Activity Assays:

Hepatocytes were cultured in the cone-and-plate devices under static or controlled hemodynamic conditions for five days, and then treated with 0.1% dimethyl sulfoxide (DMSO) or known inducers of cytochrome enzymes (3-methylcholanthrene and dexamethasone) for 48 hours. Porous membrane segments roughly 2 cm$^2$ in area were excised and transferred to standard 24-well plates alongside corresponding static cultures. The cells were incubated with 500 μl of hepatocyte media containing substrates from commercially available P450-GLO kits (kits for luminescent cytochrome p450 assays) at the manufacturer-recommended concentrations. After 4 hours, the media was transferred to 96-well plates and assayed for luminescent metabolites to reflect cytochrome p450 activity as per the manufacturer protocol. The ATP content of the cells in the same porous membrane segments or static wells was then estimated by the CELLTITER-GLO assay (a kit for a luminescent cell viability assay) using the manufacturer's protocol, and the cytochrome values were normalized to ATP content.

Results (i) Controlled Hemodynamics Maintain Hepatocyte Phenotype, Polarized Morphology and Transporter Localization Relative to Traditional Static Monoculture Conditions.

Freshly isolated rat primary hepatocytes were obtained and plated in collagen gel sandwiches on porous membranes. After 1 day, cultures were either continued under standard static conditions in a CO$_2$ incubator at 37° C. or introduced into the hemodynamic flow technology and maintained under controlled hemodynamics at pre-determined indirect shear rates of 0.6 dynes/cm$^2$. Media was changed every 48 hours in static cultures and the devices were continuously perfused. After 7 days, the cultures were removed and fixed with 4% paraformaldehyde before immunostaining with antibodies for the hepatocyte differentiation markers E-cadherin and HNF-4α, and visualized by confocal microscopy. E-cadherin staining patterns in static collagen gel sandwich cultures (FIG. 16A) displayed higher levels of cytoplasmic E-cadherin confirmed and quantified by morphometric analysis (adjacent graphs) and disrupted peripheral membrane distribution. Under controlled hemodynamics (FIG. 16B), hepatocytes exhibited a more differentiated morphology characterized by distinct peripheral membrane localization and lower cytoplasmic levels of E-cadherin. The staining pattern of the HNF4α showed a distinct difference in localization patterns with the cells in static cultures having a more diffuse staining pattern by 7 days (FIG. 16C) while the cells under controlled hemodynamics retained staining confined to the nucleus (FIG. 16D), similar to what is seen in vivo. Polarized morphology and canalicular localization of the transporter multi drug resistant protein-2 (MRP-2) that appears after 5-7 days of culture in collagen gel sandwiches is lost in static cultures by day 14 (FIG. 16E) but the canalicular network patterns are stable and extensive under controlled hemodynamics (FIG. 16F). Day 14 cultures maintained under controlled hemodynamics co-stained for MRP-2 and HNF-4a (FIG. 17A) alongside sections from rat in vivo liver (FIG. 17B) show very similar staining patterns. Transmission electron microscopy images of day 7 cultures under controlled hemodynamics (FIG. 17C) demonstrate the retention of subcellular components such as rough and smooth endoplasmic reticulum and mitochondria in addition to confirming the presence of bile canaliculi and tight junctions.

(ii) Controlled Hemodynamics Results in Retention of Hepatocyte-Specific Function in Rat Hepatocytes in a Collagen Gel Configuration Relative to Static Cultures Over 14 Days.

Hepatocytes were cultured under static or controlled hemodynamics (0.6 dynes/cm$^2$) for 2 weeks and media sampled at 4, 7, 11, and 14 days. Assays for urea and albumin were performed on the media and the values were normalized to production rates over 24 hours per million cells based on the initial number of plated cells. Hepatocyte function reflected by secreted albumin estimated from media samples at various time points over 14 days and expressed as μg/10$^6$ plated hepatocytes/day (FIG. 18A), showed significantly higher levels (3-4 fold) under controlled hemodynamics (solid line) as compared to static cultures (dashed line) (Day 7: 97.96±11.34 vs. 25.84±8.22, p=0.00001; Day 14: 87.80±8.62 vs. 33.93±4.39, p=0.0001). Urea secretion (FIG. 18B) by hepatocytes expressed as μg/10$^6$ plated hepatocytes/day under controlled hemodynamics (solid line) was also found to be at 4-5 fold higher levels than static cultures (dashed line) consistently over two weeks in culture (Day 7: 622.78±33.96 vs. 139.76±13.37, p=2.7×10$^{-9}$; Day 14: 667.71±84.37 vs. 178.68±6.13, p=1×10$^{-6}$).

(iii) Controlled Hemodynamics Differentially Regulates the Expression of Phase I and Phase II Metabolic Genes and Proteins Compared to Static Cultures.

Hepatocytes were cultured under static or controlled hemodynamics (0.6 dynes/cm$^2$) for 7 days. QRT-PCR was performed for select metabolic genes (Table 1) on RNA samples at day 7 from these conditions. All values were normalized to day 7 static cultures. Hepatocytes cultured under controlled hemodynamics resulted in gene expression levels that were consistently higher than in static cultures (n=11, Fold changes relative to static cultures: Cyp1A1~54, p=0.0003; Cyp1A2~64, p=0.005, Cyp2B1~15, p=0.001: FIG. 19A, Cyp2B2~2.7, p=0.09 and Cyp3A2~4, p=0.075: FIG. 19B) and closer to in vivo levels. Interestingly, the expression levels of the gene for the Pi subunit of phase II enzyme GST, known to increase in static cultures over time, was lower in both in vivo liver (−4.9 fold, p=0.152) and hepatocytes cultured under controlled hemodynamics (−2.3 fold, p=0.025) compared to static cultures (FIG. 19C).

Hepatocytes were cultured under static or controlled hemodynamics (0.6 dynes/cm$^2$). Cell cultures were taken down at 4, 7, 11 and 14 days and cell lysates were obtained as described in the methods section, normalized to total protein, and equivalent samples were loaded and run on SDS page gels before probing with antibodies for the phase II enzyme UGT1 A1 and β-actin (for normalization). Western blots (FIG. 19D) demonstrate that UGT1 A1 is upregulated under controlled hemodynamics as compared to static conditions at all the time points over 2 weeks in culture. In the same experiment, part of the porous membrane of the TRANSWELL from 14 day cultures under controlled hemodynamics was fixed with 4% paraformaldehyde and stained for HNF-4a and the canalicular transporter protein MRP-2, demonstrating retention and localization of MRP-2 along the canalicular junctions between the hepatocytes (FIG. 17A). The remainder of the membrane was excised after removal from the device and immediately incubated with the substrate carboxy-2,7-dichlorofluorescein diacetate (CDFDA). The cells were imaged by confocal microscopy over a time window of 20 minutes to observe the breakdown of the substrate into carboxy-2,7-dichlorofluorescein (CDF) and its active secretion into the bile canalicular structures (seen in FIG. 17C). The pattern was very similar to that of sectioned samples of in vivo liver immunostained with antibodies to MRP-2 and HNF-4a (FIG. 17B).

(iv) Rat Hepatocytes Cultured Under Controlled Hemodynamics Display a Higher Level of Basal and Inducible Cytochrome p450 Activity than Static Cultures at More In Vivo-Like Concentrations.

To validate that the increase in metabolic genes and proteins translated to changes in metabolic activity, primary rat hepatocytes were cultured as described earlier in the cone-and-plate devices under controlled hemodynamics (0.6 dynes/cm$^2$) and in static collagen gel cultures. After 5 days, they were either left untreated or treated with 0.1% DMSO, 1A/1B inducer 3-Methyl Cholanthrene (3-MC, 1 µM in static and 0.1 µM under controlled hemodynamics) or 3A inducer dexamethasone (50 µM in static and 02.5 µM under controlled hemodynamics). After 48 hours, on day 7, segments of the porous membrane from the devices containing hepatocytes cultured under controlled hemodynamics that were roughly 2.0 cm$^2$ in area were excised and transferred to standard 24-well plates and treated with substrates for the Cyp p450 enzymes in parallel to corresponding static cultures treated with the different agents. Cytochrome p450 assays were done on day 7 using commercially available P450-GLO kits. After 4 hours the media was transferred to 96-well plates and assayed for luminescent metabolites to reflect cytochrome p450 activity. Values were normalized to the ATP content of the cells assessed by CELLTITER-GLO assay in order to get an accurate representation of live cells and avoid any confounding effects of the collagen gels on total protein measurements.

Basal activity level of the cytochrome p450 enzymes (FIG. 20A) in untreated cultures was upregulated by controlled hemodynamics compared to static (1A~15 fold, 1B~9 fold and 3A~5 fold). In spite of higher levels of basal activity, under controlled hemodynamics the response to classical inducers (FIG. 20B) was well maintained (1A/1B response to DMSO vs. 3-MC—4.87 vs. 133.06; 3A response to DMSO vs. Dexamethasone—11.64 vs. 57.53).

While initially measuring the Cyp activity to confirm the enhanced gene expression that was noted under controlled flow, 50 µM dexamethasone, the concentration recommended for inducing static cultures, was toxic in this system. As a result the concentration of the dexamethasone was decreased to 1 µg/ml in order to get an inductive response, a level that correlates well with plasma concentrations seen in vivo in rats. Similarly, induction responses for 3-MC were also seen at 10-fold lower levels under controlled hemodynamics.

To confirm the presence of transporter activity under controlled hemodynamics, TRANSWELL filter segments from the devices were incubated with the substrate carboxy-2,7-dichlorofluorescein diacetate (CDFDA). The compound was broken down to the fluorescent form CDF Carboxy-2,7-Dichlorofluorescein which was actively secreted out into the canalicular spaces demonstrating active canalicular transport (FIG. 20C).

The data described above are the result of experiments carried out to evaluate the effect of exposing hepatocytes to controlled hemodynamics in order to restore their phenotype more similar to that observed in vivo. These experiments used standard media formulations routinely used in static culture in order to allow for side by side comparison with the static collagen gel cultures and identify the selective benefits of controlled hemodynamics. In the course of these experiments, hepatocytes cultured under these controlled hemodynamic conditions demonstrated enhanced in vivo-like phenotype and function and were more responsive to inducers such as dexamethasone and 3-MC. However, some accumulation of lipids was also observed in hepatocytes cultured with the concentrations of glucose (17.5 mM) and insulin (2 µMop which are used routinely for assays in static systems. It has now been discovered that when hepatocytes are cultured under controlled hemodynamic conditions as described herein, much lower concentrations of glucose and insulin, similar to the concentrations observed in healthy individuals in vivo, can be used. The data indicate that these lower concentrations of glucose (5.5 mM) and insulin (2 nM) further enhance hepatocyte function and metabolic activity. Moreover, hepatocytes can be cultured under controlled hemodynamics in media containing the higher concentrations of glucose and insulin in order to create a model of fatty liver disease, as explained further in the following Example.

Example 5: An In Vitro Model for Fatty Liver Disease

Nonalcoholic fatty liver disease (NAFLD) is the most common cause of liver dysfunction and is associated with obesity, insulin resistance, and type 2 diabetes. The changes in the fatty liver progress from early accumulation of fat vesicles within hepatocytes (hepatic steatosis) to subsequent loss of liver metabolic function and inflammatory changes, ultimately leading to fibrosis and cirrhosis. Animal in vivo models of fatty liver disease have successfully used either high fat diets or low fat, high carbohydrate diets that induce the hyperglycemia and hyperinsulinemia reflective of the diabetic milieu to induce triglyceride buildup. However in vitro models typically use only overloading with free fatty acids (oleic, palmitic or linoleic acid) to induce fatty changes and may not capture the de novo hepatocyte response to the high levels of glucose and insulin that may play a critical role in the pathogenesis of the disease. Static hepatocyte cultures are also known to have a markedly decreased insulin response and standard culture medias typically require high non-physiological levels of the hormone for basic hepatocyte survival and function. The model described herein, by contrast, preserves a more physiological hepatocyte response to drugs and hormones and allows us to maintain basic liver function at closer to in vivo concentration levels of glucose and insulin (as described above in Example 4), and furthermore allows us to elicit the pathologic response seen in fatty liver by creating a diabetic-like milieu characterized by high glucose and insulin levels.

Methods:

(i) Animal Surgery and Hepatocyte Isolation

Animal surgery and hepatocyte isolation were performed as described above in Example 4.

(ii) Cell Culture and Device Operating Conditions

Healthy Hepatocyte Culture Media:

The healthy hepatocyte culture media contained base media of DMEM/F12 containing low glucose (5.5 mM), supplemented by fetal bovine serum (10% at the time of plating and reduced to 2% for maintenance after 24 hours). Additionally, the media contained gentamycin (50 µg/ml), ITS (insulin, transferrin, and selenium; insulin concentration of 2 nM), 1% non-essential amino acids (NEAA), 1% GLUTAMAX (a media supplement containing L-alanyl-L-glutamine), and dexamethasone (1 µM at plating and 250 nM for maintenance after 24 hours for the data shown in FIGS. 21 and 22; 100 nM throughout the experiment for the data shown in FIGS. 25-32).

Media to Induce Fatty Liver Changes ("Fatty Liver Media"):

The culture media used to induce fatty liver changes contained base media of DMEM/F12 containing high glucose (17.5 mM), supplemented by fetal bovine serum (10% at the time of plating and reduced to 2% for maintenance after 24 hours). The media also contained gentamycin (50 µg/ml), ITS (insulin concentration 2 µMol), 1% NEAA, 1% GLUTAMAX, and dexamethasone (1 µM at plating and 250 nM for maintenance after 24 hours for the data shown in FIGS. 21 and 22; 100 nM throughout the experiment for the data shown in FIGS. 25-32).

Collagen Coating and Plating:

Collagen solution was made as described above in Example 4. The lower surfaces of the porous membranes of 75 mm TRANSWELLS (polycarbonate, 10 µm thickness and 0.4 µm pore diameter, no. 3419, Corning) were coated with 300 µl of the collagen solution. After allowing an hour for the solution to gel, the surfaces were washed with DPBS, hepatocytes were plated at a seeding density of 125,000 viable cells/cm$^2$, and a second layer of collagen gel added after 4 hours. After 1 hour, the TRANSWELLS were inverted and placed into cell culture dishes, and media was added (9 ml in the lower volume and 6 ml in the upper volume). After 24 hours (i.e., on day 2 of the experiments), the media was changed to maintenance media (the healthy or fatty liver media described above) and the Petri dishes were placed in the cone-and-plate hemodynamic flow device, and controlled hemodynamics were applied to the surface of the porous membrane of the TRANSWELL in the upper volume. In some experiments, the maintenance media contained 1.5 µM pioglitazone in 0.1% DMSO vehicle or the 0.1% DMSO vehicle alone. The cells were cultured under controlled hemodynamics until day 7, when hepatocytes were examined using the assays described below.

Operating Conditions:

The shear stress was calculated as described above in Example 4. A range of applied shear stress conditions, generated by altering media viscosity and cone speed, and resulting in rates within an order of magnitude of the value predicted from literature (0.1 to 6 dynes/cm$^2$) were used. These were correlated with different transport profiles of reference dye horse radish peroxidase dye across the membrane. Cultures were run for 7 days and assessed for fatty liver changes.

(iii) Measurement of Fatty Liver Changes:

To examine changes occurring in the fatty liver model against healthy controls the following were evaluated:
(a) Changes in metabolic and insulin/glucose/lipid pathway genes (RT-PCR);
(b) Accumulation of intracellular lipids within hepatocytes by Oil Red O assay, Nile red staining, and measurement of total triglycerides;
(c) Changes in differentiated function of hepatocytes (urea and albumin secretion);
(d) Changes in metabolic activity (Cytochrome p450 assays); and
(e) Morphological changes within hepatocytes by transmission electron microscopy (TEM).

RT-PCR and urea and albumin assays were performed as described above in Example 4.

Staining Methods:

Hepatocyte TRANSWELL membrane sections were permeabilized in 0.1% Triton-X diluted in PBS for 20 minutes and washed thrice in PBS for five minutes each. Samples were then blocked in 5% goat serum, 0.2% blotting grade non-fat dry milk blocker, and 1% BSA in PBS for 45 minutes. The samples were then washed thrice in 0.1% BSA in PBS and incubated with 1:5000 dilution of Nile red (1 mM stock), 1:1000 DRAQ5 (a fluorescent DNA dye; Cell Signalling), 1:500 ALEXA FLUOR 488 conjugated phalloidin (Life Technologies), and 1% BSA in PBS for thirty minutes and protected from light. The samples were washed in 0.1% BSA in PBS thrice for five minutes each and mounted on glass cover slips using PROLONG GOLD antifade mounting media (an antifade reagent; Invitrogen). The samples were imaged on a Nikon C1+Confocal System microscope.

Transmission Imaging Microscopy (TEM):

Segments of the porous membranes from TRANSWELLS containing hepatocytes cultured under healthy or steatotic conditions for 7 days were washed with PBS before fixing in a solution containing 4% paraformaldehyde and 2% glutaraldehyde for 1 hour. The samples were then sent to be processed for TEM at the University of Virginia imaging center. TEM images were evaluated for accumulation of lipid within the hepatocytes, the appearance of subcellular organelles such as mitochondria and smooth and rough endoplasmic reticulum, retention of polarized morphology, and bile canaliculi.

Oil Red O Assay:

Accumulation of intracellular lipids within hepatocytes was assessed by adapting and modifying a commercially available Steatosis Colorimetric Assay Kit (Cayman Chemical). At the end of the culture period, 2 cm$^2$ sized porous membrane segments containing the hepatocytes from devices under healthy and steatotic conditions were washed with PBS and fixed in 4% paraformaldehyde for 30 minutes. These porous membrane segments were then washed with PBS, dried completely and incubated with 300 µl of Oil Red O working solution for 20 minutes in 24 well plates. The porous membrane segments were then washed repeatedly with distilled water 7-8 times followed by two five minute washes with the wash solution provided in the Steatosis Colorometric Assay Kit. Dye extraction solution (300 µl) was added to each well and the plates were incubated on an orbital shaker for 15-30 minutes under constant agitation. The solution was then transferred to clear 96-well plates and absorbance was read at 490-520 nm in a spectrophotometer.

Measurement of Total Triglycerides:

Triglyceride content was assessed using a commercially available colorimetric assay kit (Cayman Triglyceride Colorimetric Assay Kit, Cat #10010303). At the end of the treatment period, cells were collected from the porous membranes by scraping with a rubber policeman and PBS, after which they were centrifuged (2,000×g for 10 minutes at 4° C.). The cell pellets were resuspended in 100 µl of cold diluted Standard Diluent from the triglyceride assay kit and sonicated 20 times at one second bursts. The cell suspension was then centrifuged at 10,000×g for 10 minutes at 4° C. The supernatant was removed and used for the assay as per the manufacturer's protocol and normalized to protein content from the same samples.

Cytochrome Activity Assays:

Hepatocytes were cultured in the cone-and-plate devices under healthy and steatotic conditions for 7 days. Porous membrane segments roughly 2 cm$^2$ in area were excised and transferred to standard 24-well plates alongside corresponding static cultures. The cells were incubated with 500 µl of healthy hepatocyte media containing substrates from commercially available P450-GLO kits at the manufacturer-recommended concentrations. After 4 hours, the media was transferred to 96-well plates and assayed for luminescent metabolites to reflect cytochrome p450 activity as per the manufacturer protocol. The ATP content of the cells in the same porous membrane segments or static wells was then estimated by the CELLTITER-GLO assay using the manufacturer's protocol, and the cytochrome values were normalized to ATP content.

Results:

Nile Red Staining:

FIGS. 25A and B show staining of hepatocytes cultured in the healthy (FIG. 25A) or fatty liver (FIG. 25B) media with Nile red, phalloidn, and DRAQ5. As can be seen in FIG. 25B, the hepatocytes cultured in the fatty liver media (containing high concentrations of glucose and insulin) accumulate a large number of lipid droplets.

Figure 26:
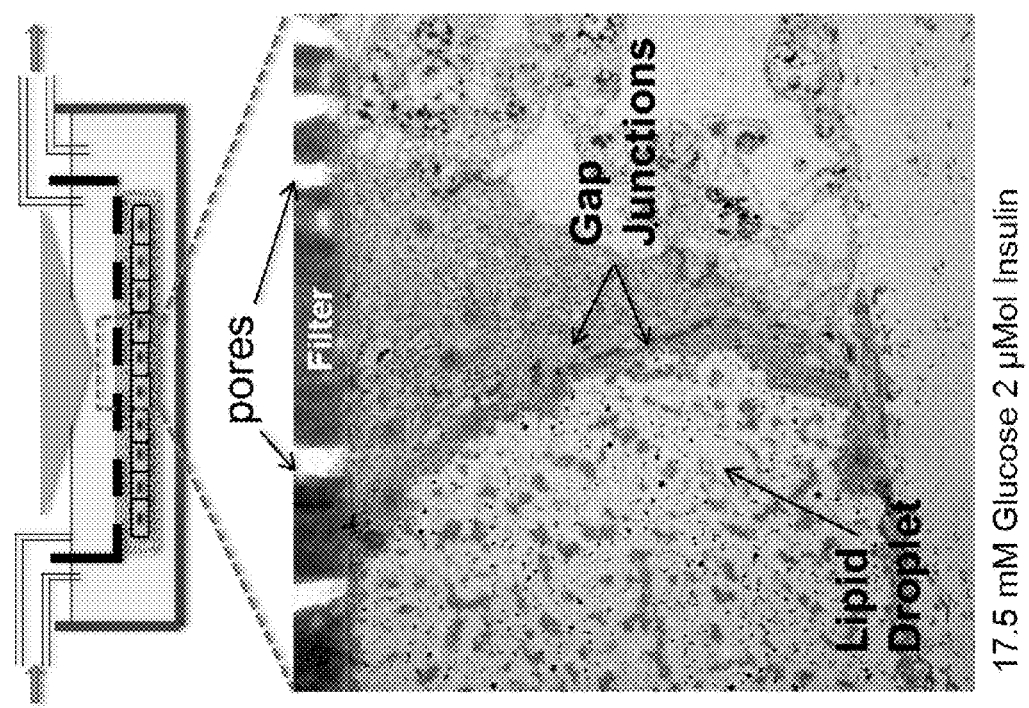
FIG. 26 shows an transmission electron microscopy image of rat hepatocytes cultured under high glucose/high insulin conditions.
Figure 28:
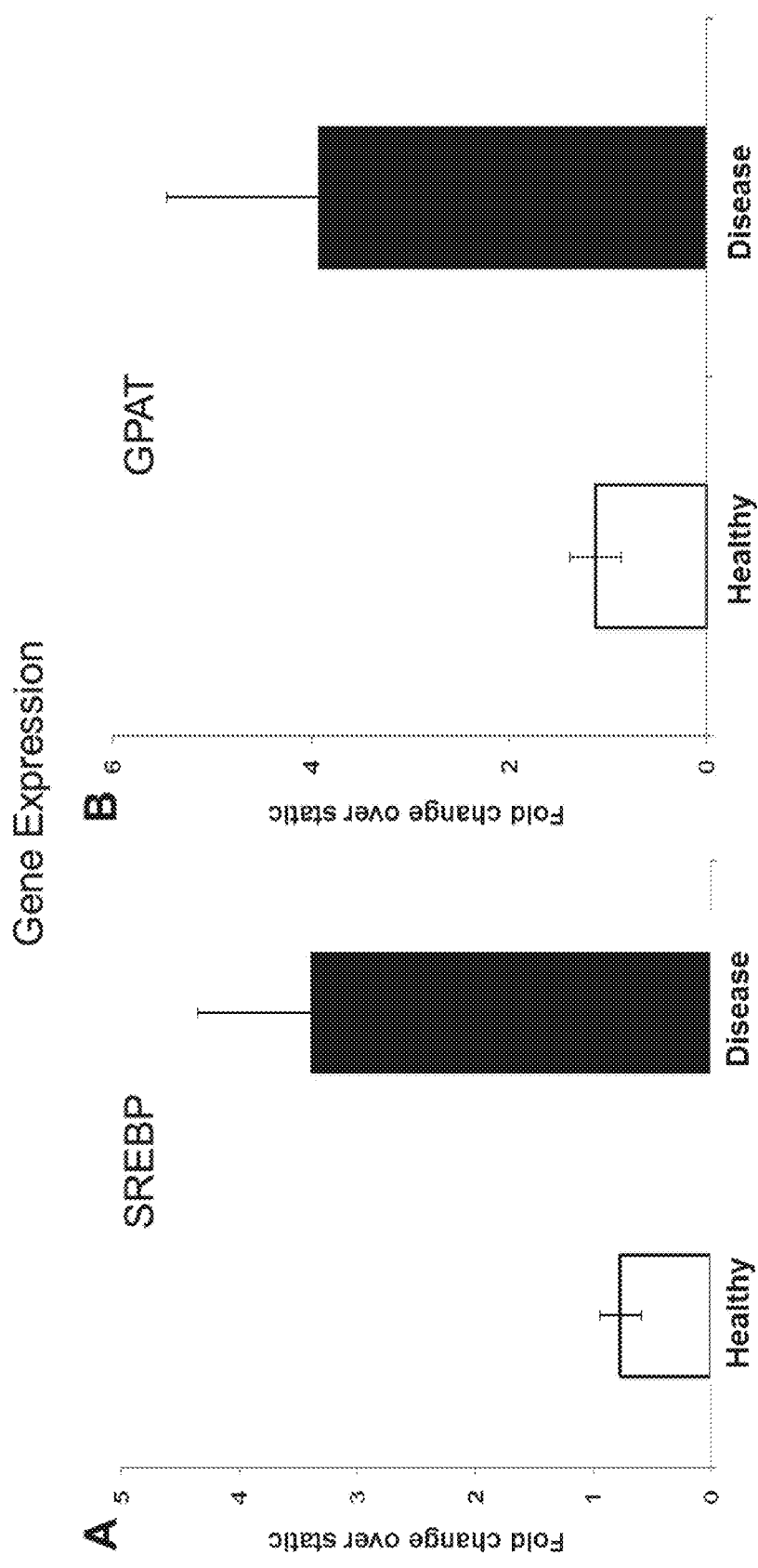
FIGS. 28A-B show exemplary gene expression data for hepatocytes cultured under healthy conditions or conditions that mimic fatty liver disease.
Figure 29:
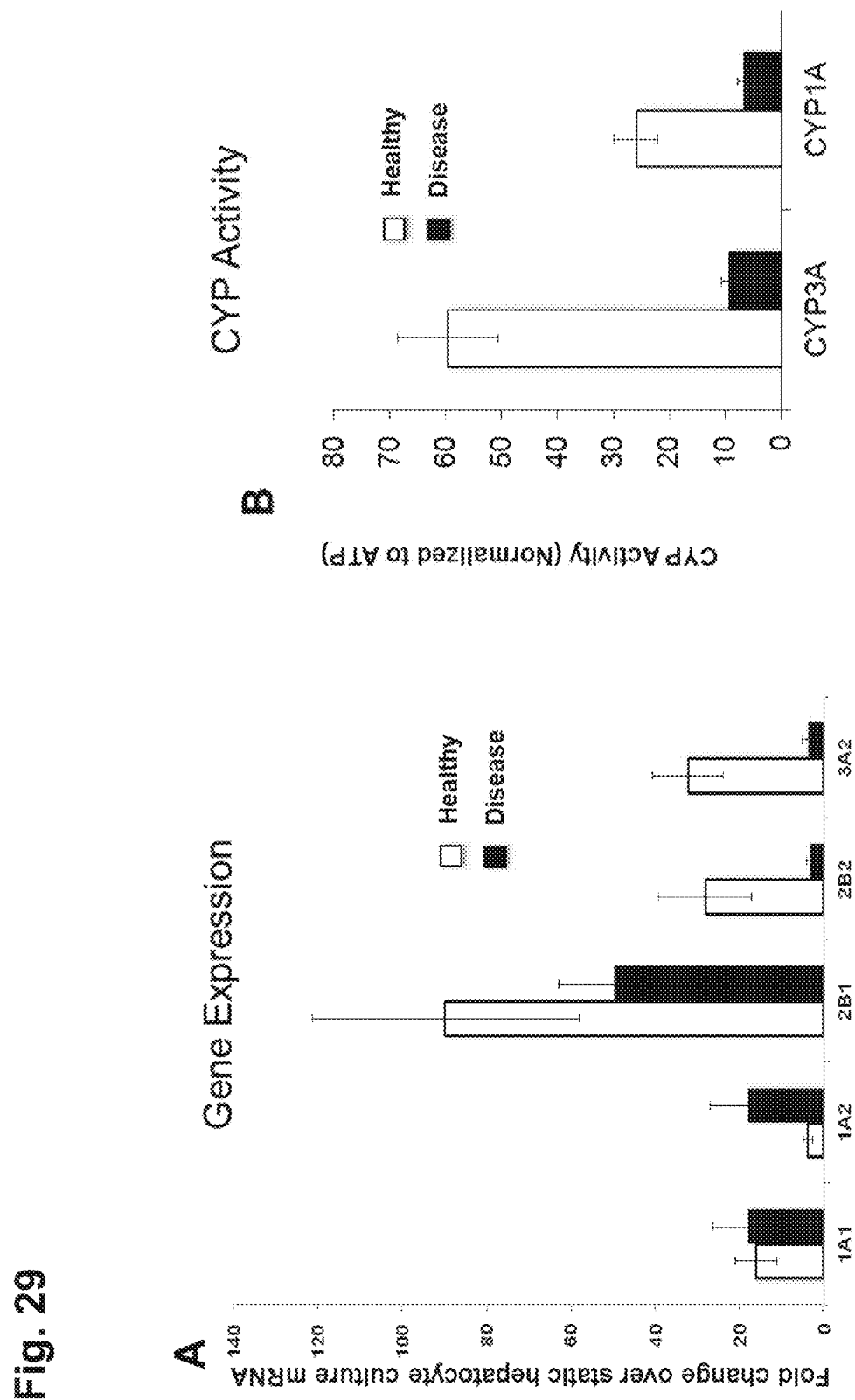
FIGS. 29A-B provide exemplary metabolic gene expression data and cytochrome p450 activity data for hepatocytes cultured under healthy conditions or conditions that mimic fatty liver disease.

Transmission Electron Microscopy:

Hepatocytes cultured in the fatty liver media were also examined by transmission electron microscopy. As shown in FIG. 26, hepatocytes cultured under these conditions accumulate lipid. A large lipid droplet is indicated in the hepatocyte on the left side of the image. Gap junctions between two hepatocytes are also shown, demonstrating the polarized morphology.

Total Lipid and Total Triglycerides:

As shown in FIG. 27, total lipid (FIG. 27A) and total triglycerides (FIG. 27B) were both significantly increased in hepatocytes cultured under the high glucose/high insulin fatty liver conditions in the presence of liver-derived hemodynamics. Oil red O quantification indicated that the total lipid was raised in the disease cultures by about 3-fold as compared to the healthy cultures.

Figure 21:
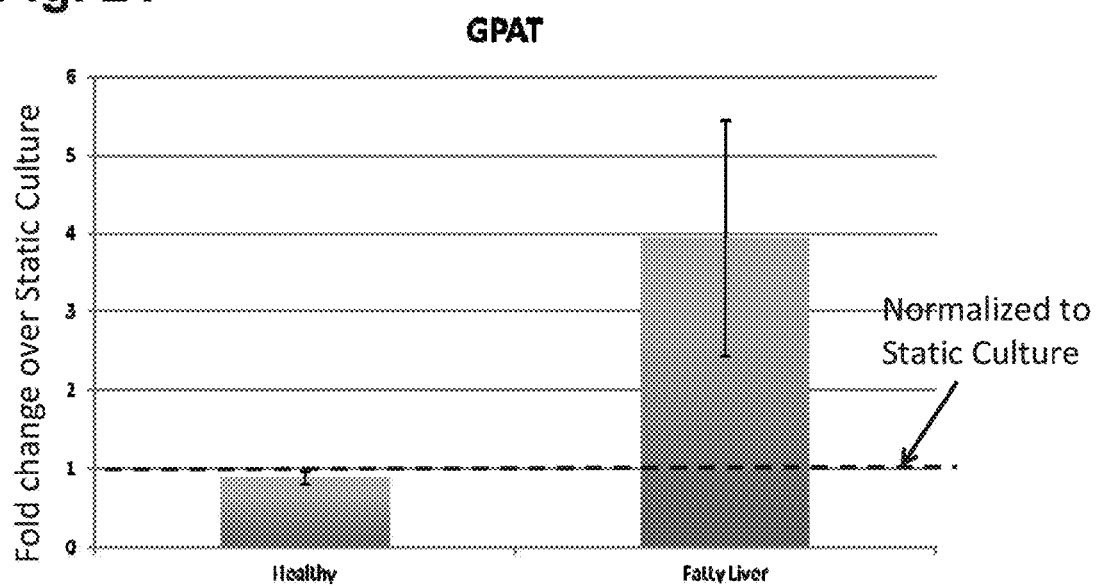
FIG. 21 shows exemplary gene expression data for the in vitro fatty liver model.

Gene Expression:

Glycerol 3-phosphate acyltransferase (GPAT) is a key enzyme involved in triglyceride synthesis and known to upregulated and contribute to steatosis and fatty liver. As shown in FIG. 21, primary rat hepatocytes cultured under controlled hemodynamics in the devices when exposed to pathological conditions (n=9) of high insulin (2 μMol) and high glucose (17.5 mMol) exhibit a significantly higher expression the GPAT gene (p=0.04) compared to those cultured under healthy physiological levels (n=6) of insulin (2 nMol) and glucose (5.5 mMol) in the media. The results are expressed as fold increase over standard static cultures in collagen gel sandwiches (2 μMol insulin and 17.5 mMol glucose).

Similar results are shown in FIG. 28B for hepatocytes cultured under controlled hemodynamics in healthy or fatty liver media containing a lower concentration of dexamethasone. The hepatocytes cultured in the high insulin/high glucose (fatty liver) media exhibited significantly higher levels of GPAT expression as compared to hepatocytes cultured in the healthy media containing lower levels of insulin and glucose. As shown in FIG. 28A, hepatocytes cultured under controlled hemodynamics in the high insulin/high glucose media also exhibited significantly higher levels of expression of sterol regulatory element-binding protein (SREBP), another key gene responsible for lipogenisis, as compared to hepatocytes cultured in the healthy media.

Figure 22:
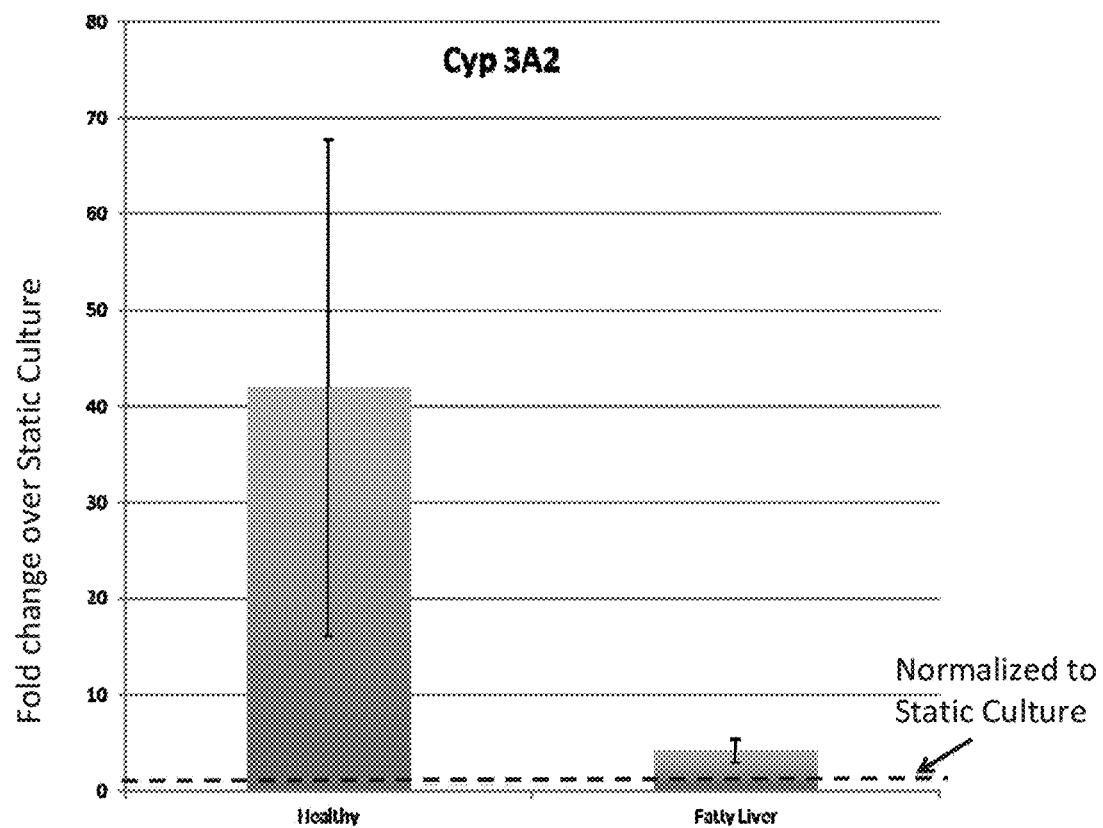
FIG. 22 shows exemplary gene expression data for the in vitro fatty liver model.

These steatotic changes were accompanied by concomitant metabolic changes. Of all the key metabolic enzymes, the cytochrome p450 3A family is responsible for the metabolism of a majority of drugs. As shown in FIG. 22, primary rat hepatocytes cultured under controlled hemodynamics in the devices with healthy physiological levels (n=6) of insulin (2 nMol) and glucose (5.5 mMol) in the media, exhibit a significantly higher expression level of the key metabolic enzyme cytochrome p450 3a2 (Cyp3A2; p=0.03), compared to those cultured under pathological conditions (n=9) with high insulin (2 μMol) and high glucose (17.5 mMol) levels. Both the healthy and pathological fatty liver levels under controlled flow are many fold higher than static cultures in collagen gel sandwiches (2 μM insulin and 17.5 mMol glucose).

Similarly, as shown in FIG. 29A, expression of a number of phase I enzymes involved in drug metabolism are differentially regulated under low and high glucose/insulin conditions. Under hemodynamic flow, hepatocytes under healthy media conditions maintained high levels of mRNA expression of Cyp1a1, Cyp 2b1, 2b2, Cyp3a2, and (20, 90, 30 and 40-fold higher than traditional static cultures respectively), whereas Cyp 2b2 and Cyp 3a2 levels in hepatocytes cultured in the fatty liver media were decreased by 9 and 12 fold compared to healthy.

Cyp Activity:

As shown in FIG. 29B, the activities of CYP3A2 and CYP1A1 were also reduced 3-6-fold under the high insulin/glucose fatty liver conditions compared to healthy, as measured by the p45glo assay.

Figure 30:
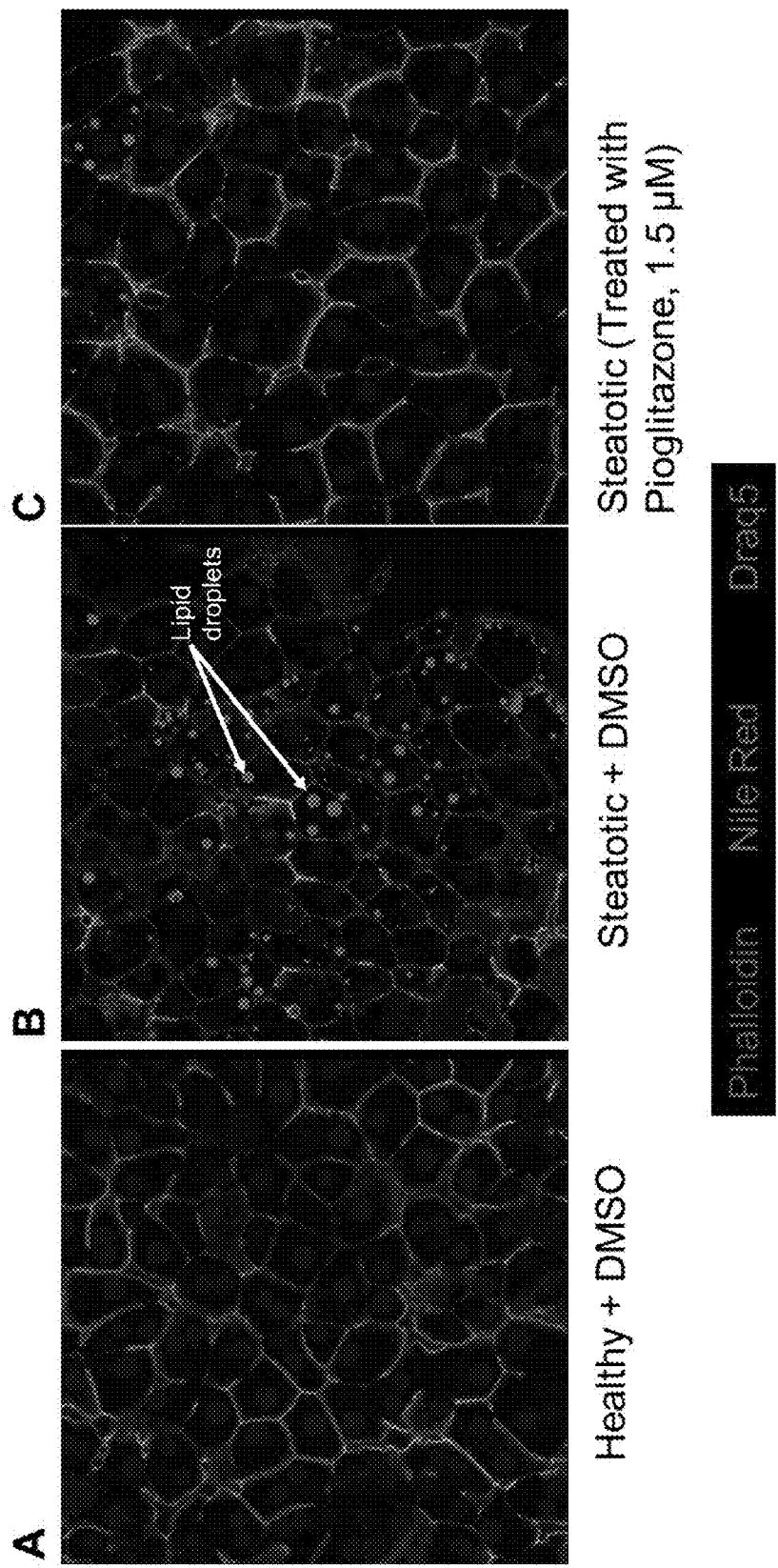
Figure 31:
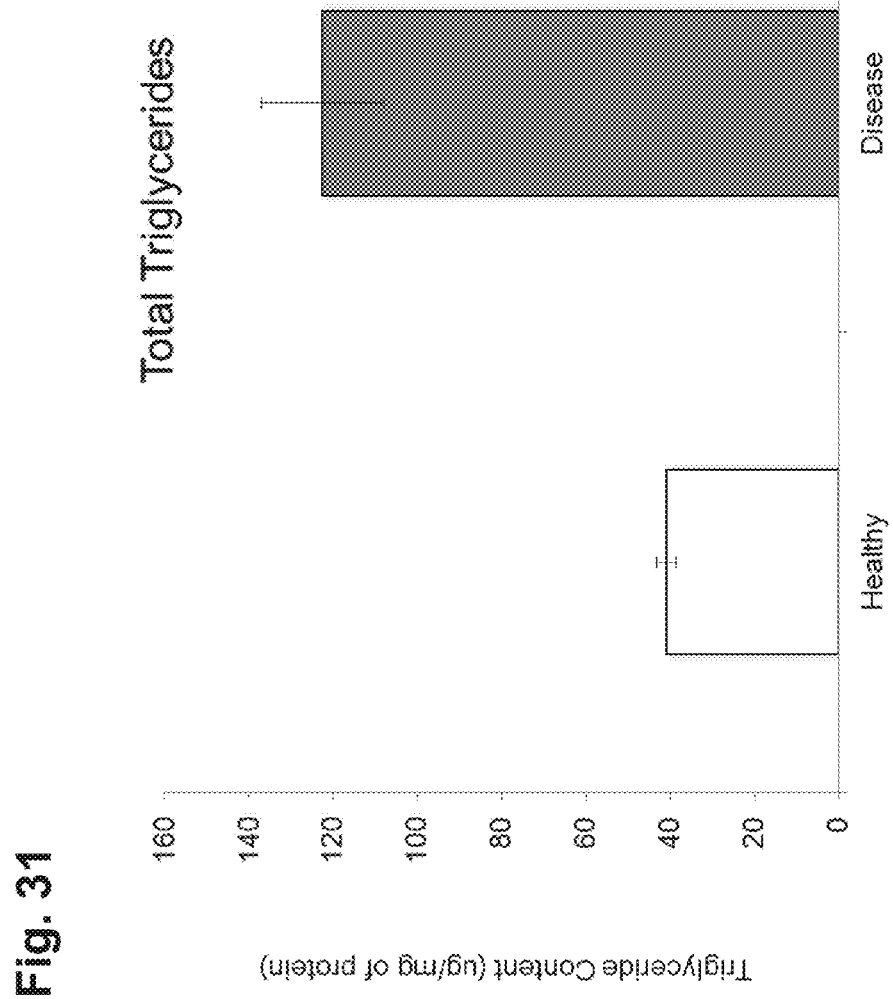
FIG. 31 provides exemplary results from an assay measuring total triglycerides in hepatocytes cultured under healthy conditions or under conditions that mimic fatty liver disease, in the presence or absence of pioglitazone.
Figure 32:
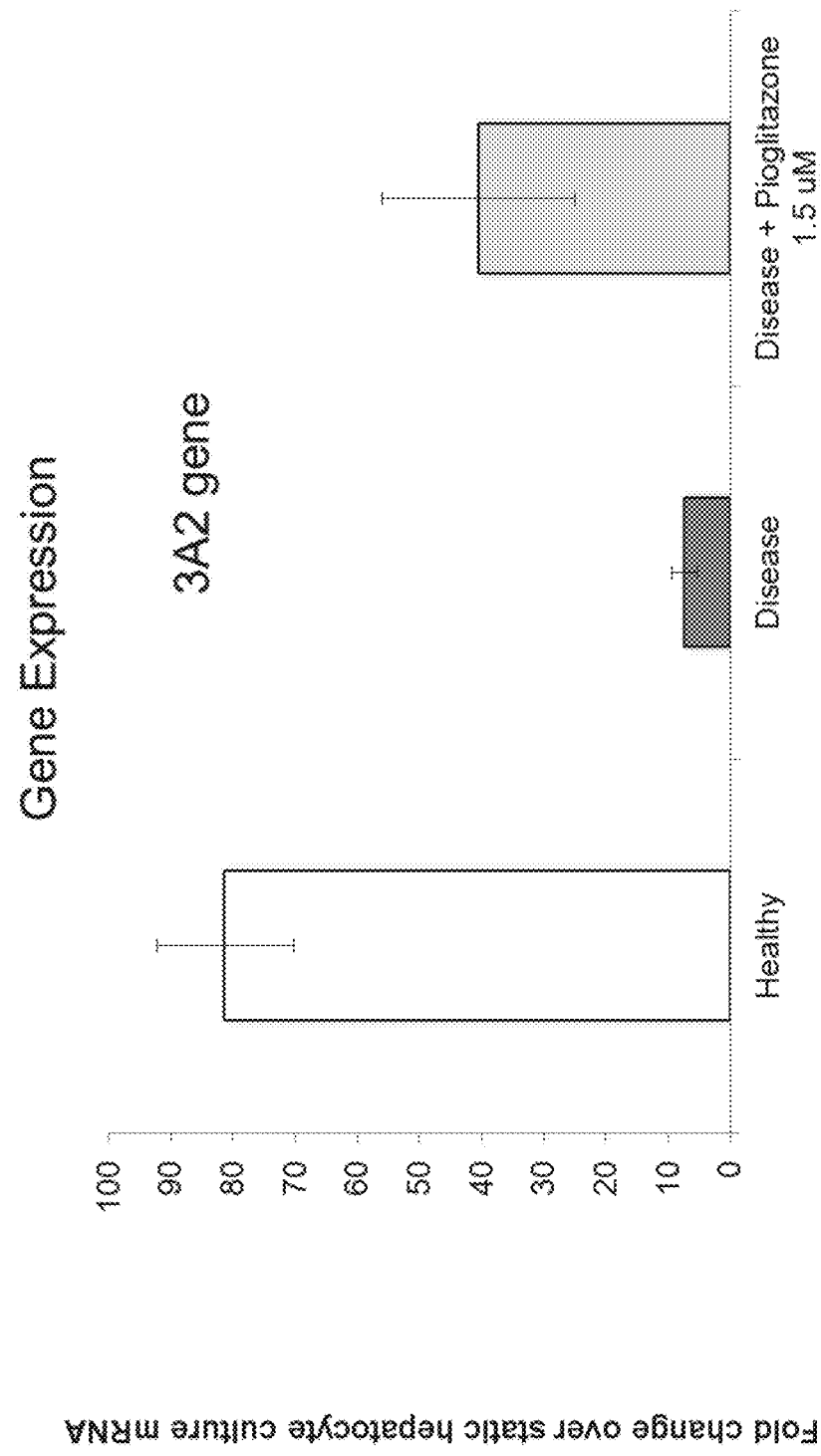
FIG. 32 provides exemplary metabolic gene expression data for hepatocytes cultured under healthy conditions or under conditions that mimic fatty liver disease, in the presence or absence of pioglitazone.

Pioglitazone Treatment:

Pioglitazone, a drug used to treat steatosis, was tested in the fatty liver model to determine if it could reverse the lipid accumulation and metabolic changes induced by the high insulin/glucose fatty liver media. The pioglitazone was added to the media at a concentration of 1.5 μM, a concentration selected based on the therapeutic $C_{max}$ observed for pioglitazone in vivo. Pioglitazone was effective in reducing the lipid buildup and triglyceride content while restoring metabolic gene expression under the disease conditions. As shown in FIG. 30, Nile red staining indicates that treatment with pioglitazone at in vivo therapeutic concentrations decreases lipid droplet formation under steatotic conditions. Pioglitazone also reduced total triglyceride content of hepatocytes cultured in the high insulin/glucose media to levels similar to those seem in the hepatocytes cultured under healthy conditions (FIG. 31). Moreover, as shown in FIG. 32, pioglitazone restored the expression of metabolic genes such as Cyp3A2 which are depressed by the high insulin/glucose disease conditions.

CONCLUSIONS

In summary, a system was developed that preserves in vivo-like hepatocyte phenotype and response, to create a model of hepatic steatosis by inducing pathological steatotic changes in the presence of a high glucose/insulin milieu. Rat hepatocytes under controlled hemodynamics retain their response to insulin and glucose, and hepatocytes cultured under hemodynamic flow develop steatotic changes when cultured in high glucose and insulin ('disease') conditions. The steatosis is mediated via de novo lipogenesis with upregulation of two key genes (SREBP and GPAT), and the increase in lipid accumulation and triglyceride content is accompanied by a concomitant decrease in metabolic gene expression and activity. Treatment with the PPAR-γ agonist pioglitazone helps prevent the buildup of lipid and loss of metabolic activity under the high glucose and insulin conditions. These data demonstrate a novel and important new in vitro model of diet induced non-alcoholic fatty liver disease (NAFLD) for which none currently exist.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above methods without departing from the scope of the invention, it is intended that all matter contained in the above description and shown in the accompanying drawing[s] shall be interpreted as illustrative and not in a limiting sense.

What is claimed is:

1. A method of mimicking a pathological or physiologic condition in vitro, the method comprising:
   adding a culture media and at least one factor to a cell culture container;
   plating a first cell type on a first surface of a porous membrane, and optionally plating a second cell type on a second surface of the porous membrane, wherein the porous membrane is suspended in the cell culture container such that the first surface is proximal and in spaced relation to a bottom surface of the cell culture container, thereby defining within the cell culture container a lower volume comprising the first cell type and an upper volume comprising the optional second cell type, the porous membrane being adapted to permit fluid communication of the cell culture media and physical interaction and communication between cells of the first cell type and cells of the optional second cell type; and
   applying a shear force upon the second cell type or the second surface of the porous membrane in the upper volume, the shear force resulting from flow of the culture media induced by a flow device, the flow mimicking flow to which the at least one cell type is exposed in vivo in the pathological or physiologic condition and the flow device comprising a body adapted for being positioned in the culture media in the upper volume of the container and a motor adapted to rotate the body, wherein:
   for mimicking the pathological condition, the factor is exogenously added to the cell culture container to provide a concentration that is either:
     (i) within the in vivo concentration range of the factor observed in the pathological condition; or
     (ii) within the concentration range of the factor that would result in vivo from administration of a drug or a compound; or
   for mimicking the physiologic condition, the factor is exogenously added to the cell culture container to provide a concentration that is either:
     (i) within the in vivo concentration range of the factor observed in the physiologic condition; or
     (ii) within the concentration range of the factor that would result in vivo from administration of a drug or a compound.

2. An in vitro method of testing a drug or a compound for an effect on the pathological or physiologic condition, the method comprising:
   mimicking the pathological or physiologic condition according to the method of claim 1;
   adding the drug or the compound to the culture media; and
   applying the shear force upon the at least one plated cell type exposed to the drug or the compound; wherein a change in the at least one plated cell type, in the presence of the drug or the compound, indicates that the drug or the compound has an effect on the pathological or physiologic condition.

3. A method of mimicking a pathological or physiologic condition of the liver in vitro, the method comprising:
   adding a culture media and at least one factor to a cell culture container;
   plating at least one hepatic cell type on at least one surface within the cell culture container; and
   applying a shear force upon the at least one plated hepatic cell type, the shear force resulting from flow of the culture media induced by a flow device, the flow mimicking flow to which the at least one hepatic cell type is exposed in vivo in the pathological or physiologic condition, wherein:
   for mimicking the pathological condition, the factor is exogenously added to the cell culture container to provide a concentration that is capable of maintaining the mimicked pathological condition in vitro for a period of time under the shear force, the same concentration of factor being incapable of maintaining the mimicked pathological condition in vitro for the period of time in the absence of the shear force; or
   for mimicking the physiologic condition, the factor is exogenously added to the cell culture container to provide a concentration that is capable of maintaining the mimicked physiologic condition in vitro for a period of time under the shear force, the same concentration of factor being incapable of maintaining the mimicked physiologic condition in vitro for the period of time in the absence of the shear force.

4. The method of claim 1, wherein the pathological condition is mimicked.

5. The method of claim 4, wherein the concentration of the factor in the culture media is within the in vivo concentration range of the factor observed in the pathological condition.

6. The method of claim 4, wherein the concentration of the factor in the culture media is within the concentration range of the factor that would result in vivo from administration of the drug or the compound.

7. The method of claim 1, wherein a change in a level of a marker of the pathological condition in the at least one plated cell type or in the culture media upon application of the shear force, as compared to the level of the marker in the at least one plated cell type or in the culture media in the absence of application of the shear force confirms mimicking of the pathological condition.

8. The method of claim 3, wherein a change in a level of a marker of the pathological condition in the at least one plated hepatic cell type or in the culture media upon application of the shear force, as compared to the level of the marker in the at least one plated hepatic cell type or in the culture media in the absence of application of the shear force confirms mimicking of the pathological condition.

9. The method of claim 1, wherein the physiologic condition is mimicked.

10. The method of claim 9, wherein the concentration of the factor in the culture media is within the in vivo concentration range of the factor observed in the physiologic condition.

11. The method of claim 9, wherein the concentration of the factor in the culture media is within the concentration range of the factor that would result in vivo from administration of the drug or the compound.

12. The method of claim 1, wherein a change in a level of a marker of the physiologic condition in the at least one plated cell type or in the culture media upon application of the shear force, as compared to the level of the marker in the at least one plated cell type or in the culture media in the absence of application of the shear force confirms mimicking of the physiologic condition.

13. The method of claim 3, wherein a change in a level of a marker of the physiologic condition in the at least one plated hepatic cell type or in the culture media upon application of the shear force, as compared to the level of the marker in the at least one plated hepatic cell type or in the culture media in the absence of application of the shear force confirms mimicking of the physiologic condition.

14. The method of claim 3, wherein the physiologic condition is a healthy liver, the factors comprise insulin and glucose, the plating step comprises plating hepatocytes on the surface within the cell culture container; and the shear force is applied indirectly to the plated hepatocytes.

15. The method of claim 14, wherein the hepatocytes are plated on a first surface of a porous membrane, the porous membrane is suspended in the cell culture container such that the first surface is proximal and in spaced relation to a bottom surface of the cell culture container, thereby defining within the cell culture container a lower volume comprising the hepatocytes and an upper volume comprising a second surface of the porous membrane, and the shear force is applied to the second surface of the porous membrane in the upper volume of the container.

16. The method of claim 3, wherein at least one extracellular matrix component is deposited on a first surface of a porous membrane, the at least one hepatic cell type is plated on the at least one extracellular matrix component, the porous membrane is suspended in the cell culture container such that the first surface is proximal and in spaced relation to a bottom surface of the cell culture container, thereby defining within the cell culture container a lower volume comprising the at least one extracellular matrix component and the at least one hepatic cell type and an upper volume comprising a second surface of the porous membrane, and the shear force is applied to the second surface of the porous membrane in the upper volume of the container.

17. The method of claim 1, wherein the culture media comprises the at least one factor at the time of addition to the cell culture container.

18. The method of claim 1 wherein the pathological condition comprises a vascular pathological condition, the factor comprises oxidized low-density lipoprotein (oxLDL), tumor necrosis factor-α (TNFα), glucose, tissue growth factor-β (TGF-β), an elastin degradation product, elastase, vitamin D, an inorganic phosphate, leptin, adiponectin, apelin, aldosterone, angiotensin II, a triglyceride, high-density lipoprotein (HDL), oxidized high-density lipoprotein (oxHDL), a triglyceride-rich lipoprotein, low-density lipoprotein (LDL), insulin, a fatty acid, or a combination thereof; the plating step comprises plating endothelial cells, smooth muscle cells, or endocardial cells on the surface within the cell culture container; and the shear force is applied upon the plated endothelial cells, smooth muscle cells, or endocardial cells.

19. The method of claim 18, further comprising plating the smooth muscle cells on a first surface of a porous membrane, wherein the porous membrane is suspended in the cell culture container such that the first surface is proximal and in spaced relation to a bottom surface of the cell culture container, thereby defining within the cell culture container a lower volume comprising the smooth muscle cells and an upper volume comprising a second surface of the porous membrane, and applying the shear force upon second surface of the porous membrane in the upper volume.

20. The method of claim 19, further comprising plating the endothelial cells on the second surface of the porous membrane.

21. The method of claim 20, wherein the vascular pathological condition comprises atherosclerosis and the factor comprises LDL, oxLDL, TNFα, HDL, a triglyceride-rich lipoprotein, or a combination thereof.

22. The method of claim 20, wherein the vascular pathological condition comprises hypertension and the factor comprises oxLDL, TNFα, angiotensin II, aldosterone, or a combination thereof.

23. The method of claim 20, wherein the vascular pathological condition comprises thrombosis and the factor comprises TNFα, oxLDL, glucose, or a combination thereof.

24. The method of claim 3, wherein the culture media comprises the at least one factor at the time of addition to the cell culture container.

25. The method of claim 3, wherein the surface within the cell culture container comprises a porous membrane suspended in the cell culture container.

26. The method of claim 3, wherein the step of plating at least one hepatic cell type on a surface within the cell culture container comprises plating hepatocytes on a first surface of a porous membrane, and optionally plating a second hepatic cell type on a second surface of the porous membrane, wherein the porous membrane is suspended in the cell culture container such that the first surface is proximal and in spaced relation to a bottom surface of the cell culture container, thereby defining within the cell culture container a lower volume comprising the hepatocytes and an upper volume comprising the optional second hepatic cell type, the porous membrane being adapted to permit fluid communication of the cell culture media and physical interaction and communication between the hepatocytes and cells of the optional second hepatic cell type; and the shear force is applied upon the second hepatic cell type or the second surface of the porous membrane in the upper volume.

27. The method of claim 26, wherein the shear force applied upon the second hepatic cell type or the second surface of the porous membrane results from flow of the culture media induced by a flow device comprising a body adapted for being positioned in the culture media in the upper volume of the container and a motor adapted to rotate the body.

28. The method of claim 26, wherein the second hepatic cell type is present on the second surface of the porous membrane, the second hepatic cell type comprises nonparenchymal hepatic cells, and the shear force is applied upon the nonparenchymal hepatic cells.

29. The method of claim 28, wherein the nonparenchymal hepatic cells comprise sinusoidal endothelial cells, hepatic stellate cells, Kupffer cells, or combinations thereof.

30. The method of claim 3, wherein the shear force is applied indirectly to the at least one plated hepatic cell type.

31. The method of claim 3, wherein the shear force is applied at a rate of about 0.1 dynes/cm$^2$ to about 3.0 dynes/cm$^2$.

32. The method of claim 3, wherein the pathological condition comprises fatty liver disease.

33. The method of claim 32, wherein the factors comprise insulin and glucose, the plating step comprises plating hepatocytes on the surface within the cell culture container, and the shear force is applied indirectly to the plated hepatocytes.

34. An in vitro method of testing a drug or a compound for an effect on a pathological or physiologic condition of the liver, the method comprising:
mimicking the pathological or physiologic condition of the liver according to the method of claim 3;
adding the drug or the compound to the culture media; and
applying the shear force upon the at least one plated hepatic cell type exposed to the drug or the compound;
wherein a change in the at least one plated hepatic cell type, in the presence of the drug or the compound, indicates that the drug or the compound has an effect on the pathological or physiologic condition.

35. The method of claim 3, wherein the pathological condition is mimicked.

36. The method of claim 3, wherein the physiologic condition is mimicked.

37. The method of claim 1, wherein the at least one plated cell type comprises cells isolated from at least one subject having the pathological or physiologic condition, cells isolated from at least one subject having a risk factor for the pathological condition, cells isolated from at least one subject with a single nucleotide polymorphism linked to a pathological condition, cells isolated from at least one subject with an identified genotype linked to drug toxicity, or cells isolated from at least one subject with a single nucleotide polymorphism linked to drug toxicity.

38. The method of claim 1, wherein the at least one plated cell type comprises cells from a human selected on the basis of age, gender, race, epigenetics, disease, nationality, or the presence or absence of one or more single nucleotide polymorphisms.

39. The method of claim 18, wherein the at least one plated cell type is from a normal subject, a subject having diabetes, a hypertensive subject, an aged subject, or an animal genetically modified to model diabetes, hypertension, or aging.

40. The method of claim 3, wherein the at least one plated hepatic cell type comprises cells isolated from at least one subject having the pathological or physiologic condition, cells isolated from at least one subject having a risk factor for the pathological condition, cells isolated from at least one subject with a single nucleotide polymorphism linked to a pathological condition, cells isolated from at least one subject with an identified genotype linked to drug toxicity, or cells isolated from at least one subject with a single nucleotide polymorphism linked to drug toxicity.

41. The method of claim 3, wherein the at least one plated hepatic cell type comprises cells from a human selected on the basis of age, gender, race, epigenetics, disease, nationality, or the presence or absence of one or more single nucleotide polymorphisms.

42. The method of claim 1, wherein the at least one plated cell type comprises primary cells.

43. The method of claim 42, wherein the primary cells comprise a cell lineage derived from stem cells or stem-like cells, the cell lineage derived from stem cells comprising adult stem cells, embryonic stem cells, inducible pluripotent stem cells, or bone marrow-derived stem cells.

44. The method of claim 43, wherein the inducible pluripotent stem cells comprise human inducible pluripotent stem cells.

45. The method of claim 42, wherein the primary cells comprise a cell lineage derived from stem cells, wherein the cell lineage derived from stem cells comprises endothelial cells, smooth muscle cells, cardiac myocytes, hepatocytes, neuronal cells, or endocrine cells.

46. The method of claim 1, wherein the at least one plated cell type comprises immortalized cells.

47. The method of claim 3, wherein the at least one plated hepatic cell type comprises primary cells.

48. The method of claim 47, wherein the primary cells comprise a cell lineage derived from stem cells or stem-like cells, the cell lineage derived from stem cells comprising adult stem cells, embryonic stem cells, inducible pluripotent stem cells, or bone marrow-derived stem cells.

49. The method of claim 48, wherein the inducible pluripotent stem cells comprise human inducible pluripotent stem cells.

50. The method of claim 47, wherein the primary cells comprise a cell lineage derived from stem cells, wherein the cell lineage derived from stem cells comprises hepatocytes.

51. The method of claim 3, wherein the at least one plated hepatic cell type comprises immortalized cells.

52. The method of claim 20, wherein the vascular condition comprises a diabetic vascular condition and the factor comprises oxLDL, TNFα, glucose, HDL, oxHDL, a triglyceride-rich lipoprotein, insulin, a fatty acid, or a combination thereof.

53. The method of claim 1, wherein the first cell type comprises hepatocytes and the optional second cell type comprises a hepatic cell type.

54. The method of claim 53, wherein the second cell type is present on the second surface of the porous membrane, the second cell type comprises nonparenchymal hepatic cells, and the shear force is applied upon the nonparenchymal hepatic cells.

55. The method of claim 54, wherein the nonparenchymal hepatic cells comprise sinusoidal endothelial cells, hepatic stellate cells, Kupffer cells, or combinations thereof.

56. The method of claim 53, wherein the physiologic condition is a healthy liver and the factors comprise insulin and glucose.

57. The method of claim 53, wherein the pathologic condition comprises fatty liver disease and the factors comprise insulin and glucose.

58. The method of claim 53, wherein the method further comprises depositing at least one extracellular matrix component on the first surface of the porous membrane and plating the hepatocytes on the at least one extracellular matrix component.

59. The method of claim 53, wherein the shear force is applied at a rate of about 0.1 dynes/cm$^2$ to about 3.0 dynes/cm$^2$.

60. The method of claim 53, wherein the hepatocytes or the hepatic cell type comprise cells isolated from at least one subject having the pathological or physiologic condition, cells isolated from at least one subject having a risk factor for the pathological condition, cells isolated from at least one subject with a single nucleotide polymorphism linked to a pathological condition, cells isolated from at least one subject with an identified genotype linked to drug toxicity, or cells isolated from at least one subject with a single nucleotide polymorphism linked to drug toxicity.

61. The method of claim 53, wherein the hepatocytes or the hepatic cell type comprise cells from a human selected on the basis of age, gender, race, epigenetics, disease, nationality, or the presence or absence of one or more single nucleotide polymorphisms.

62. The method of claim 53, wherein the hepatocytes or the hepatic cell type comprise primary cells.

63. The method of claim 62, wherein the primary cells comprise a cell lineage derived from stem cells or stem-like cells, the cell lineage derived from stem cells comprising adult stem cells, embryonic stem cells, inducible pluripotent stem cells, or bone marrow-derived stem cells.

64. The method of claim 63, wherein the inducible pluripotent stem cells comprise human inducible pluripotent stem cells.

65. The method of claim 62, wherein the primary cells comprise a cell lineage derived from stem cells, wherein the cell lineage derived from stem cells comprises hepatocytes.

66. The method of claim 53, wherein the hepatocytes or the hepatic cell type comprise immortalized cells.

67. The method of claim 1, wherein the first cell type comprises hepatocytes and the second cell type comprises a hepatic cell type, and wherein the pathological or physiologic condition comprises a pathological or physiologic condition of the liver.

68. A method of mimicking a pathological or physiologic condition of the liver in vitro, the method comprising:
adding a culture media and at least one factor to a cell culture container;
plating hepatocytes on a first surface of a porous membrane and plating nonparenchymal hepatic cells on a second surface of the porous membrane, wherein the porous membrane is suspended in the cell culture container such that the first surface is proximal and in spaced relation to a bottom surface of the cell culture container, thereby defining within the cell culture container a lower volume comprising the hepatocytes and an upper volume comprising the nonparenchymal hepatic cells, the porous membrane being adapted to permit fluid communication of the cell culture media and physical interaction and communication between the hepatocytes and the nonparenchymal hepatic cells; and
applying a shear force upon the nonparenchymal hepatic cells in the upper volume, the shear force resulting from flow of the culture media induced by a flow device, the flow mimicking flow to which the at least one hepatic cell type is exposed in vivo in the pathological or physiologic condition, wherein:
for mimicking the pathological condition, the factor is exogenously added to the cell culture container to provide a concentration that is either:
(i) within the in vivo concentration range of the factor observed in the pathological condition; or
(ii) within the concentration range of the factor that would result in vivo from administration of a drug or a compound; or
(iii) capable of maintaining the mimicked pathological condition in vitro for a period of time under the shear force, the same concentration of factor being incapable of maintaining the mimicked pathological condition in vitro for the period of time in the absence of the shear force; or
for mimicking the physiologic condition, the factor is exogenously added to the cell culture container to provide a concentration that is either:
(i) within the in vivo concentration range of the factor observed in the physiologic condition; or
(ii) within the concentration range of the factor that would result in vivo from administration of a drug or a compound; or
(iii) capable of maintaining the mimicked physiologic condition in vitro for a period of time under the shear force, the same concentration of factor being incapable of maintaining the mimicked physiologic condition in vitro for the period of time in the absence of the shear force.

69. The method of claim 68, wherein the nonparenchymal hepatic cells comprise sinusoidal endothelial cells, hepatic stellate cells, Kupffer cells, or combinations thereof.

70. An in vitro method of testing a drug or a compound for an effect on a pathological or physiologic condition of the liver, the method comprising:
mimicking the pathological or physiologic condition of the liver according to the method of claim 68;
adding the drug or the compound to the culture media; and
applying the shear force upon the plated nonparenchymal hepatic cells exposed to the drug or the compound;
wherein a change in the hepatocytes or the nonparenchymal hepatic cells, in the presence of the drug or the compound, indicates that the drug or the compound has an effect on the pathological or physiologic condition.

71. The method of claim 68, wherein a change in a level of a marker of the pathological condition in the hepatocytes or the nonparenchymal hepatic cells or in the culture media upon application of the shear force, as compared to the level of the marker in the hepatocytes or the nonparenchymal hepatic cells or in the culture media in the absence of application of the shear force confirms mimicking of the pathological condition.

72. The method of claim 68, wherein a change in a level of a marker of the physiologic condition hepatocytes or the nonparenchymal hepatic cells or in the culture media upon application of the shear force, as compared to the level of the marker in the hepatocytes or the nonparenchymal hepatic cells or in the culture media in the absence of application of the shear force confirms mimicking of the physiologic condition.

73. The method of claim 68, wherein the pathological condition is mimicked.

74. The method of claim 68, wherein the physiologic condition is mimicked.

75. The method of claim 74, wherein the physiologic condition is a healthy liver and the factors comprise insulin and glucose.

76. The method of claim 73, wherein the pathologic condition comprises fatty liver disease and the factors comprise insulin and glucose.

77. The method of claim 68, wherein the method further comprises depositing at least one extracellular matrix component on the first surface of the porous membrane and plating the hepatocytes on the at least one extracellular matrix component.

78. The method of claim 68, wherein the culture media comprises the at least one factor at the time of addition to the cell culture container.

79. The method of claim 68, wherein the shear force applied upon the nonparenchymal hepatic cells results from flow of the culture media induced by a flow device comprising a body adapted for being positioned in the culture media in the upper volume of the container and a motor adapted to rotate the body.

80. The method of claim 68, wherein the shear force is applied at a rate of about 0.1 dynes/cm$^2$ to about 3.0 dynes/cm$^2$.

81. The method of claim 68, wherein the hepatocytes or the nonparenchymal hepatic cells comprise cells isolated from at least one subject having the pathological or physiologic condition, cells isolated from at least one subject having a risk factor for the pathological condition, cells isolated from at least one subject with a single nucleotide polymorphism linked to a pathological condition, cells isolated from at least one subject with an identified genotype linked to drug toxicity, or cells isolated from at least one subject with a single nucleotide polymorphism linked to drug toxicity.

82. The method of claim 68, wherein the hepatocytes or the nonparenchymal hepatic cells comprise cells from a human selected on the basis of age, gender, race, epigenetics, disease, nationality, or the presence or absence of one or more single nucleotide polymorphisms.

83. The method of claim 68, wherein the hepatocytes or the nonparenchymal hepatic cells comprise primary cells.

84. The method of claim 83, wherein the primary cells comprise a cell lineage derived from stem cells or stem-like cells, the cell lineage derived from stem cells comprising adult stem cells, embryonic stem cells, inducible pluripotent stem cells, or bone marrow-derived stem cells.

85. The method of claim 84, wherein the inducible pluripotent stem cells comprise human inducible pluripotent stem cells.

86. The method of claim 83, wherein the primary cells comprise a cell lineage derived from stem cells, wherein the cell lineage derived from stem cells comprises hepatocytes.

87. The method of claim 68, wherein the hepatocytes or the hepatic cell type comprise immortalized cells.

88. The method of claim 2, wherein the concentration of the drug or the compound in the culture media is within the concentration range of the drug or the compound that achieves the effect in vivo.

89. The method of claim 88, wherein the concentration of the drug or the compound in the culture media is within the concentration range of the in vivo therapeutic $C_{max}$ for the drug or the compound.

90. The method of claim 34, wherein the concentration of the drug or the compound in the culture media is within the concentration range of the drug or the compound that achieves the effect in vivo.

91. The method of claim 90, wherein the concentration of the drug or the compound in the culture media is within the concentration range of the in vivo therapeutic $C_{max}$ for the drug or the compound.

92. The method of claim 70, wherein the concentration of the drug or the compound in the culture media is within the concentration range of the drug or the compound that achieves the effect in vivo.

93. The method of claim 92, wherein the concentration of the drug or the compound in the culture media is within the concentration range of the in vivo therapeutic $C_{max}$ for the drug or the compound.

94. The method of claim 68, wherein the pathological condition is mimicked, and the concentration of the factor in the culture media is capable of maintaining the mimicked pathological condition in vitro for a period of time under the shear force, the same concentration of factor being incapable of maintaining the mimicked pathological condition in vitro for the period of time in the absence of the shear force.

95. The method of claim 68, wherein the physiologic condition is mimicked, and the concentration of the factor in the culture media is capable of maintaining the mimicked physiologic condition in vitro for a period of time under the shear force, the same concentration of factor being incapable of maintaining the mimicked physiologic condition in vitro for the period of time in the absence of the shear force.

96. The method of claim 73, wherein the concentration of the factor in the culture media is within the in vivo concentration range of the factor observed in the pathological condition.

97. The method of claim 73, wherein the concentration of the factor in the culture media is within the concentration range of the factor that would result in vivo from administration of the drug or the compound.

98. The method of claim 74, wherein the concentration of the factor in the culture media is within the in vivo concentration range of the factor observed in the physiologic condition.

99. The method of claim 74, wherein the concentration of the factor in the culture media is within the concentration range of the factor that would result in vivo from administration of the drug or the compound.

* * * * *

```
                            SEQUENCE LISTING

<160> NUMBER OF SEQ ID NOS: 32

<210> SEQ ID NO 1
<211> LENGTH: 20
<212> TYPE: DNA
<213> ORGANISM: Rattus norvegicus

<400> SEQUENCE: 1
gctgctcttg gccgtcacca                                             20

<210> SEQ ID NO 2
<211> LENGTH: 20
<212> TYPE: DNA
<213> ORGANISM: Rattus norvegicus

<400> SEQUENCE: 2
tgaagggcaa gccccagggt                                             20

<210> SEQ ID NO 3
<211> LENGTH: 20
<212> TYPE: DNA
<213> ORGANISM: Rattus norvegicus

<400> SEQUENCE: 3
cctgcgctac ctgcccaacc                                             20

<210> SEQ ID NO 4
<211> LENGTH: 20
<212> TYPE: DNA
<213> ORGANISM: Rattus norvegicus

<400> SEQUENCE: 4
gggcgcctgt gatgtcctgg                                             20

<210> SEQ ID NO 5
<211> LENGTH: 20
<212> TYPE: DNA
<213> ORGANISM: Rattus norvegicus

<400> SEQUENCE: 5
cggcgggatt ttggcccagt                                             20

<210> SEQ ID NO 6
<211> LENGTH: 20
<212> TYPE: DNA
<213> ORGANISM: Rattus norvegicus

<400> SEQUENCE: 6
caggcttgcc tgtctccgcc                                             20

<210> SEQ ID NO 7
<211> LENGTH: 20
<212> TYPE: DNA
<213> ORGANISM: Rattus norvegicus

<400> SEQUENCE: 7
gctgctggga actctggcgg                                             20
```

<210> SEQ ID NO 8
<211> LENGTH: 20
<212> TYPE: DNA
<213> ORGANISM: Rattus norvegicus

<400> SEQUENCE: 8
ccggcaccaa tgcccgtgta                                                   20

<210> SEQ ID NO 9
<211> LENGTH: 20
<212> TYPE: DNA
<213> ORGANISM: Rattus norvegicus

<400> SEQUENCE: 9
cgcagcagct atgccaccgt                                                   20

<210> SEQ ID NO 10
<211> LENGTH: 21
<212> TYPE: DNA
<213> ORGANISM: Rattus norvegicus

<400> SEQUENCE: 10
cttccagctc tggccctggt c                                                 21

<210> SEQ ID NO 11
<211> LENGTH: 24
<212> TYPE: DNA
<213> ORGANISM: Rattus norvegicus

<400> SEQUENCE: 11
agcgttgctc catgggcata tagt                                              24

<210> SEQ ID NO 12
<211> LENGTH: 24
<212> TYPE: DNA
<213> ORGANISM: Rattus norvegicus

<400> SEQUENCE: 12
tgtcagggat ggtgttggat gaca                                              24

<210> SEQ ID NO 13
<211> LENGTH: 24
<212> TYPE: DNA
<213> ORGANISM: Rattus norvegicus

<400> SEQUENCE: 13
tgtcatggtt acacccgaag acct                                              24

<210> SEQ ID NO 14
<211> LENGTH: 24
<212> TYPE: DNA
<213> ORGANISM: Rattus norvegicus

<400> SEQUENCE: 14
ttgttgttgt ttgctcctcc aggc                                              24

<210> SEQ ID NO 15
<211> LENGTH: 20
<212> TYPE: DNA
<213> ORGANISM: Rattus norvegicus

<400> SEQUENCE: 15
gcgagctcta tgggtatatg                                                   20

<210> SEQ ID NO 16
<211> LENGTH: 20
<212> TYPE: DNA
<213> ORGANISM: Rattus norvegicus

<400> SEQUENCE: 16
agtcctcttc ctcagtcctc                                              20

<210> SEQ ID NO 17
<211> LENGTH: 24
<212> TYPE: DNA
<213> ORGANISM: Rattus norvegicus

<400> SEQUENCE: 17
atatctccct ttttgtggct gcta                                         24

<210> SEQ ID NO 18
<211> LENGTH: 22
<212> TYPE: DNA
<213> ORGANISM: Rattus norvegicus

<400> SEQUENCE: 18
tccgactccg tcttctygat ga                                           22

<210> SEQ ID NO 19
<211> LENGTH: 20
<212> TYPE: DNA
<213> ORGANISM: Rattus norvegicus

<400> SEQUENCE: 19
ggagccatgg attgcacatt                                              20

<210> SEQ ID NO 20
<211> LENGTH: 21
<212> TYPE: DNA
<213> ORGANISM: Rattus norvegicus

<400> SEQUENCE: 20
aggccaggga agtcactgtc t                                            21

<210> SEQ ID NO 21
<211> LENGTH: 20
<212> TYPE: DNA
<213> ORGANISM: Rattus norvegicus

<400> SEQUENCE: 21
ctatgtccgg acccgcacgc                                              20

<210> SEQ ID NO 22
<211> LENGTH: 20
<212> TYPE: DNA
<213> ORGANISM: Rattus norvegicus

<400> SEQUENCE: 22
ctatgtccgg acccgcacgc                                              20

<210> SEQ ID NO 23
<211> LENGTH: 24
<212> TYPE: DNA
<213> ORGANISM: Rattus norvegicus

<400> SEQUENCE: 23

```
actctgcaac ggagttgtgg aaga                                              24

<210> SEQ ID NO 24
<211> LENGTH: 24
<212> TYPE: DNA
<213> ORGANISM: Rattus norvegicus

<400> SEQUENCE: 24
tcggatgact ccaaccctat cctt                                              24

<210> SEQ ID NO 25
<211> LENGTH: 22
<212> TYPE: DNA
<213> ORGANISM: Rattus norvegicus

<400> SEQUENCE: 25
tgtggagcca caggacttac aa                                                22

<210> SEQ ID NO 26
<211> LENGTH: 24
<212> TYPE: DNA
<213> ORGANISM: Rattus norvegicus

<400> SEQUENCE: 26
agccaaccca cgtgagagaa gaaa                                              24

<210> SEQ ID NO 27
<211> LENGTH: 24
<212> TYPE: DNA
<213> ORGANISM: Rattus norvegicus

<400> SEQUENCE: 27
atgtggacct gcattccttc ccat                                              24

<210> SEQ ID NO 28
<211> LENGTH: 24
<212> TYPE: DNA
<213> ORGANISM: Rattus norvegicus

<400> SEQUENCE: 28
ttgcccatgt ccttgtaatg tgcg                                              24

<210> SEQ ID NO 29
<211> LENGTH: 23
<212> TYPE: DNA
<213> ORGANISM: Rattus norvegicus

<400> SEQUENCE: 29
gaggagtgtg gaagaacgga ttc                                               23

<210> SEQ ID NO 30
<211> LENGTH: 21
<212> TYPE: DNA
<213> ORGANISM: Rattus norvegicus

<400> SEQUENCE: 30
aggaactggc ggtctgtgta g                                                 21

<210> SEQ ID NO 31
<211> LENGTH: 21
<212> TYPE: DNA
<213> ORGANISM: Rattus norvegicus

<400> SEQUENCE: 31
```

```
tcatcgacac ttaccttctg c                                              21

<210> SEQ ID NO 32
<211> LENGTH: 22
<212> TYPE: DNA
<213> ORGANISM: Rattus norvegicus

<400> SEQUENCE: 32
agtgtatggc attttggtac ga                                             22
```